United States Patent
Torgerson et al.

(10) Patent No.: US 9,320,901 B2
(45) Date of Patent: Apr. 26, 2016

(54) STIMULATION WITH UTILIZATION OF NON-SELECTED ELECTRODE

(75) Inventors: Nathan A. Torgerson, Andover, MN (US); Steven M. Goetz, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 282 days.

(21) Appl. No.: 12/769,149

(22) Filed: Apr. 28, 2010

(65) Prior Publication Data
US 2011/0270357 A1 Nov. 3, 2011

(51) Int. Cl.
*A61N 1/05* (2006.01)
*A61N 1/36* (2006.01)
*A61N 1/08* (2006.01)

(52) U.S. Cl.
CPC ........ *A61N 1/36082* (2013.01); *A61N 1/36071* (2013.01); *A61N 1/08* (2013.01)

(58) Field of Classification Search
CPC ............ A61N 1/37247; A61N 1/0551; A61N 1/36146; A61N 1/36185; A61N 1/3993
USPC .......................................... 607/30, 46, 55–60
See application file for complete search history.

(56) References Cited

U.S. PATENT DOCUMENTS

| | | |
|---|---|---|
| 4,592,359 A | 6/1986 | Galbraith |
| 4,931,795 A | 6/1990 | Gord |
| 5,190,035 A | 3/1993 | Salo et al. |
| 5,241,472 A | 8/1993 | Gur et al. |
| 5,501,703 A | 3/1996 | Holsheimer et al. |
| 5,713,922 A | 2/1998 | King |
| 5,776,172 A | 7/1998 | Schulman et al. |
| 5,800,465 A | 9/1998 | Thompson et al. |
| 5,895,416 A | 4/1999 | Barreras, Sr. et al. |
| 5,916,238 A | 6/1999 | Hauser et al. |
| 5,954,758 A | 9/1999 | Peckham et al. |
| 6,341,234 B1 | 1/2002 | Thong et al. |
| 6,393,325 B1 | 5/2002 | Mann et al. |
| 6,421,564 B1 | 7/2002 | Yerich et al. |

(Continued)

FOREIGN PATENT DOCUMENTS

| | | |
|---|---|---|
| EP | 2039391 A1 | 3/2009 |
| WO | 0154579 A1 | 8/2001 |

(Continued)

OTHER PUBLICATIONS

Bourret et al., "Programmable High-Amplitude Balanced Stimulus Current-Source for Implantable Microstimulators," Proceedings of the 19th Annual International Conference of the IEEE Engineering in Medicine and Biology Society, Oct. 30-Nov. 2, 1997, pp. 1938-1941.

(Continued)

*Primary Examiner* — Michael Kahelin
*Assistant Examiner* — Minh Duc Pham
(74) *Attorney, Agent, or Firm* — Shumaker & Sieffert, P.A.

(57) ABSTRACT

This disclosure describes techniques that support delivering electrical stimulation current via at least two user-selected electrodes of an implantable medical device (IMD) and automatically delivering balancing current below via at least one non-selected electrode. Balancing currents delivered via the at least one non-selected electrode may be configured with an amplitude below a perception threshold of a patient. Delivery of balancing current via the at least one third electrode may allow an implantable medical device to automatically balance the total current delivered to a patient.

56 Claims, 38 Drawing Sheets

(56) References Cited

U.S. PATENT DOCUMENTS

| | | |
|---|---|---|
| 6,505,078 B1 | 1/2003 | King et al. |
| 6,516,227 B1 | 2/2003 | Meadows et al. |
| 6,587,724 B2 | 7/2003 | Mann |
| 6,609,032 B1 | 8/2003 | Woods et al. |
| 6,625,482 B1 | 9/2003 | Panescu et al. |
| 6,799,070 B2 | 9/2004 | Wolfe et al. |
| 6,853,863 B2 | 2/2005 | Carter et al. |
| 6,895,280 B2 | 5/2005 | Meadows et al. |
| 6,909,917 B2 | 6/2005 | Woods et al. |
| 7,035,690 B2 | 4/2006 | Goetz |
| 7,127,297 B2 | 10/2006 | Law et al. |
| 7,174,210 B1 | 2/2007 | Levine |
| 7,180,760 B2 | 2/2007 | Varrichio et al. |
| 7,216,001 B2 | 5/2007 | Hacker et al. |
| 7,251,529 B2 | 7/2007 | Greenwood-Van Meerveld |
| 7,271,663 B2 | 9/2007 | Baum et al. |
| 7,317,948 B1 | 1/2008 | King et al. |
| 7,386,348 B2 | 6/2008 | North et al. |
| 7,387,603 B2 | 6/2008 | Gross et al. |
| 7,389,147 B2 | 6/2008 | Wahlstrand et al. |
| 7,463,928 B2 | 12/2008 | Lee et al. |
| 7,477,723 B2 | 1/2009 | Kamegawa et al. |
| 7,505,809 B2 | 3/2009 | Strommer et al. |
| 7,519,428 B1 | 4/2009 | Palmer |
| 7,519,431 B2 | 4/2009 | Goetz et al. |
| 7,522,962 B1 | 4/2009 | Doron et al. |
| 7,526,341 B2 | 4/2009 | Goetz et al. |
| 7,567,834 B2 | 7/2009 | Clayton et al. |
| 7,571,007 B2 | 8/2009 | Erickson et al. |
| 7,623,918 B2 | 11/2009 | Goetz |
| 7,768,151 B2 | 8/2010 | Andreu et al. |
| 7,974,697 B2 | 7/2011 | Maschino et al. |
| 2004/0059395 A1 | 3/2004 | North et al. |
| 2004/0210273 A1 | 10/2004 | Wang |
| 2004/0267330 A1 | 12/2004 | Lee et al. |
| 2005/0065556 A1 | 3/2005 | Reghabi et al. |
| 2005/0131464 A1 | 6/2005 | Heinrich et al. |
| 2006/0178706 A1 | 8/2006 | Lisogurski et al. |
| 2006/0195145 A1 | 8/2006 | Lee et al. |
| 2006/0229687 A1 | 10/2006 | Goetz et al. |
| 2006/0241720 A1 | 10/2006 | Woods et al. |
| 2006/0259079 A1 | 11/2006 | King |
| 2006/0259099 A1 | 11/2006 | Goetz et al. |
| 2006/0293609 A1 | 12/2006 | Stahmann et al. |
| 2007/0100377 A1* | 5/2007 | Armstrong et al. ............... 607/2 |
| 2007/0100408 A1 | 5/2007 | Gerber et al. |
| 2007/0203537 A1 | 8/2007 | Goetz et al. |
| 2007/0203540 A1 | 8/2007 | Goetz et al. |
| 2007/0203541 A1 | 8/2007 | Goetz et al. |
| 2007/0203542 A1 | 8/2007 | Goetz et al. |
| 2007/0203544 A1 | 8/2007 | Goetz et al. |
| 2007/0203546 A1 | 8/2007 | Stone et al. |
| 2008/0004674 A1 | 1/2008 | King et al. |
| 2008/0046036 A1* | 2/2008 | King et al. ..................... 607/59 |
| 2008/0071324 A1 | 3/2008 | Miesel et al. |
| 2008/0082137 A1* | 4/2008 | Kieval et al. ................... 607/30 |
| 2008/0109048 A1 | 5/2008 | Moffitt |
| 2008/0154340 A1 | 6/2008 | Goetz et al. |
| 2008/0163097 A1 | 7/2008 | Goetz et al. |
| 2008/0183256 A1 | 7/2008 | Keacher |
| 2008/0215118 A1 | 9/2008 | Goetz et al. |
| 2008/0215119 A1* | 9/2008 | Woods et al. ................... 607/59 |
| 2008/0288023 A1 | 11/2008 | John |
| 2008/0294211 A1 | 11/2008 | Moffitt |
| 2009/0018617 A1 | 1/2009 | Skelton et al. |
| 2009/0024189 A1 | 1/2009 | Lee et al. |
| 2009/0149917 A1 | 6/2009 | Whitehurst et al. |
| 2010/0023069 A1 | 1/2010 | Moffitt et al. |
| 2010/0023070 A1 | 1/2010 | Moffitt et al. |
| 2010/0106219 A1* | 4/2010 | Torgerson et al. ............... 607/59 |

FOREIGN PATENT DOCUMENTS

| | | |
|---|---|---|
| WO | 2009076211 A1 | 6/2009 |
| WO | 2010011721 A1 | 1/2010 |

OTHER PUBLICATIONS

Kim et al., "A 64-Site Multishank CMOS Low-Profile Neural Stimulating Probe," IEEE Journal of Solid State Circuits, vol. 31, No. 9, Sep. 1996, pp. 1230-1238.

St-Amand et al., "Design and Optimization of a Low DC Offset CMOS Current-Source Dedicated to Implantable Miniaturized Stimulators," Analog Integrated Circuits and Signal Processing, vol. 11, 1996, pp. 47-61.

Office Action from U.S. Appl. No. 12/829,089, dated Oct. 17, 2012, 29 pp.

Response to Office Action dated Aug. 10, 2012, from U.S. Appl. No. 12/906,418, filed Oct. 9, 2012, 19 pp.

Office Action from U.S. Appl. No. 12/829,089, dated Jan. 28, 2013, 30 pp.

Response to office Action for U.S. Appl. No. 12/829,089, dated filed Apr. 29, 2013, 17 pages.

Final Office Action from U.S. Appl. No. 12/906,418, Aug. 10, 2012, 15 pp.

Office Action from U.S. Appl. No. 12/696,992, dated Sep. 13, 2012, 6 pp.

Abstract of: Bian et al., "Double electrodes simultaneous stimulation and implantation technique in deep brain stimulation," Chin J. Traumatol 8(4):253-256, Aug. 2005.

Office Action from U.S. Appl. No. 12/829,108, dated Sep. 17, 2012, 34 pp.

Office Action from U.S. Appl. No. 12/696,988, dated Dec. 14, 2010, 26 pp.

Response to Office Action dated Sep. 13, 2012, from U.S. Appl. No. 12/696,992, filed Dec. 10, 2012, 14 pp.

Response to Office Action dated Oct. 17, 2012, from U.S. Appl. No. 12/829,089, filed Dec. 18, 2012, 16 pp.

Response to Office Action dated Sep. 21, 2012, from U.S. Appl. No. 13/156,011, filed Dec. 21, 2012, 15 pp.

Response to Office Action dated Sep. 17, 2012, from U.S. Appl. No. 12/829,108, filed Dec. 14, 2012, 24 pp.

Office Action from U.S. Appl. No. 12/829,108, dated Jan. 9, 2013, 33 pp.

Office Action from U.S. Appl. No. 12/696,992, dated Jan. 9, 2013, 5 pp.

Notice of Allowance from U.S. Appl. No. 13/156,011, dated Jun. 13, 2013, 13 pp.

Notice of Allowance from U.S. Appl. No. 12/829,089, dated May 15, 2013, 9 pp.

Notice of Allowance from U.S. Appl. No. 12/906,418, dated Dec. 23, 2014, 9 pp.

Response to Office Action dated Sep. 11, 2014, from U.S. Appl. No. 12/906,418, dated Dec. 10, 2014, 18 pp.

Office Action from U.S. Appl. No. 12/906,418, dated Sep. 11, 2014, 6 pp.

U.S. Appl. No. 12/696,988, by Nathan A. Torgerson, filed Jan. 29, 2010.

U.S. Appl. No. 12/696,992, by Nathan A. Torgerson, filed Jan. 29, 2010.

U.S. Appl. No. 12/829,089, by Nathan A. Torgerson, filed Jul. 1, 2010.

U.S. Appl. No. 61/253,759, by Steven M. Goetz, filed Oct. 21, 2009.
U.S. Appl. No. 61/353,842, by Steven M. Goetz, filed Jun. 11, 2010.
U.S. Appl. No. 61/048,774, by John C. Rondoni, filed Apr. 29, 2008.
U.S. Appl. No. 12/829,108, by Steven M. Goetz, filed Jul. 1, 2010.

Lee et al., "AIM Targeting Techniuqe: A Novel Method of Focusing the Volume of Activation on the Dorsal Column with Multiple Independent Current Control in a Computational Model," Boston Scientific Neuromodulation, Valencia, California, presented at 13th North American Neuromodulation Society Annual Meeting, Las Vegas, Nevada, Dec. 3-6, 2009, Poster ID A107, 2 pp.

Office Action from U.S. Appl. No. 12/906,418, dated Mar. 7, 2012, 18 pp.

* cited by examiner

STIMULATION WITH UTILIZATION OF NON-SELECTED ELECTRODE

TECHNICAL FIELD

The disclosure relates to medical devices and, more particularly, to medical devices that deliver electrical stimulation therapy.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads.

Medical electrical stimulators may be used to deliver electrical stimulation therapy to patients to relieve a variety of symptoms or conditions such as chronic pain, tremor, Parkinson's disease, depression, epilepsy, urinary or fecal incontinence, pelvic pain, sexual dysfunction, obesity, or gastroparesis. An electrical stimulator may be configured to deliver electrical stimulation therapy via leads that include electrodes implantable proximate to the spinal cord, pelvic nerves, gastrointestinal organs, peripheral nerves, or within the brain of a patient. Stimulation proximate the spinal cord and within the brain are often referred to as spinal cord stimulation (SCS) and deep brain stimulation (DBS), respectively.

A clinician selects values for a number of programmable stimulation parameters in order to define the electrical stimulation therapy to be delivered to a patient. For example, the clinician may select a current or voltage amplitude of the stimulation, and various characteristics of the stimulation waveform. In addition, the clinician may specify an electrode configuration used to deliver stimulation, including selected electrode combinations and electrode polarities. If the stimulation is delivered in the form of pulses, for example, the clinician may specify a current or voltage pulse amplitude, pulse width and pulse rate. A set of parameter values may be referred to as a stimulation program. A program group may include multiple programs. Multiple programs in a program group may be delivered on a simultaneous, time-interleaved, or overlapping basis.

SUMMARY

In general, this disclosure describes techniques for substantially simultaneously delivering electrical stimulation via at least one electrode on an implantable medical device (IMD) housing and two or more electrodes on one or more leads coupled to the housing. At least one of the lead electrodes has the same polarity as an electrode on the housing of the IMD. The techniques may allow a user to transition between a stimulation setting that uses a unipolar electrode arrangement to a stimulation setting that uses a bipolar electrode arrangement, and permit a range of hybrid electrode arrangements that make use of various combinations of unipolar and bipolar relationships between the electrodes. For convenience, a hybrid stimulation arrangement that combines both unipolar and bipolar electrode relationships also may be referred to as an omnipolar arrangement.

This disclosure also describes techniques that support balancing stimulation currents delivered by two or more electrodes on one or more leads as described above with sub-threshold electrical currents delivered via one or more lead electrodes, or other electrodes located in the body, configured to deliver balancing current. It may be desirable for the balancing currents according to this technique to be delivered by sub-threshold electrodes, i.e., electrodes that deliver energy (e.g., current, voltage) at amplitude levels below a threshold at which stimulation can be perceived by a patient.

In one example, the disclosure provides a method. The method includes receiving, via a user interface of a programmer device for an implantable electrical stimulator, user input specifying at least one first user-selected electrode to deliver electrical stimulation of a first polarity and at least one second user-selected electrode to deliver electrical stimulation of a second polarity different than the first polarity for delivery of electrical stimulation from an implantable electrical stimulator to a patient. The method further includes receiving, via the user interface, user input specifying amounts of electrical stimulation current to be supplied via the at least one first user-selected electrode and the at least one second user-selected electrode. The method further includes automatically selecting at least one third electrode not specified as a user-selected electrode to deliver electrical stimulation to substantially balance the electrical stimulation current to be delivered via the at least one first user-selected electrode and the at least one second user-selected electrode. The method further includes defining a program to control delivery of the electrical stimulation by the stimulator based on the user input.

In another example, the disclosure provides a computer-readable storage medium comprising instructions. The instructions cause a processor to receive, via a user interface of a programmer device for an implantable electrical stimulator, user input specifying at least one first user-selected electrode to deliver electrical stimulation of a first polarity and at least one second user-selected electrode to deliver electrical stimulation of a second polarity different than the first polarity for delivery of electrical stimulation from an implantable electrical stimulator to a patient. The instructions further cause the processor to receive, via the user interface, user input specifying amounts of electrical stimulation current to be supplied via the at least one first user-selected electrode and the at least one second user-selected electrode. The instructions further cause the processor to automatically select at least one non user-selected third electrode to deliver electrical stimulation to substantially balance the electrical stimulation delivered by the at least one first user-selected electrode and the at least one second user-selected electrode. The instructions further cause the processor to define a program to control delivery of the electrical stimulation by the stimulator based on the user input.

In another example, the disclosure provides a device. The device includes means for receiving, via a user interface of a programmer device for an implantable electrical stimulator, user input specifying at least one first user-selected electrode to deliver electrical stimulation of a first polarity and at least one second user-selected electrode to deliver electrical stimulation of a second polarity different than the first polarity for delivery of electrical stimulation from an implantable electrical stimulator to a patient. The device further includes means for receiving, via the user interface, user input specifying amounts of electrical stimulation current to be supplied via the at least one first user-selected electrode and the at least one second user-selected electrode. The device further includes means for automatically selecting at least one third electrode to deliver electrical stimulation to substantially balance electrical stimulation delivered by the at least one first user-selected electrode and the at least one second user-selected electrode. The device further includes means for defining a program to control delivery of the electrical stimulation by the stimulator based on the user input. In another example, this disclosure provides a device. The device includes a programmer for an implantable electrical stimulator. The programmer includes a user interface that receives user input specifying at least one first user-selected electrode to deliver electrical stimulation of a first polarity and at least one second user-selected electrode to deliver electrical stimulation of a second polarity different than the first polarity for delivery of electrical stimulation from an implantable electrical stimulator to a patient, wherein the user interface further receives user input specifying amounts of electrical stimulation current to be supplied via the at least one first user-selected electrode and the at least one second user-selected electrode. The programmer further includes a processor that automatically selects at least one non user-selected third electrode to deliver electrical stimulation to substantially balance the electrical stimulation delivered by the at least one first user-selected electrode and the at least one second user-selected electrode, wherein the processor defines a program to control delivery of the electrical stimulation by the implantable electrical stimulator based on the user input.

In another example, the disclosure provides a system. The system includes an implantable electrical stimulator and a programmer. The programmer includes a user interface that receives, via a user interface of a programmer device for an implantable electrical stimulator, user input specifying at least one first user-selected electrode to deliver electrical stimulation of a first polarity and at least one second user-selected electrode to deliver electrical stimulation of a second polarity different than the first polarity for delivery of electrical stimulation from an implantable electrical stimulator to a patient. The user interface further receives, via the user interface, user input specifying amounts of electrical stimulation current to be supplied via the at least one first user-selected electrode and the at least one second user-selected electrode. The programmer automatically selects at least one third electrode to deliver electrical stimulation to substantially balance electrical stimulation delivered by the at least one first user-selected electrode and the at least one second user-selected electrode. The programmer further includes a processor that defines a program to control delivery of the electrical stimulation by the stimulator based on the user input.

The details of one or more aspects of the disclosure are set forth in the accompanying drawings and the description below. Other features, objects, and advantages will be apparent from the description and drawings, and from the claims.

DETAILED DESCRIPTION

Figure 1:
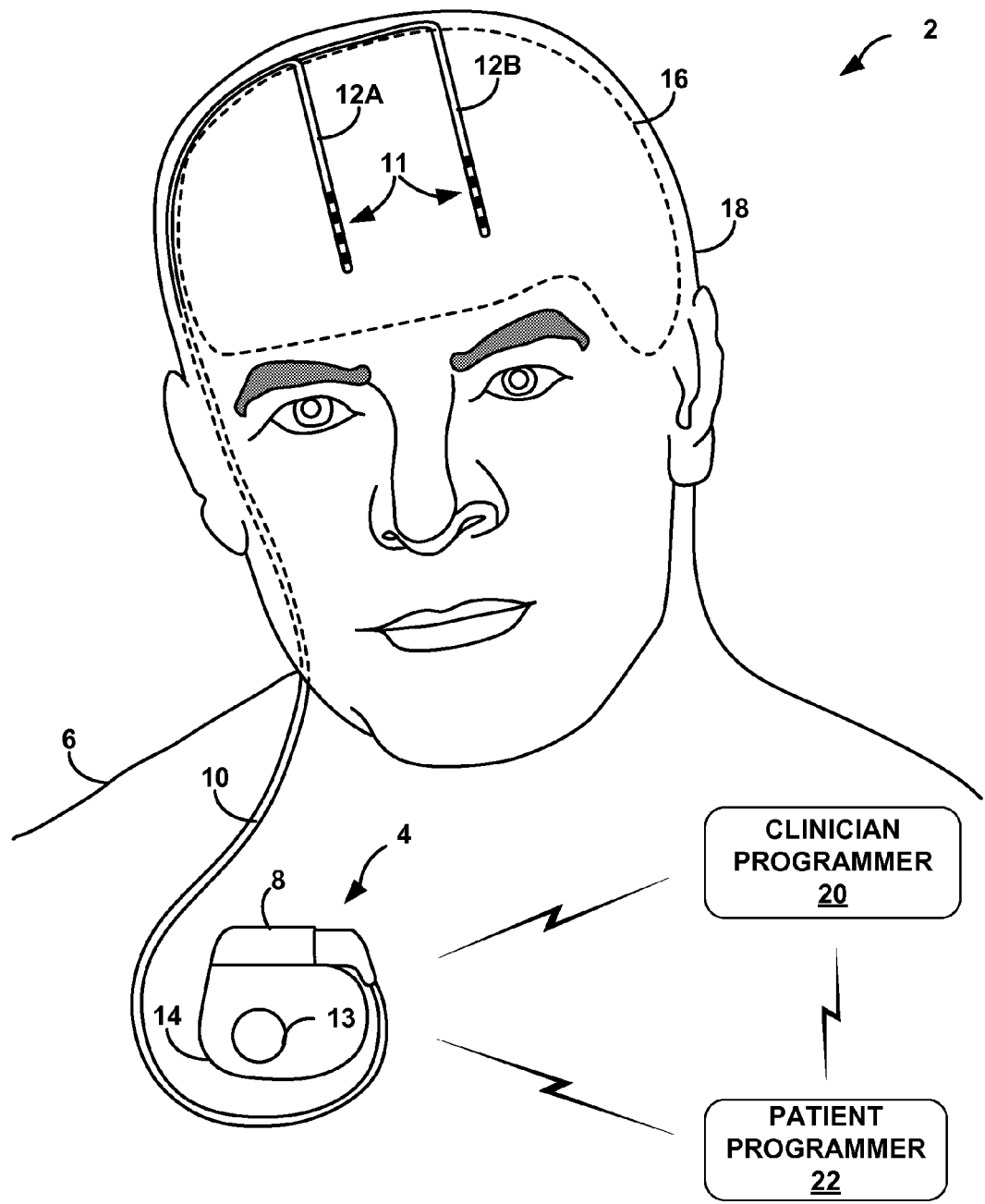
FIG. 1 is a conceptual diagram illustrating an example therapy system that includes an implantable stimulator coupled to a stimulation lead.

This disclosure describes techniques that support delivering electrical stimulation having a first polarity via an electrode on a housing of an implantable medical device (IMD) while substantially simultaneously delivering electrical stimulation having the first polarity via one or more electrodes on one or more leads engaged to the IMD, in conjunction with one or more electrodes delivering electrical stimulation having a second polarity opposite the first polarity on the one or more leads. The housing of the IMD alternatively may be referred to as a case or can. The stimulation may be constant current-based or constant voltage-based stimulation in the form of pulses or continuous waveforms. Delivery of stimulation via both a housing anode and one or more lead anodes, for example, may allow a user to control current paths between the housing electrode and the lead electrode(s) in a relative manner to achieve different electric stimulation field shapes.

A unipolar stimulation arrangement generally refers to the use of an anode on the housing that sources current and one or more cathodes on one or more leads that sink current. A bipolar stimulation arrangement generally refers to the use of an anode on a lead that sources current and a cathode on the same lead and/or another lead that sink current. A multipolar stimulation arrangement generally refers to the use of more than one anode on a lead that each source current and one or more cathodes on the same lead or another lead that sink current, or the use of one anode on a lead that sources current and multiple cathodes on the same lead or another lead that sink current.

A unipolar stimulation arrangement may offer some advantages over a bipolar stimulation arrangement. For instance, a unipolar stimulation arrangement may present less impedance than a bipolar stimulation arrangement and, as a result, may consume less power than a bipolar stimulation arrangement. In a bipolar stimulation arrangement using two leads, for example, electrical stimulation current sourced through an anode on one lead may return through a cathode on the other lead. As an illustration, if each lead has an impedance of about 200 ohms, a significant energy can be lost in the circuit due to impedance loading of the stimulation current. In contrast, in a unipolar arrangement, electrical stimulation current sourced through an anode on the can returns via a cathode on a 200 ohm lead after being transmitted through tissue. In some cases, the impedance of tissue is significantly lower than that of a lead. As such, less energy is lost in the unipolar stimulation arrangement.

However, in other instances, a bipolar stimulation arrangement may offer advantages over a unipolar stimulation arrangement. For instance, using a unipolar stimulation arrangement, the electric stimulation field created between the housing anode and the lead cathode may be shaped like a sphere as a result of the distance between the two (or more) electrodes. The stimulation provided to a patient by the large sphere-like stimulation field may be less desirable to a patient than other, more localized fields. For instance, the volume of tissue activation may be greater using a unipolar stimulation arrangement, which may result in additional, undesired, tissue being stimulated. In contrast, a bipolar stimulation arrangement, with the anodes and cathodes on one or more leads, may provide stimulation fields that are smaller and have more localized shapes (due to the close proximity between the anodes and cathodes on leads) than the sphere-like field created by a unipolar stimulation arrangement. A lead-based anode in proximity to a lead-based cathode may provide a shield-like effect that permits the generation of a more localized field that is concentrated on target tissue, avoiding activation of other tissue.

Techniques of this disclosure support combining attributes of both the unipolar stimulation arrangement and the bipolar stimulation arrangement to provide a hybrid arrangement that may be referred to as an omnipolar arrangement. By providing at least one housing anode and one or more anodes on one or more leads, and delivering electrical stimulation via the housing anode and the one or more anodes on the leads substantially simultaneously, in conjunction with one or more lead-based cathodes, the techniques of this disclosure may offer one or more advantages.

For example, an IMD using such a configuration may consume less power than a bipolar stimulation arrangement would alone, yet provide more flexibility relative to a unipolar arrangement in shaping a stimulation field created by the stimulation current delivered by the housing anode and the lead anode. In addition, these techniques may allow more precise steering, shaping or focusing of an electric field to transition between a unipolar stimulation arrangement to a bipolar stimulation arrangement. The user may select a balance between delivery of stimulation via a unipolar stimulation arrangement and delivery of stimulation via at least one lead anode.

In some cases, delivery of stimulation may be transitioned from unipolar to bipolar (or multipolar), using different weighted omnipolar combinations of unipolar vs. bipolar (or multipolar) until the user selects one of the omnipolar combinations, e.g., based on the user's perceived efficacy of the omnipolar combination. This transitioning feature may allow more flexibility in selecting the relative strengths of the stimulation delivered by anodes on the housing and the lead. In some cases, one or more anodes disposed on one or more leads near one or more cathodes carried by the leads may provide a shield effect that more effectively localizes, confines, or concentrates electrical stimulation in the vicinity of the cathodes. Different weighted combinations of stimulation delivered via housing and lead anodes can determine the shield strength.

This disclosure also describes techniques that support automatically balancing stimulation currents delivered by two or more user selected electrodes on one or more leads as described above by one or more non-user selected lead electrodes, or other electrodes located in the body, configured to deliver balancing current. It may be desirable for the balancing current to be delivered by sub-threshold electrodes, i.e., electrodes that deliver energy (e.g., current, voltage) at amplitude levels below a threshold at which stimulation can be perceived by a patient. It may be desirable to maintain a charge density of energy delivered by the sub-threshold electrodes at a lower level than a charge density of energy delivered at or above a threshold in which stimulation may be perceived by the patient. It may further or instead be desirable to deliver balancing energy via one or more electrodes distal from the two or more user selected electrodes.

As used throughout this disclosure, substantially simultaneous delivery of stimulation, whether current or voltage, refers to the partial or complete time-wise synchronization of the electrical stimulation pulses or waveforms. Complete time-wise synchronization may refer to the housing electrode, e.g., anode, delivering stimulation at the same time that one or more lead electrodes, e.g., anodes, deliver stimulation. For example, complete time-wise synchronization may include the rising edge of the stimulation pulse or waveform being delivered by the housing electrode, e.g., anode, substantially coinciding with the rising edge of the stimulation pulse or waveform being delivered by the one or more lead electrodes, e.g., anodes, and the falling edge of the stimulation pulse or waveform being delivered by the housing electrode, e.g., anode, coinciding with the falling edge of the stimulation pulse or waveform being delivered by the one or more lead electrodes, e.g., anodes. Complete time-wise synchronization may also include a pulse delivered by a housing anode, for example, being delivered within the pulse width of a pulse delivered by a lead anode, for example. Partial time-wise synchronization may refer to the housing electrode, e.g., anode, delivering one electrical stimulation pulse or waveform while at least one lead electrode, e.g., anode, is delivering another electrical stimulation pulse or waveform such that at least a portion of one of the rising or falling edge of one pulse or waveform overlaps in time with at least a portion of one of the rising or falling edge of at least one other pulse or waveform.

FIG. 1 is a conceptual diagram illustrating an example system 2 that may be used to deliver stimulation therapy to patient 6. Patient 6 ordinarily, but not necessarily, will be a human. Generally, therapy system 2 includes implantable stimulator 4 that delivers electrical stimulation to patient 6 via one or more implantable electrodes (not shown). The implantable electrodes may be deployed on one or more implantable medical leads, such as implantable medical lead 10, and in some cases on a can electrode. The electrical stimulation may be in the form of constant current or voltage pulses or substantially continuous waveforms. Various parameters of the pulses or waveforms may be defined by a stimulation program. The pulses or waveforms may be delivered substantially continuously or in bursts, segments, or patterns, and may be delivered alone or in combination with pulses or waveforms defined by one or more other stimulation programs. Although FIG. 1 shows a fully implantable stimulator 4, techniques described in this disclosure may be applied to external stimulators having electrodes deployed via percutaneously implantable leads. One or more of the electrodes may be located on a housing 14, i.e., "can" or "case," of the implantable stimulator 4. In addition, in some cases, implantable electrodes may be deployed on a leadless stimulator.

In the example illustrated in FIG. 1, implantable stimulator 4 is implanted within a subcutaneous pocket in a clavicle region of patient 6. Stimulator 4 generates programmable electrical stimulation, e.g., a current waveform or current pulses, and delivers the stimulation via an implantable medical lead 10 carrying an array of implantable stimulation electrodes 11. In some cases, multiple implantable leads may be provided. In the example of FIG. 1, a distal end of lead 10 is bifurcated and includes two lead segments 12A and 12B (collectively "lead segments 12"). Lead segments 12A and 12B each include a set of electrodes forming part of the array of electrodes 11. In various examples, lead segments 12A and 12B may each carry four, eight, or sixteen electrodes. In FIG. 1, each lead segment 12A, 12B carries four electrodes, configured as ring electrodes at different axial positions near the distal ends of the lead segments. Throughout the remainder of this disclosure, for purposes of simplicity, the disclosure may generally refer to electrodes carried on "leads" rather than "lead segments."

FIG. 1 further depicts a housing, or can, electrode 13 carried by housing 14. Housing electrode 13 may be formed integrally with an outer surface of hermetically-sealed housing 14 of implantable stimulator 4, also referred to in this disclosure as implantable medical device (IMD) 4, or otherwise coupled to housing 14. In one example, housing electrode 13 may be described as an active, non-detachable electrode on the surface of the IMD. In some examples, housing electrode 13 is defined by an uninsulated portion of an outward facing portion of housing 14 of IMD 4. Other divisions between insulated and uninsulated portions of housing 14 may be employed to define two or more housing electrodes, which may be referred to as case or can electrodes. In some examples, housing electrode 13 comprises substantially all of housing 14, one side of housing 14, a portion of the housing 14, or multiple portions of housing 14. In other examples, housing electrode 13 may be formed integrally with header 8. For example, header 8 may comprise a conductive surface that functions as housing electrode 13. In example configurations in which header 8 functions as housing electrode 13, all of header 8 may comprise a conductive surface, a portion of header 8 may comprise a conductive surface, or multiple portions of header 8 may comprise conductive surfaces. In one example implementation of the techniques of this disclosure, e.g., an omnipolar arrangement, one or more electrodes 11 may transfer stimulation pulses from the lead 10 to the tissue substantially simultaneously with stimulation pulses delivered via housing electrode 13.

In some examples, lead 10 may also carry one or more sense electrodes to permit implantable stimulator 4 to sense electrical signals from patient 6. Some of the stimulation electrodes may be coupled to function as stimulation electrodes and sense electrodes on a selective basis. In other examples, implantable stimulator 4 may be coupled to one or more leads which may or may not be bifurcated. In such examples, the leads may be coupled to implantable stimulator 4 via a common lead extension or via separate lead extensions.

A proximal end of lead 10 may be both electrically and mechanically coupled to header 8 on implantable stimulator 4 either directly or indirectly via a lead extension. Conductors in the lead body may electrically connect stimulation electrodes located on lead segments 12 to implantable stimulator 4. Lead 10 traverses from the implant site of implantable stimulator 4 along the neck of patient 6 to cranium 18 of patient 6 to access brain 16. Lead segments 12A and 12B are implanted within the right and left hemispheres, respectively, in order to deliver electrical stimulation to one more regions of brain 16, which may be selected based on the patient condition or disorder.

Implantable stimulator 4 may deliver, for example, deep brain stimulation (DBS) or cortical stimulation (CS) therapy to patient 6 via the electrodes carried by, i.e., located on, lead segments 12 to treat any of a variety of neurological disorders or diseases. Example neurological disorders may include depression, dementia, obsessive-compulsive disorder and movement disorders, such as Parkinson's disease, spasticity, epilepsy, and dystonia. DBS also may be useful for treating other patient conditions, such as migraines and obesity. However, the disclosure is not limited to the configuration of lead 10 shown in FIG. 1, or to the delivery of DBS or CS therapy.

Lead segments 12A, 12B may be implanted within a desired location of brain 16 through respective holes in cranium 18. Lead segments 12A, 12B may be placed at any location within brain 16 such that the electrodes located on lead segments 12A, 12B are capable of providing electrical stimulation to targeted tissue during treatment. Example locations for lead segments 12A, 12B within brain 26 may include the pedunculopontine nucleus (PPN), thalamus, basal ganglia structures (e.g., globus pallidus, substantia nigra, subthalmic nucleus), zona inserta, fiber tracts, lenticular fasciculus (and branches thereof), ansa lenticularis, and/or the Field of Forel (thalamic fasciculus). In the case of migraines, lead segments 12 may be implanted to provide stimulation to the visual cortex of brain 16 in order to reduce or eliminate migraine headaches afflicting patient 6. However, the target therapy delivery site may depend upon the patient condition or disorder being treated.

The electrodes of lead segments 12A, 12B are shown as ring electrodes. Ring electrodes are commonly used in DBS applications because they are simple to program and are capable of delivering an electrical field to any tissue adjacent to lead segments 12A, 12B. In other implementations, the electrodes of lead segments 12A, 12B may have different configurations. For example, the electrodes of lead segments 12A, 12B may have a complex electrode array geometry that is capable of producing shaped electrical fields. The complex electrode array geometry may include multiple electrodes (e.g., partial ring or segmented electrodes) around the perimeter of each lead segments 12A, 12B, rather than one ring electrode. In this manner, electrical stimulation may be directed in a specific direction from lead segments 12 to enhance therapy efficacy and reduce possible adverse side effects from stimulating a large volume of tissue. In alternative examples, lead segments 12 may have shapes other than elongated cylinders as shown in FIG. 1. For example, lead segments 12 may be paddle leads, spherical leads, bendable leads, or any other type of shape effective in treating patient 6.

Therapy system 2 also may include a clinician programmer 20 and/or a patient programmer 22. Clinician programmer 20 may be a handheld computing device that permits a clinician to program stimulation therapy for patient 6 via a user interface, e.g., using input keys and a display. For example, using clinician programmer 20, the clinician may specify stimulation parameters, i.e., create programs, for use in delivery of stimulation therapy. Clinician programmer 20 may support telemetry (e.g., radio frequency (RF) telemetry) with implantable stimulator 4 to download programs and, optionally, upload operational or physiological data stored by implantable stimulator 4. In this manner, the clinician may periodically interrogate implantable stimulator 4 to evaluate efficacy and, if necessary, modify the programs or create new programs. In some examples, clinician programmer 20 transmits programs to patient programmer 22 in addition to or instead of implantable stimulator 4.

Like clinician programmer 20, patient programmer 22 may be a handheld computing device. Patient programmer 22 may also include a display and input keys to allow patient 6 to interact with patient programmer 22 and implantable stimulator 4. In this manner, patient programmer 22 provides patient 6 with a user interface for control of the stimulation therapy delivered by implantable stimulator 4. For example, patient 6 may use patient programmer 22 to start, stop or adjust electrical stimulation therapy. In particular, patient programmer 22 may permit patient 6 to adjust stimulation parameters of a program such as duration, current or voltage amplitude, pulse width and pulse rate. Patient 6 may also select a program, e.g., from among a plurality of stored programs, as the present program to control delivery of stimulation by implantable stimulator 4.

In some examples, implantable stimulator 4 delivers stimulation according to a group of programs at a given time. Each program of such a program group may include respective values for each of a plurality of therapy parameters, such as respective values for each of current or voltage amplitude, pulse width, pulse shape, pulse rate and electrode configuration (e.g., electrode combination and polarity). Implantable stimulator 4 may interleave pulses or other signals according to the different programs of a program group, e.g., cycle through the programs, to simultaneously treat different symptoms or different body regions, or provide a combined therapeutic effect. In such examples, clinician programmer 20 may be used to create programs, and assemble the programs into program groups. Patient programmer 22 may be used to adjust stimulation parameters of one or more programs of a program group, and select a program group, e.g., from among a plurality of stored program groups, as the current program group to control delivery of stimulation by implantable stimulator 4.

Implantable stimulator 4, clinician programmer 20, and patient programmer 22 may communicate via cables or a wireless communication, as shown in FIG. 1. Clinician programmer 20 and patient programmer 22 may, for example, communicate via wireless communication with implantable stimulator 4 using RF telemetry techniques known in the art. Clinician programmer 20 and patient programmer 22 also may communicate with each other using any of a variety of local wireless communication techniques, such as RF communication according to the 802.11 or Bluetooth specification sets, infrared communication, e.g., according to the IrDA standard, or other standard or proprietary telemetry protocols. Each of clinician programmer 20 and patient programmer 22 may include a transceiver to permit bi-directional communication with implantable stimulator 4.

Generally, system 2 delivers stimulation therapy to patient 6 in the form of constant current or voltage waveforms or constant current or voltage pulses. The shapes of the pulses may vary according to different design objectives. In the case of current-based stimulation, implantable stimulator 4 regulates current that is sourced or sunk by one or more electrodes, referred to as regulated electrodes. In some examples, one of the electrodes may be unregulated. In such configurations, either the housing electrode or a lead electrode may be the unregulated electrode.

A source current, i.e, an anodal current, may refer to a positive current, i.e., a current having a positive polarity, that flows out of an electrode, e.g., from a regulated current source via a regulated current path to surrounding tissue, or from a reference voltage via an unregulated current path. A sink current, i.e, a cathodal current, may refer to a negative current, i.e., a current having a negative polarity, that flows into an electrode, e.g. from surrounding tissue and is sunk by a regulated current sink via a regulated current path or by a reference voltage via an unregulated current path. Regulated source currents may sum to produce a greater overall source current. Regulated sink currents may sum to produce a greater overall sink current. Regulated source and regulated sink currents may partially or entirely cancel one another, producing a net difference in the form of a net source current or sink current in the case of partial cancellation. An unregulated current path can source or sink current approximately equal to this net difference.

As mentioned above, using the techniques of this disclosure, one or more electrodes 11 may transfer stimulation pulses from the lead 10 to the tissue substantially simultaneously with stimulation pulses delivered via housing electrode 13. For example, housing electrode 13 and one or more electrodes 11 may be configured to act as anodes and source current. Substantially simultaneously delivering stimulation via both a housing anode and one or more lead anodes may allow a user to achieve different electric field shapes by controlling current paths between the housing anode and the lead anode(s) in a relative manner.

Figure 2:
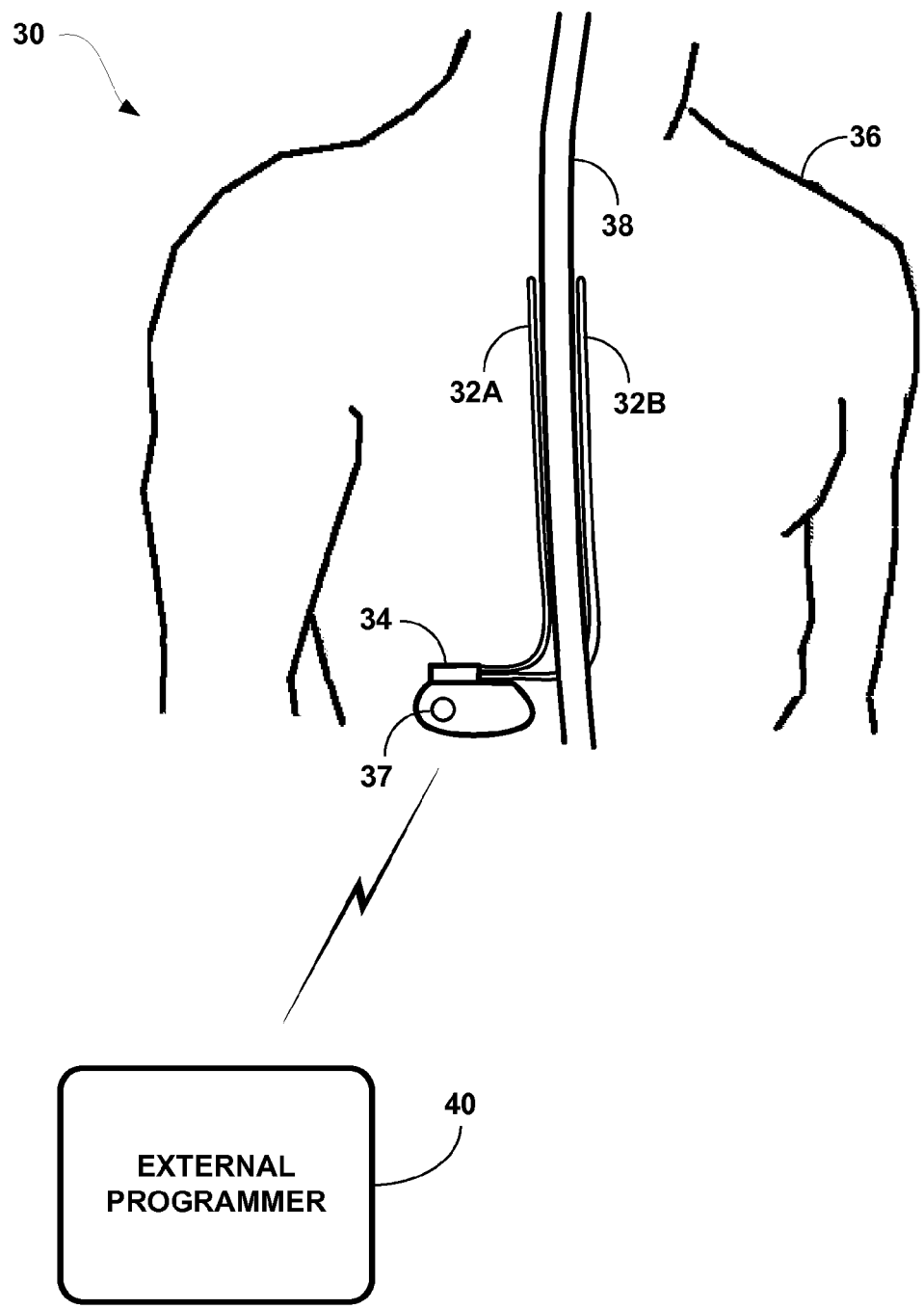
FIG. 2 is a conceptual diagram illustrating another example therapy system that includes an implantable stimulator coupled to a stimulation lead.

FIG. 2 is a conceptual diagram illustrating system 30 that delivers stimulation therapy to spinal cord 38 of patient 36. Hence, like FIG. 1, FIG. 2 represents another example of an electrical stimulation system that may support omnipolar stimulation techniques described in this disclosure. Other electrical stimulation systems may be configured to deliver electrical stimulation to gastrointestinal organs, pelvic nerves or muscle, peripheral nerves, or other stimulation sites. In the example of FIG. 2, system 30 delivers stimulation therapy from implantable stimulator 34 to spinal cord 38 via one or more electrodes (not shown) carried by, i.e., located on, implantable medical leads 32A and 32B (collectively "leads 32") as well as the housing of implantable stimulator 34, e.g., housing electrode 37. System 30 and, more particularly, implantable stimulator 34 may operate in a manner similar to implantable stimulator 4 (FIG. 1). That is, in a current-based example, implantable stimulator 34 delivers controlled current stimulation pulses or waveforms to patient 36 via one or more regulated, stimulation electrodes. Alternatively, implantable stimulator 34 may be configured to deliver constant voltage pulses. As mentioned above, in some examples, one of the electrodes may be unregulated.

In the example of FIG. 2, the distal ends of leads 32 carry electrodes that are placed adjacent to the target tissue of spinal cord 38. The proximal ends of leads 32 may be both electrically and mechanically coupled to implantable stimulator 4 either directly or indirectly via a lead extension and header. Alternatively, in some examples, leads 32 may be implanted and coupled to an external stimulator, e.g., through a percutaneous port. In additional example implementations, stimulator 34 may be a leadless stimulator with one or more arrays of electrodes arranged on a housing of the stimulator rather than leads that extend from the housing. Application of certain techniques will be described in this disclosure with respect to implantable stimulator 34 and implantable leads 32 having ring electrodes for purposes of illustration. However, other types of electrodes may be used.

Stimulator 34 may be implanted in patient 36 at a location minimally noticeable to the patient. For SCS, stimulator 34 may be located in the lower abdomen, lower back, or other location to secure the stimulator. Leads 32 are tunneled from stimulator 34 through tissue to reach the target tissue adjacent to spinal cord 38 for stimulation delivery. At the distal ends of leads 32 are one or more electrodes (not shown) that transfer the stimulation pulses from the lead to the tissue substantially simultaneously with stimulation pulses delivered via a housing electrode, e.g., electrode 37. Some of the electrodes may be electrode pads on a paddle lead, circular (i.e., ring) electrodes surrounding the body of leads 32, conformable electrodes, cuff electrodes, segmented electrodes, or any other type of electrodes capable of forming unipolar, bipolar or multi-polar electrode configurations.

Implantable stimulator 34 delivers stimulation to spinal cord 38 to reduce the amount of pain perceived by patient 36. As mentioned above, however, the stimulator may be used with a variety of different therapies, such as peripheral nerve stimulation (PNS), peripheral nerve field stimulation (PNFS), deep brain stimulation (DBS), cortical stimulation (CS), pelvic floor stimulation, peripheral nerve stimulation, gastric stimulation, and the like. The stimulation delivered by implantable stimulator 34 may take the form of stimulation pulses or continuous stimulation waveforms, and may be characterized by controlled current or voltage levels, as well as programmed pulse widths and pulse rates in the case of stimulation current pulses. Stimulation may be delivered via selected combinations of electrodes located on one or both of leads 32 and on the housing. Stimulation of spinal cord 38 may, for example, prevent pain signals from traveling through the spinal cord and to the brain of the patient. Patient 34 perceives the interruption of pain signals as a reduction in pain and, therefore, efficacious therapy.

With reference to FIG. 2, a user, such as a clinician or patient 36, may interact with a user interface of external programmer 40 to program stimulator 34. Programming of stimulator 34 may refer generally to the generation and transfer of commands, programs, or other information to control the operation of the stimulator. For example, programmer 40 may transmit programs, parameter adjustments, program selections, group selections, or other information to control the operation of stimulator 34, e.g., by wireless telemetry.

In some cases, external programmer 40 may be characterized as a physician or clinician programmer, such as clinician programmer 20 (FIG. 1), if it is primarily intended for use by a physician or clinician. In other cases, external programmer 40 may be characterized as a patient programmer, such as patient programmer 22 (FIG. 1), if it is primarily intended for use by a patient. In general, a physician or clinician programmer may support selection and generation of programs by a clinician for use by stimulator 34, whereas a patient programmer may support adjustment and selection of such programs by a patient during ordinary use.

Whether programmer 40 is configured for clinician or patient use, programmer 40 may communicate to implantable stimulator 4 or any other computing device via wireless communication. Programmer 40, for example, may communicate via wireless communication with implantable stimulator 4 using radio frequency (RF) telemetry techniques known in the art. Programmer 40 may also communicate with another programmer or computing device via a wired or wireless connection using any of a variety of local wireless communication techniques, such as RF communication according to the 802.11 or Bluetooth specification sets, infrared communication according to the IRDA specification set, or other standard or proprietary telemetry protocols. Programmer 40 may also communicate with another programming or computing device via exchange of removable media, such as magnetic or optical disks, or memory cards or sticks. Further, programmer 40 may communicate with implantable stimulator 4 and other programming devices via remote telemetry techniques known in the art, communicating via a local area network (LAN), wide area network (WAN), public switched telephone network (PSTN), or cellular telephone network, for example.

Figure 3:
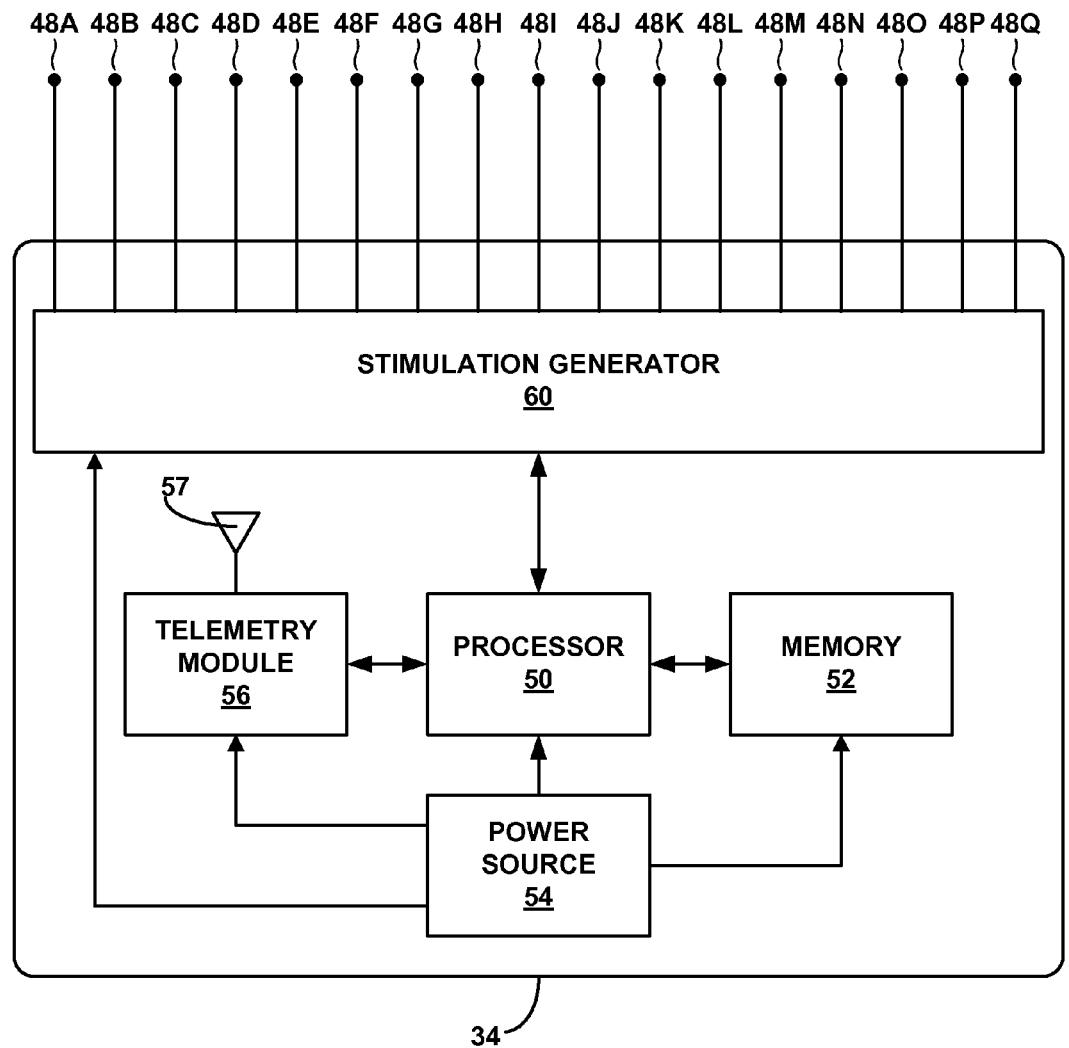
FIG. 3 is a block diagram illustrating various example components of an implantable electrical stimulator.

FIG. 3 is a block diagram illustrating various components of an example implantable stimulator 34. Although the components shown in FIG. 3 are described in reference to implantable stimulator 34, the components may also be included within implantable stimulator 4 shown in FIG. 1 and used within system 2. In the example of FIG. 3, implantable stimulator 34 includes processor 50, memory 52, power source 54, telemetry module 56, antenna 57, and a stimulation generator 60. Implantable stimulator 34 is also shown in FIG. 3 coupled to electrodes 48A-Q (collectively "electrodes 48"). Electrodes 48A-48P are implantable and may be deployed on one or more implantable leads. With respect to FIG. 1, lead segments 12A and 12B may carry electrodes 48A-H and electrodes 48I-P, respectively. In some cases, one or more additional electrodes may be located on or within the housing of implantable stimulator 34, e.g., to provide a common or ground electrode or a housing anode. With respect to FIG. 2, leads 32A and 32B may carry electrodes 48A-H and electrodes 48I-P, respectively. In the examples of FIGS. 1 and 2, a lead or lead segment carries eight electrodes to provide an 2×8 electrode configuration (two leads with 8 electrodes each), providing a total of sixteen different electrodes. The leads may be detachable from a housing associated with implantable stimulator 34, or be fixed to such a housing.

In other examples, different electrode configurations comprising a single lead, two leads, three leads, or more may be provided. In addition, electrode counts on leads may vary and may be the same or different from a lead to lead. Examples of other configurations include one lead with eight electrodes (1×8), one lead with 12 electrodes (1×12), one lead with 16 electrodes (1×16), two leads with four electrodes each (2×4), three leads with four electrodes each (3×4), three leads with eight electrodes each (3×8), three leads with four, eight, and four electrodes, respectively (4-8-4), two leads with 12 or 16 electrodes (2×12, 2×16), or other configurations. Different electrodes are selected to form electrode combinations. Polarities are assigned to the selected electrodes to form electrode configurations.

Electrode 48Q represents one or more electrodes that may be carried on a housing, i.e., can, of implantable stimulator 4. Electrode 48Q may be configured as a regulated or unregulated electrode for use in an electrode configuration with selected regulated and/or unregulated electrodes among electrodes 48A-48P, which may be located on a lead body of one or more leads, as described above. Electrode 48Q may be formed together on a housing that carries the electrode and houses the components of implantable stimulator 4, such as stimulation generator 60, processor 50, memory 52, telemetry module 56, and power source 54.

In accordance with this disclosure, housing electrode 48Q may be configured for use as an anode to source current substantially simultaneously with current sourced by another electrode 48A-48P configured for use as an anode. By way of specific example, electrodes 48A, 48B, and housing electrode 48Q each could be configured for use as anodes. Electrodes 48A, 48B could deliver electrical stimulation current substantially simultaneously with the electrical stimulation current delivered via housing electrode 48Q. In this illustration, one or more cathodes could be formed with other electrodes (e.g., any of electrodes 48C-48P) on the leads to sink current sourced by anodes 48A, 48B and 48Q.

In further accordance with this disclosure, housing electrode 48Q may be configured for use as a cathode to sink current substantially simultaneously with current sunk by another electrode 48A-48P configured for use as a cathode. By way of specific example, electrodes 48A, 48B, and housing electrode 48Q each could be configured for use as cathodes. Electrodes 48A, 48B could deliver electrical stimulation current substantially simultaneously with the electrical stimulation current delivered via housing electrode 48Q. In this illustration, one or more anodes could be formed with other electrodes (e.g., any of electrodes 48C-48P) on the leads to source current sunk by cathodes 48A, 48B and 48Q.

As used throughout this disclosure, the phrase "delivering electrical stimulation current" may refer to delivery of a source current by an electrode that sources current (anode), e.g., from a reference voltage for an unregulated mode or from a regulated current source for a regulated mode, or to delivery of a sink current by an electrode that sinks current (cathode), e.g., to a reference voltage for an unregulated mode or to a regulated current sink for a regulated mode. In other words, "delivering" as used in this disclosure is directionless in that "delivering" may refer to current flowing into or out of the electrode. So, an electrode configured as anode may deliver electrical stimulation current having a first polarity, i.e., a positive polarity, and an electrode configured as a cathode may also deliver electrical stimulation current having a second polarity, i.e., a negative polarity.

Memory 52 may store instructions for execution by processor 50, stimulation therapy data, sensor data, and/or other information regarding therapy for patient 6. Processor 50 may control stimulation generator 60 to deliver stimulation according to a selected one or more of a plurality of programs or program groups stored in memory 52. Memory 52 may include any electronic data storage media, such as random access memory (RAM), read-only memory (ROM), electronically-erasable programmable ROM (EEPROM), flash memory, or the like. Memory 52 may store program instructions that, when executed by processor 50, cause the processor to perform various functions ascribed to processor 50 and implantable stimulator 4 in this disclosure.

Processor 50 may include one or more microprocessors, digital signal processors (DSPs), application-specific integrated circuits (ASICs), field-programmable gate arrays (FPGAs), or other digital logic circuitry. Processor 50 controls operation of implantable stimulator 4, e.g., controls stimulation generator 60 to deliver stimulation therapy according to a selected program or group of programs retrieved from memory 52. For example, processor 50 may control stimulation generator 60 to deliver electrical signals, e.g., as stimulation pulses or continuous waveforms, with current amplitudes, pulse widths (if applicable), and rates specified by one or more stimulation programs. Processor 50 may also control stimulation generator 60 to selectively deliver the stimulation via subsets of electrodes 48, also referred to as electrode combinations, and with polarities specified by one or more programs.

Upon selection of a particular program group, processor 50 may control stimulation generator 60 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate, if applicable. For a continuous waveform, parameters may include amplitude and frequency. In addition, each program may specify a particular electrode combination for delivery of stimulation, and an electrode configuration in terms of the polarities and regulated/unregulated status of the electrodes. The electrode combination may specify particular electrodes in a single array or multiple arrays, and on a single lead or among multiple leads. In accordance with this disclosure, the electrode combination includes at least one anode on the housing of the IMD, e.g., electrode 48Q, at least one anode on a lead, electrode 48A, and at least one cathode on a lead. The lead-borne anode and cathode may be on the same lead or different leads, if more than one lead is provided.

Stimulation generator 60 is electrically coupled to electrodes 48A-P via conductors of the respective lead, such as lead 12 in FIG. 1 or leads 32 in FIG. 2, in implementations in which electrodes 48A-P are carried by, located on, leads. Stimulation generator 60 may be electrically coupled to one or more housing ("can") electrodes 48Q via an electrical conductor disposed within the housing of implantable stimulator 4 (FIG. 1) or implantable stimulator 34 (FIG. 3). A housing electrode 48Q may be configured as a regulated or unregulated electrode to form an electrode configuration in conjunction with one or more of electrodes 48A-48P located on leads of the IMD. In accordance with this disclosure, housing electrode 48Q may be configured for use as an anode to source current substantially simultaneously with one or more electrodes, e.g., any of electrodes 48A-48P, on one or more leads configured for use as anodes.

Stimulation generator 60 may include stimulation generation circuitry to generate stimulation pulses or waveforms and circuitry for switching stimulation across different electrode combinations, e.g., in response to control by processor 50. Stimulation generator 60 produces an electrical stimulation signal in accordance with a program based on control signals from processor 50.

For example, stimulation generator 60 may include a charging circuit that selectively applies energy from power source 54 to a capacitor module for generation and delivery of a supply voltage for generation of stimulation signal. In addition to capacitors, the capacitor module may include switches. In this manner, the capacitor module may be configurable, e.g., based on signals from processor 50, to store a desired voltage for delivery of stimulation at a voltage or current amplitude specified by a program. For delivery of stimulation pulses, switches within the capacitor module may control the widths of the pulses based on signals from processor 50.

In accordance with techniques of this disclosure, stimulation generator 60 may be configured to deliver stimulation using one or more of electrodes 48A-P as stimulation electrodes, e.g., anodes, while substantially simultaneously delivering stimulation using housing electrode 48Q as a stimulation electrode, e.g., anode. The anodes on the lead(s) and the housing may be used to deliver stimulation in conjunction with one or more cathodes on the lead(s). As one illustration, an electrode combination selected for delivery of stimulation current may comprise an anode on the IMD housing, and anode on a lead, and a cathode on the same lead or a different lead. In other examples, the electrode combination may include multiple anodes and/or multiple cathodes on one or more leads in conjunction with at least one anode on the IMD housing. In each case, the electrode combination forms an omnipolar arrangement that may combine at least some characteristics and benefits of unipolar and bipolar/multipolar arrangements.

Telemetry module 56 may include a radio frequency (RF) transceiver to permit bi-directional communication between implantable stimulator 4 and each of clinician programmer 20 and patient programmer 22. Telemetry module 56 may include an antenna 57 that may take on a variety of forms. For example, antenna 57 may be formed by a conductive coil or wire embedded in a housing associated with medical device 4. Alternatively, antenna 57 may be mounted on a circuit board carrying other components of implantable stimulator 4 or take the form of a circuit trace on the circuit board. In this way, telemetry module 56 may permit communication with clinician programmer 20 and patient programmer 22 in FIG. 1 or external programmer 40 in FIG. 2, to receive, for example, new programs or program groups, or adjustments to programs or program groups.

Power source 54 may be a non-rechargeable primary cell battery or a rechargeable battery and may be coupled to power circuitry. However, the disclosure is not limited to embodiments in which the power source is a battery. In another embodiment, as an example, power source 54 may comprise a supercapacitor. In some embodiments, power source 54 may be rechargeable via induction or ultrasonic energy transmission, and include an appropriate circuit for recovering transcutaneously received energy. For example, power source 54 may be coupled to a secondary coil and a rectifier circuit for inductive energy transfer. In additional embodiments, power source 54 may include a small rechargeable circuit and a power generation circuit to produce the operating power. Recharging may be accomplished through proximal inductive interaction between an external charger and an inductive charging coil within stimulator 4. In some embodiments, power requirements may be small enough to allow stimulator 4 to utilize patient motion at least in part and implement a kinetic energy-scavenging device to trickle charge a rechargeable battery. A voltage regulator may generate one or more regulated voltages using the battery power.

Figure 4:
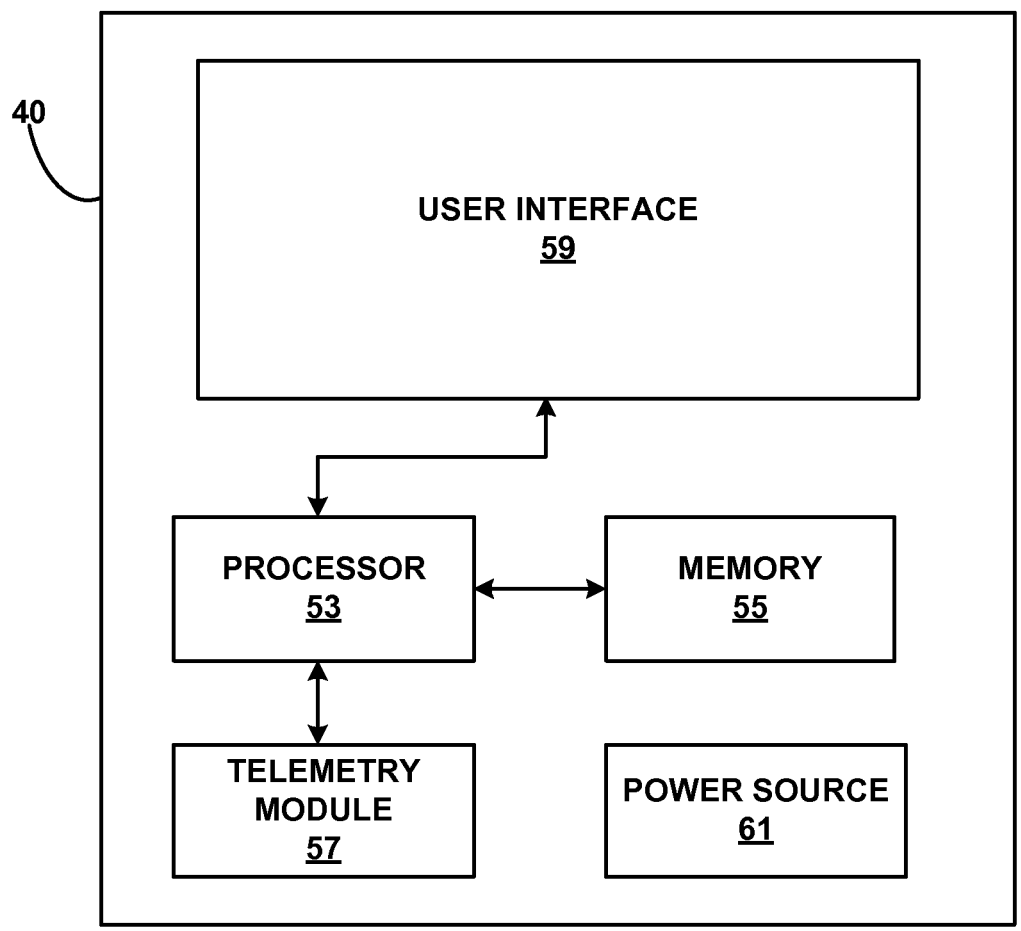
FIG. 4 is a block diagram illustrating various example components of an external programmer for use with an electrical stimulator.

FIG. 4 is a functional block diagram illustrating various components of an external programmer 40 for an implantable stimulator 14. Although the components shown in FIG. 4 are described in reference to external programmer 40, the components may also be included within clinician programmer 20 or patient programmer 22 shown in FIG. 1. As shown in FIG. 4, external programmer 40 includes processor 53, memory 55, telemetry module 57, user interface 59, and power source 61. In general, processor 53 controls user interface 59, stores and retrieves data to and from memory 55, and controls transmission of data with implantable stimulator 34 through telemetry module 57. Processor 53 may take the form of one or more microprocessors, controllers, DSPs, ASICS, FPGAs, or equivalent discrete or integrated logic circuitry. The functions attributed to processor 53 herein may be embodied as software, firmware, hardware or any combination thereof.

Memory 55 may store instructions that cause processor 53 to provide various aspects of the functionality ascribed to external programmer 40 in this disclosure. Memory 55 may include any fixed or removable magnetic, optical, or electrical media, such as RAM, ROM, CD-ROM, magnetic disks, EEPROM, or the like. Memory 55 may also include a removable memory portion that may be used to provide memory updates or increases in memory capacities. A removable memory may also allow patient data to be easily transferred to another computing device, or to be removed before programmer 40 is used to program therapy for another patient. Memory 55 may also store information that controls operation of implantable stimulator 4, such as therapy delivery values.

A clinician or patient 36 interacts with user interface 59 in order to, for example, manually select, change or modify programs, adjust voltage or current amplitude, provide efficacy feedback, or view stimulation data. User interface 59 may include a screen and one or more input buttons that allow external programmer 40 to receive input from a user. The screen may be a liquid crystal display (LCD), plasma display, dot matrix display, or touch screen. The input buttons may include a touch pad, increase and decrease buttons, emergency shut off button, and other input media needed to control the stimulation therapy.

Telemetry module 57 allows the transfer of data to and from stimulator 34. Telemetry module 57 may communicate automatically with stimulator 34 at a scheduled time or when the telemetry module detects the proximity of the stimulator. Alternatively, telemetry module 57 may communicate with stimulator 34 when signaled by a user through user interface 59. To support RF communication, telemetry module 44 may include appropriate electronic components, such as amplifiers, filters, mixers, encoders, decoders, and the like.

Programmer 40 may communicate wirelessly with implantable stimulator 34 using, for example, RF communication or proximal inductive interaction. This wireless communication is possible through the use of telemetry module 44 which may be coupled to an internal antenna or an external antenna. Telemetry module 44 may be similar to telemetry module 57 of implantable stimulator 34.

Programmer 40 may also be configured to communicate with another computing device via wireless communication techniques, or direct communication through a wired, e.g., network, connection. Examples of local wireless communication techniques that may be employed to facilitate communication between programmer 24 and another computing device include RF communication based on the 802.11 or Bluetooth specification sets, infrared communication, e.g., based on the IrDA standard.

Power source 46 delivers operating power to the components of programmer 40. Power source 46 may be a rechargeable battery, such as a lithium ion or nickel metal hydride battery. Other rechargeable or conventional batteries may also be used. In some cases, external programmer 40 may be used when coupled to an alternating current (AC) outlet, i.e., AC line power, either directly or via an AC/DC adapter. Power source 61 may include circuitry to monitor power remaining within a battery. In this manner, user interface 59 may provide a current battery level indicator or low battery level indicator when the battery needs to be replaced or recharged. In some cases, power source 61 may be capable of estimating the remaining time of operation using the current battery.

Figure 5:
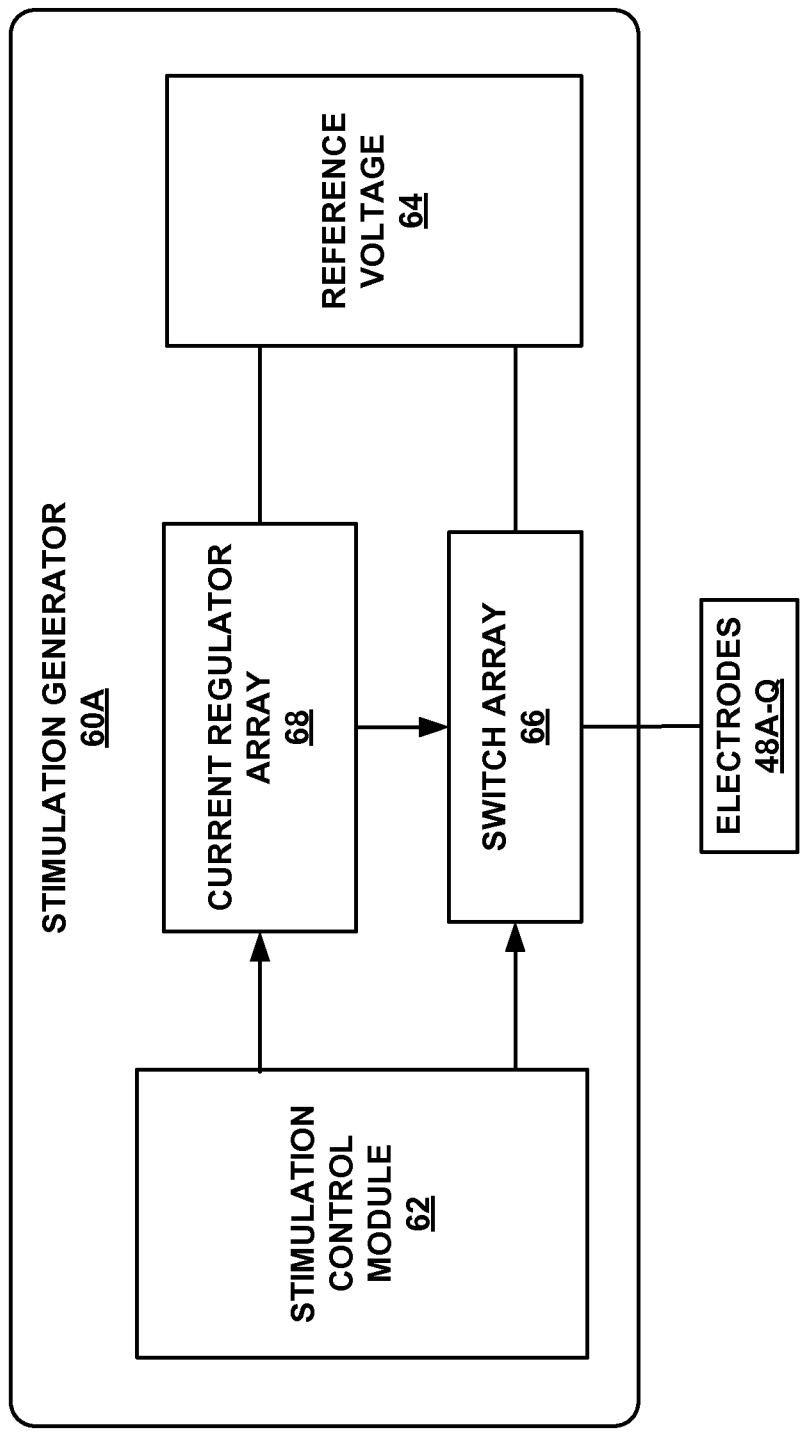
FIG. 5 is a block diagram illustrating various components of an example electrical stimulation generator for use in the implantable electrical stimulator of FIG. 3.

FIG. 5 is a block diagram illustrating various components of an example stimulation generator 60A. Stimulation generator 60A may be used with an implantable stimulator, e.g., to perform the functions of stimulation generator 60 as described with reference to FIGS. 1-3. Although described with respect to implantable stimulator 4, stimulation generator 60A may also be used for implantable stimulator 34, or other types of stimulators. In the example of FIG. 5, stimulation generator 60A is selectively, e.g., based on a signal from processor 50 (FIG. 3), configured to deliver constant current stimulation pulses to patient 6 via various electrode combinations. However, the disclosure is not limited to examples in which regulated current pulses are delivered. In other examples, stimulation generator 60A may provide continuous, regulated current waveforms, rather than regulated current pulses. In still other examples, stimulation generator 60A may deliver combinations of continuous waveforms and pulses, or selectively deliver either continuous waveforms or pulses. Stimulation generator 60A may generate either constant current-based or constant voltage-based stimulation in the form of pulses or continuous waveforms.

In the example illustrated in FIG. 5, stimulation generator 60A includes stimulation control module 62, reference voltage source 64, switch array 66, and current regulator array 68. Reference voltage source 64 may provide operating power to current regulator array 68, and may include a regulated voltage that sets the level of the reference voltage. As shown in FIG. 5, reference voltage source 64 may be coupled to provide operating power for the current regulator array 68 and provide a reference voltage for connection to electrodes 48A-48Q for an unregulated mode of electrode operation. In other examples, however, the voltage level of the reference voltage and the operating voltage level provided to regulated current source array 68 may be different.

Stimulation control module 62 forms a stimulation controller that controls switch array 66 and current regulator array 68 to deliver stimulation via electrodes 48A-48Q. Stimulation control module 62 may include one or more microprocessors, microcontrollers, digital signal processors (DSPs), application-specific integrated circuits (ASICs), field-programmable gate arrays (FPGAs), or other integrated or discrete logic circuitry. In operation, stimulation control module 62 may control delivery of electrical stimulation according to one or more programs that may specify stimulation parameters such as electrode combination, electrode polarity, stimulation current amplitude, pulse rate, and/or pulse width as well as the percentage of source current distributed among or contributed by a housing anode and one or more lead anodes on one or more leads, and the percentage of sink current sunk by one or more cathodes. Programs may be defined by a user via an external controller and downloaded to an implantable stimulator 4 or 34 for use by stimulation control module 62.

Current regulator array 68 includes a plurality of regulated current sources or sinks. Again, a current regulator may function as either a current source or sink, or be selectively configured to operate as either a source or a sink. For convenience, however, the term "current regulator" may be used in some instances to refer to either a source or sink. Hence, each of the current regulators in current regulator array 68 may operate as a regulated current source that delivers stimulation via a corresponding one of electrodes 48A-Q or a regulated current sink that receives current from a corresponding one of electrodes 48A-Q, where electrodes 48A-48Q may be provided on leads, on a stimulator housing, on a leadless stimulator, or in other arrangements. In general, electrodes 48A-48Q may be referred to below as electrodes 48 for conciseness.

Each switch of switch array 66 couples a corresponding one of electrodes 48 to either a corresponding bidirectional current regulator of current regulator array 68 or to reference voltage 64. In some examples, stimulation control module 62 selectively opens and closes switches in switch array 66 to configure a housing electrode, e.g., electrode 48Q, and one or more of electrodes 48A-48P on one or more leads as regulated electrodes by connection to regulated current sources or sinks in current regulator array 68. In other examples, stimulation control module 62 may selectively open and close switches in switch array 66 to configure either the housing electrode, e.g., electrode 48Q, or an electrode on the lead as an unregulated electrode by connection to reference voltage 64. In addition, stimulation control module 62 may selectively control individual regulated current sources or sinks in current regulator array 68 to deliver stimulation current pulses to the selected electrodes.

Reference voltage 64 may be a high or low voltage supplied by a regulated power source, depending on whether an electrode is programmed to be an unregulated source (high voltage rail) or unregulated sink (low voltage rail). Hence, reference voltage 64 may produce high and low reference voltages for selective coupling to unregulated, reference electrodes as needed given the selected electrode configuration. A regulated power source may produce one or more regulated voltage levels for use as reference voltage 64 and for use as a power rail for current regulator array 68. Again, although the same reference voltage 64 is coupled to current regulator array 68 in FIG. 5, different voltage levels could be used for the reference voltage coupled to switch array 66 and the operating voltage level provided to the regulated current source array. A regulated power source may generate the regulated voltages from voltages provided by a power source 54 (FIG. 3), such as a battery.

Stimulation control module 62 controls the operation of switch array 66 to produce electrode configurations defined by different stimulation programs. In some cases, the switches of switch array 66 may be metal-oxide-semiconductor field-effect-transistors (MOSFETs) or other circuit components used for switching electronic signals. The switches of switch array 66 may be designed to carry an amount of unregulated current that may be coupled to a corresponding electrode through an unregulated current path associated with reference voltage 64. As previously described, two or more regulated, stimulation electrodes 48 may be intentionally programmed to deliver different amounts of current such that the regulated electrodes produce an unbalanced current distribution.

To provide individual control of electrodes 48 as either regulated electrodes or as unregulated, reference electrodes, stimulation control module 62 controls operation of switch array 66, and current regulator array 68. When stimulation is delivered to patient 6, for the example of current pulses, stimulation control module 62 controls switch array 66 to couple selected stimulation electrodes for a desired electrode combination to respective current regulators of current regulator array 68 or to reference voltage 64, as needed. Stimulation control module 62 controls the regulated bidirectional current sources of current regulator array 68 coupled to regulated electrodes to source or sink specified amounts of current. For example, stimulation control module 62 may control selected current sources or sinks to on a pulse-by-pulse basis to deliver current pulses to corresponding electrodes.

Stimulation control module 62 also deactivates the regulated bidirectional current regulators of current regulator array 68 tied to inactive electrodes, i.e., electrodes that are not active as regulated electrodes in a given electrode configuration. Each regulated bidirectional current regulator of current regulator array 68 may include an internal enable switch controlled by stimulation control module 62 that disconnects regulated power source 64 from the current regulator or otherwise disables the current source when the corresponding electrode is not used as a regulated electrode to deliver stimulation.

Figure 6:
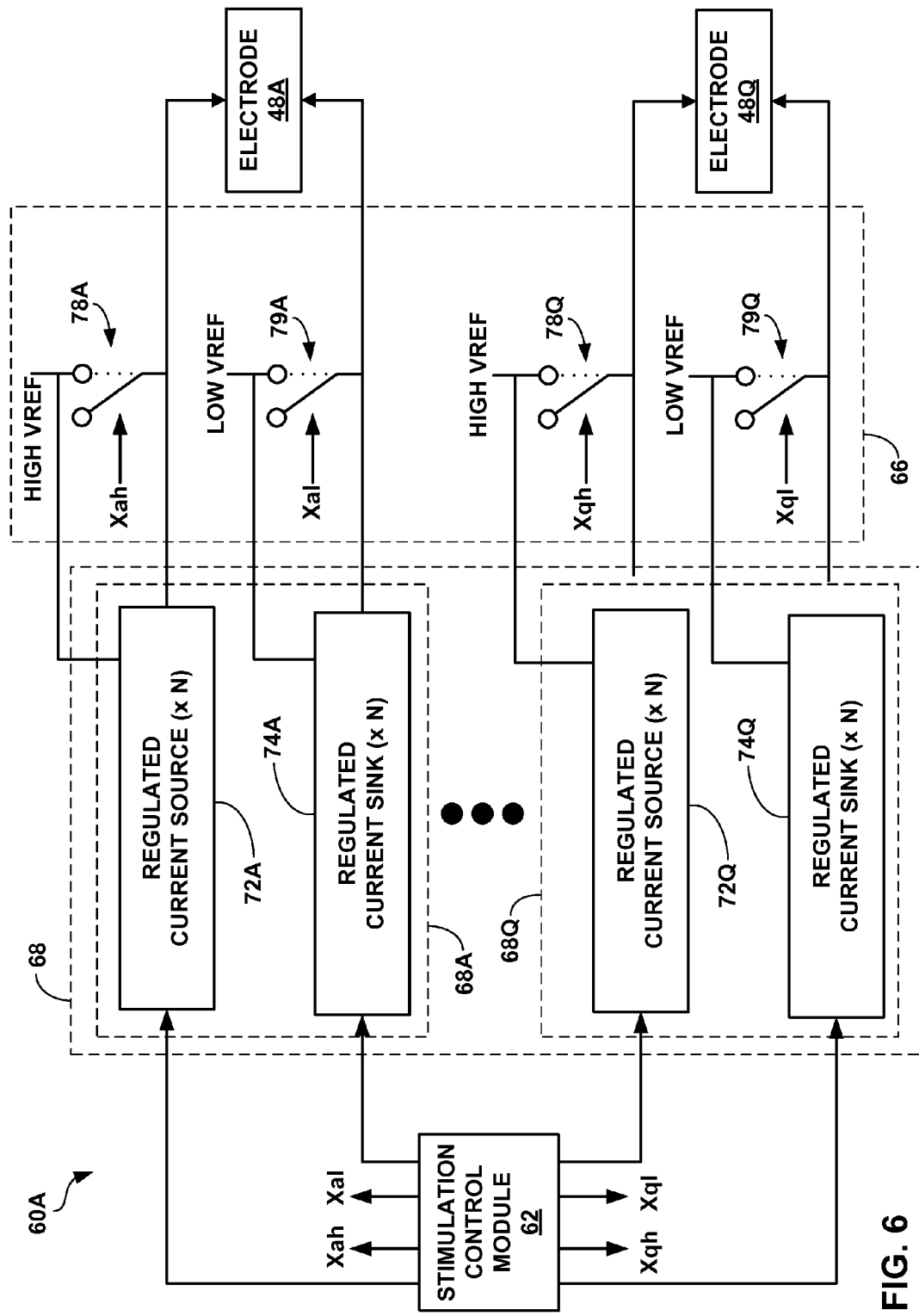
FIG. 6 is a block diagram illustrating the example stimulation generator of FIG. 5 in greater detail.

FIG. 6 is a block diagram illustrating an example of various components of stimulation generator 60A shown in FIG. 5 in greater detail. In particular, FIG. 6 shows current regulator array 68 and switch array 66 in greater detail. As shown in FIG. 6, current regulator array 68 includes regulated bidirectional current regulators 68A-Q and switch array 66 includes switches 78A-78Q and 79A-79Q. Each of bidirectional current regulators 68A-68Q includes a corresponding one of regulated current sources 72A-72Q that delivers regulated stimulation current to the corresponding electrode and a corresponding one of regulated current sinks 74A-74Q that receives regulated stimulation current from the corresponding electrode. Note that the block diagram illustrated in FIG. 6 is intended as a conceptual diagram that shows how stimulation generator 60A can be configured to control the operation of electrodes 48 in different modes, i.e., an off mode, regulated modes, and an unregulated, reference mode. Thus, for ease of illustration, not all power and control signals are shown in FIG. 6.

In the example of FIG. 6, switches 78A-78Q may be coupled at one end to a high voltage reference, which may correspond to a high reference voltage level of reference voltage 64, and to a corresponding one of electrodes 48 at the other end. Switches 79A-79Q may be coupled at one end to a low voltage reference, which may correspond to low reference voltage level of reference voltage 64, and to a corresponding one of electrodes 48 at the other end. High reference voltage (High Vref) and low reference voltage (Low Vref) represent high and low voltage levels of reference voltage 64 (FIG. 5) and may be supplied by power source 54. For example, the high reference voltage may correspond to a reference voltage level and the low reference voltage may correspond to a ground potential to which the reference voltage level is referenced.

As further shown in FIG. 6, each regulated current source 72A-72Q may be coupled to the high reference voltage or another upper voltage rail, which supports regulator overhead and sources current that is regulated by the regulated current source. In addition, each regulated current sink 74A-74Q may be coupled to the low reference voltage or another lower voltage rail or ground potential, which supports regulator overhead and sinks current that is regulated by the regulated current sink.

Stimulation control module 62 controls the operation of regulated current sources 72A-72Q, sinks 74A-74Q, switches 78A-78Q, and switches 79A-79Q to configure electrodes 48A-48Q as either inactive (i.e., off), regulated cathodes, regulated anodes, unregulated cathodes or unregulated anodes. For example, stimulation control module 62 may generate control signals to individually control regulated current sources 72A-72Q to deliver specified amounts of regulated current to electrodes 48A-48Q, respectively, and thereby configure such electrodes as regulated anodes. Similarly, stimulation control module 62 may generate control signals to individually control regulated current sinks 74A-74Q to receive specified amounts of regulated currents from electrodes 48A-48Q, respectively, and thereby configure such electrodes as regulated cathodes. For example, stimulation control module 62 may enable the current sources or sinks and also specify control voltages or current to be applied to the source or sinks to control the amount of current that is sourced or sunk via the respective electrodes 48A-48Q.

Using the techniques of this disclosure, at least one electrode on the housing, e.g., electrode 48Q, and one or more electrodes on one or more leads, e.g., one or more of electrodes 48A-48P, may be configured as anodes. In this manner, the housing electrode and one or more lead electrodes may substantially simultaneously deliver current to a patient as anodes. One or more cathodes may be activated on one or more leads to receive the stimulation energy, e.g., sink the current, produced by the anodes on the can and lead(s). For example, as one illustration, electrode 48A may be an electrode on a lead and be configured as an anode to source current, electrode 48M may also be an electrode on lead and be configured as a cathode to sink current, and electrode 48Q may be an electrode on the housing and be configured as an anode to source current.

By way of specific example, stimulation control module 62 may generate a control signal to close switch 78A, thereby coupling lead electrode 48A to regulated current source 72A, thus configuring lead electrode 48A as a regulated anode. Stimulation control module 62 may then generate a control signal to close switch 78Q, thereby coupling housing electrode 48Q to regulated current source 72Q, thus configuring housing electrode 48Q as a regulated anode. Stimulation control module 62 may also configure lead electrode 48M (not shown in FIG. 6) as a regulated cathode by generating a control signal to close switch 79M (not shown in FIG. 6), thereby coupling lead electrode 48M to regulated current sink 74M. Regulated current sink 74M receives specified amounts of regulated currents from electrodes 48A and 48Q. Once configured in this manner, processor 50 may control stimulation generator 60 to deliver stimulation according to a selected one or more of a plurality of programs or program groups stored in memory 52 such that stimulation is delivered substantially simultaneously by both lead electrode 48A and housing electrode 48Q, and received by lead electrode 48M.

It should be noted that additional lead electrodes may also be configured as anodes and additional lead electrodes may be configured as cathodes. In one specific example, lead electrodes 48B and 48C may also be configured as regulated anodes, and lead electrode 48P may be configured as a regulated cathode. In this manner, there may be a plurality of lead electrodes configured as anodes delivering electrical stimulation substantially simultaneously with the electrical stimulation delivered by a housing electrode configured as an anode, and a plurality of lead electrodes configured as cathodes receiving the combined electrical stimulation from the lead electrodes and the housing electrode.

In addition, stimulation control module 62 may generate control signals to control switches 78A-78Q and 79A-79Q to selectively couple electrodes 48A-48Q to the high reference voltage or the low reference voltage, respectively. For example, stimulation control module 62 may generate control signals Xah-Xqh to close switches 78A-78Q, respectively, and couple electrodes 48A-48Q to the high reference voltage. In this manner, one of electrodes 48A-48Q may be selectively configured as unregulated, reference anodes that source current from the high reference voltage. Similarly, stimulation control module 62 may generate control signals Xal-Xql to close switches 79A-79Q, respectively, and couple electrodes 48A-48Q to the low reference voltage.

In an example implementation, each current regulator, in the form of either regulated current source 72A-72Q or regulated current sink 74A-74Q, may be implemented as a plurality of regulated current sources and sinks, respectively, operating in parallel to produce a combined, programmable current level sufficient for a desired stimulation therapy. A regulated current source 72A, for example, may be implemented by several parallel current sources (x N) having identical or similar structures. Similarly, a regulated current sink may be implemented by several parallel current sinks (x N) having identical or similar structures. For example, in accordance with this disclosure, regulated current source 72Q may be implemented by several parallel current sources (x N) having identical or similar structures in order to produce a combined, programmable current level for a desired stimulation therapy delivered via housing electrode 48Q substantially simultaneously with one or more regulated current sources 72A-72P coupled to one or more lead electrodes 48A-48P. In this manner, stimulation therapy may be delivered by a combination of electrodes including both the housing electrode 48Q and one or more lead electrodes 48A-48P. It should be noted that in such a configuration, the one or more regulated current sources 72A-72P may also be implemented by several parallel current sources (x N) having identical or similar structures in order to produce a combined, programmable current level for a desired stimulation therapy.

Similarly, a regulated current sink 74A may be implemented as N parallel, regulated current sinks, each sinking a fraction of a total regulated to be sunk by electrode 48A. By activating a selected number of the parallel, regulated current sources forming a regulated current source 72A, stimulation control module 62 may control an amount of regulated source current delivered to a given electrode 48A coupled to the respective current source. Similarly, by activating a selected number of parallel, regulated current sink branches forming a regulated current sink 74A, stimulation control module 62 may control an amount of regulated sink current delivered from a given electrode 48A coupled to the respective current sink.

As an example, each current regulator, e.g., regulated source 72A-72Q or regulated sink 74A-74Q, may be implemented by N parallel current regulator branches. As an example, N may be equal to 64 in some implementations. In this type of implementation, stimulation control module 62 may specify a reference source current and a reference sink current, e.g., based on program data specified automatically or by a user via an external programmer. For each electrode, stimulation control module 62 may further specify a percentage of the reference source current or reference sink current to be delivered via the electrode, e.g., based on program data. For example, stimulation control module 62 may specify that housing electrode 48Q should source 60% of the current to be delivered as an anode while lead electrodes 48A, 48B substantially simultaneously source 15% and 25%, respectively, of the current to be delivered as anodes. Stimulation control module 62 may also specify that lead electrode 48D should sink 100% of the current as a cathode.

A control signal may be applied to each parallel current regulator branch such that the current levels produced by all N branches will add up to approximately the reference current level. Based on the percentage, which may be referred to as a gain ratio, stimulation control module 62 may selectively activate or deactivate a number of parallel current regulator branches for a given electrode sufficient to produce the specified percentage of the reference current. In this manner, stimulation control module 62 selectively scales up or scales down the number of active, parallel current regulator branches. If the reference current is 20 milliamps (mA), for example, the control signal is selected such that activation of all N parallel current regulator branches would produce 20 mA of source current or sink current, as applicable, for application via an electrode. In this case, the control signal may be selected such that each current regulator branch produces $1/N^{th}$ of the reference current.

If the percentage to be delivered by a given electrode, e.g., housing electrode 48Q, is 50 percent, then stimulation control module 62 activates 50 percent of the N parallel current regulator branches or, conversely, deactivates 50 percent of the N parallel current regulator branches. In either case, N/2 parallel current regulator branches are activated, producing a combined current of 50%×20 mA=10 mA to be sourced by electrode 48Q in this example. Hence, when activated, each current regulator may source or sink a finite amount of current, determined as a function of the control signal, such that the fractional currents flowing in the parallel regulator branches can be summed to produce an overall regulated current. If the reference current is changed, the applicable control signal applied to each current regulator branch is changed. In the example above, a lead electrode 48A-48P sources, alone or in combination with the remaining lead electrodes 48A-48P, the remaining 50%×20 mA=10 mA of current, substantially simultaneously with the 10 mA sourced by housing electrode 48Q.

By specifying percentages of source current and sink current for respective electrodes, stimulation control module 62 can control current regulators 72A-72Q and 74A-74Q to precisely and selectively control the current level sourced by housing electrode 48Q and the current level sourced substantially simultaneously by one or more lead electrodes 48A-48P. In addition, the current levels sunk by particular electrodes 48A-48Q may also be precisely and selectively control. Further, stimulation control module 62 can support effective steering of stimulation current to create different electrical stimulation fields or patterns useful in electrical stimulation therapy.

Using regulated current source 72A and electrode 48A as an example, the outputs of the parallel current source branches forming the regulated current source are coupled to electrode 48A such that the electrode receives a sum of the regulated source currents produced by the multiple, parallel current source branches. A similar arrangement can be provided for current sinks 74A-74Q. Hence, the description of a single source or sink and the representation of a single source or sink in FIG. 6 are provided for purposes of illustration, and may represent either a single source or sink or multiple, parallel sources or sinks configured as described in this disclosure. Likewise, each switch 78A-78Q, 79A-79Q may be implemented by a single switch, or by multiple, parallel switches operating to support a sum of the multiple, fractional currents sourced or sunk via each parallel switch.

When turned "ON," each parallel current source or sink branch may produce a known amount of current, defined by the reference current and corresponding control signal, as described above. In this manner, a source or sink may be considered either ON or OFF, and deliver the same fractional amount of current as other sources or sinks whenever it is ON. Alternatively, in some embodiments, each parallel current source or sink could be configured to provide different fractional amounts of current, or deliver variable amounts of current according to a bias signal. Although it is understood that each given source 72A-72Q or sink 74A-74Q may include multiple, parallel source branches or sink branches, and that a given switch 78A-78Q or 79A-79Q may include multiple, parallel switches, this disclosure will generally refer to each of sources 72A-72Q, sinks 74A-74Q, or switches 78A-78Q, 79A-79Q on a singular basis for ease of illustration.

Figure 7:
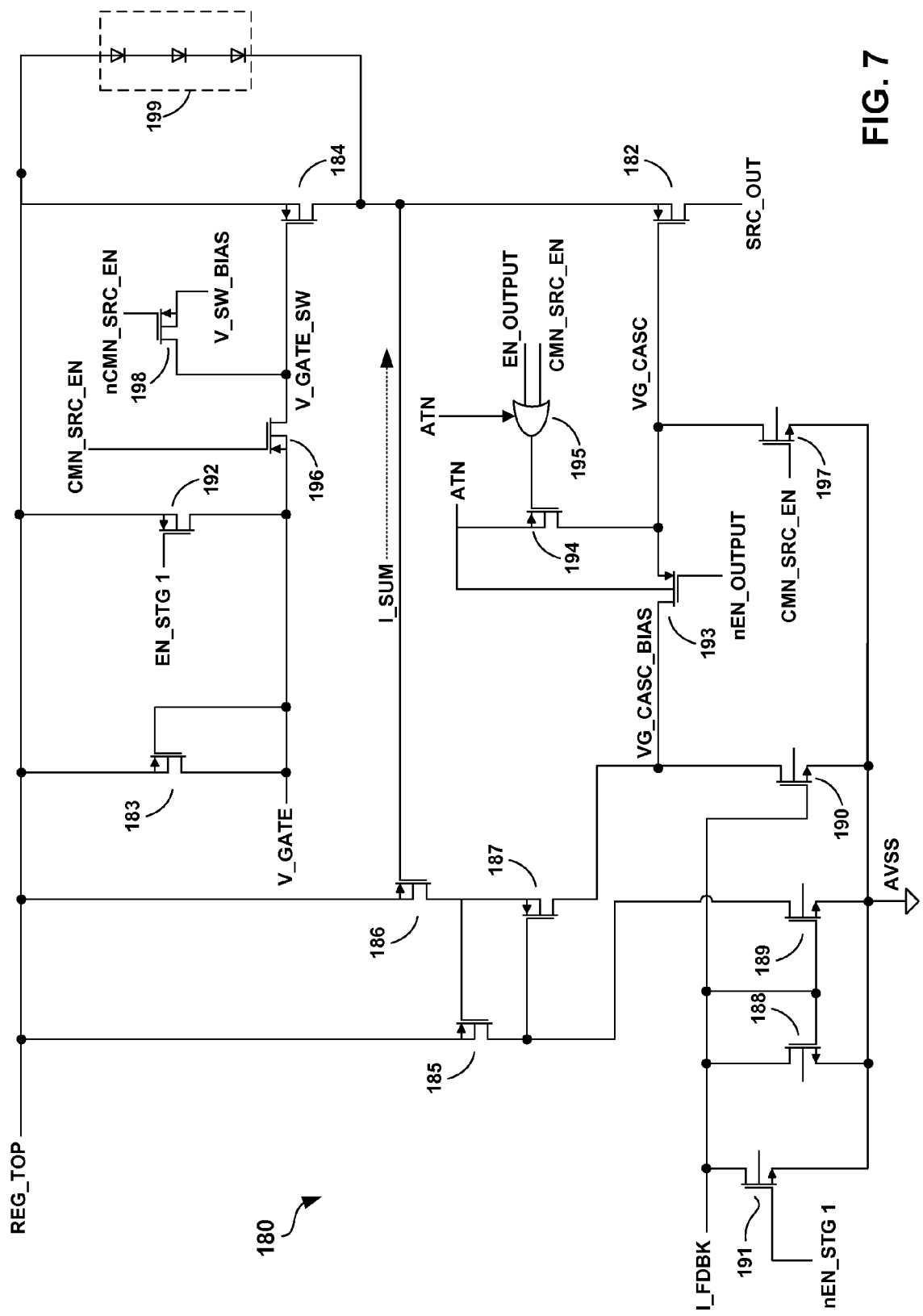
FIGS. 7 and 8 are circuit diagrams illustrating example circuitry for use in the stimulator generator shown in FIG. 5.

FIG. 7 is a circuit diagram illustrating an example circuit 180 that may be used to implement stimulation generator 60A as shown in FIG. 5. In the example of FIG. 7, transistors 182-198 are configured and arranged to operate as an adaptable current source. Diodes 199 operate to protect transistor 184 from high voltages in the event of leakage current from transistor 182. For circuit 180 of FIG. 7, the adaptable current source may represent a number of parallel, adaptable current regulator branches that are selectively activated to scale up or down to a desired current level as a percentage of a reference current. Circuit 180 shows one of these branches. Each regulated current source may include 64 parallel current regulator branches, each providing $1/64^{th}$ of the reference current level. Additional information regarding, for example, adaptable current sources may be found in U.S. patent application Ser. No. 12/579,220, filed Oct. 14, 2009, entitled "Adaptable Current Regulator For Delivery Of Current-Based Electrical Stimulation Therapy," the entire contents of which being incorporated herein by reference.

The inputs to the example circuit 180 are REG_TOP, ATN, V_GATE, I_FDBK, EN_STG1, V_SW_BIAS, nEN_STG1, EN_OUTPUT, CMN_SRC_EN, nCMN_SRC_EN, as well as AVSS, and nEN_OUTPUT. REG_TOP, ATN, and AVSS are supply inputs that drive the elements of circuit 180. V_GATE and I_FDBK are control inputs that drive various components of circuit 180. EN_STG1, nEN_STG1, EN_OUTPUT, nEN_OUTPUT, CMN_SRC_EN, and nCMN_SRC_EN are logic inputs that are used to control the operation of circuit 180 as a regulator or as a switch that couples a corresponding electrode to unregulated high reference voltage, e.g., REG_TOP.

Some of these inputs are used to turn circuit 180 off when the corresponding electrode is not in use. Accordingly, transistors 191-198 are used as switches for controlling the mode of operation of circuit 180. Transistors 191 and 192 may function as enable switches used to turn master transistors 188, 183, respectively, OFF and ON. Transistors 193 and 196 may function as isolation switches to isolate transistors 182, 184 from a front end of the circuit. Transistors 197 and 198 may function as reference switches that bias transistors 182, 184, respectively, during unregulated operation. The isolation and reference transistors may be operated in a coordinated manner to selectively operate the adaptable current source as a regulated current source or as a switch that couples the corresponding electrode to a reference voltage via an unregulated current path. In particular, isolation transistors 193, 196 and reference transistors 197, 198 may function to selectively tie transistors 182, 184 into the current mirror and activate cascode circuitry for regulated current delivery, or separate transistors 182, 184 from such circuitry for unregulated current delivery from REG_TOP. The output of circuit 180 is SRC_OUT and is applied to a corresponding electrode.

AVSS may be a controlled low voltage supply that remains substantially constant and may be provided by a regulated power source. ATN may be a high voltage supply rail that remains substantially constant and may provide a higher voltage potential than REG_TOP or AVSS. V_GATE is an analog input signal supplied by stimulation control module 62 when circuit 180 is operating as a current regulator. The V_GATE signal may be generated as a function of a reference current specified for each regulated current source.

If all N parallel branches are operating, the V_GATE signal will cause the voltage regulator to produce a combined current level that is approximately equal to the reference current level. Again, a percentage assigned to each active electrode may be used to scale up or scale down the number of active parallel, adaptable regulator branches in a given current regulator to produce a desired fractional current level. Stimulation control module 62 may not supply V_GATE to circuit 180 when circuit 180 is operating as a switch or is not used for delivering stimulation.

The following description refers to the operation of circuit 180 in an adaptable manner as either a current regulator or a switch.

Control signals EN_STG1, CMN_SRC_EN, nCMN_SRC_EN, nEN_STG1, and nEN_OUTPUT control transistors 192, 196 and 197, 198, 191, and 193, respectively. Or gate 195 applies a control signal to transistor 194 based on the levels of EN_OUTPUT and CMN_SRC_EN. These control signals are applied to the gates of the corresponding transistors to turn the transistors OFF and ON as described.

When operating as a current regulator, transistors 191, 192, 197, and 198 do not conduct, i.e., are not enabled. Transistor 183 acts as a master that controls the operation of slave transistor 184 by controlling V_GATE_SW. Thus, transistors 183 and 184 may be viewed as a master transistor and a slave transistor, respectively, in a current mirror arrangement. V_GATE_SW turns transistor 184 ON and OFF to produce a regulated current output signal with a desired current level controlled by the level of the V_GATE signal.

Example circuit 180 uses a configuration incorporating a current mirror and active cascode to operate as a current regulator. Transistors 183 and 184 form a current mirror, as mentioned above, and may be selected to be well matched to each other. Transistors 182 and 185-190 form an active cascode configuration that that protects transistor 184 from high voltages at SRC_OUT and monitors I_SUM so that the $V_{DS}$ of transistors 183 and 184 are approximately equal over the operational range of circuit 180.

In operation, REG_TOP decreases when delivering stimulation, thereby causing the voltage drop over transistors 182 and 184 to decrease proportionately. Because of this decrease, the $V_{DS}$ of transistor 182 decreases, causing transistor 186 to begin to turn OFF. This, in turn, causes the $V_{GS}$ of transistor 185 to increase and turn transistor 185 ON more, thereby decreasing the $V_{GS}$ of transistor 187. Consequently, transistor 187 begins to turn OFF, which causes the $V_{GS}$ of transistor 182 to increase. That is, transistor 187 replaces voltage on transistor 182, VG_CASC, causing its resistive value to decrease, thereby restoring voltage on drain-to-source voltage ($V_{DS}$) of transistor 184 so that it more closely matches the $V_{DS}$ of transistor 183.

Transistors 188-190 set the current for transistors 185-187 based on I_FDBK. I_FDBK is a reference current and may be generated by circuitry at a front end of example circuit 180. In particular, transistors 188 and 189 set the current for transistor 185 and transistor 190 sets the current for transistor 187.

Again, in FIG. 7, transistor 182 may represent multiple, e.g., sixty-four (64), transistors coupled in parallel with each other that each receive VG_CASC on their respective gates. As an example, the output of transistor 182 may be approximately 100 µA, but the overall source current may be many times that value, as a result of summation of multiple, parallel regulated current branches. In addition, transistor 182 also may prevent high voltages from being applied to the output.

When circuit 180 switches from operating as a current regulator to a switch, transistors 191 and 192 are turned ON, and transistors 193 and 196 are turned OFF. Transistors 197 and 198 remain turned OFF. After transistors 193 and 196 are turned OFF for a period of time, transistors 197 and 198 are turned ON. This creates a non-overlapping clock generator which prevents the supply voltage from shorting through transistors 191, 193, and 197. Gate 195 controls transistor 194 to be off during regulated or unregulated modes. When either of the inputs (EN_OUTPUT or CMN_SRC_EN) to gate 195 is high, the output of gate 195 is high, which turns off transistor 194, allowing the input to transistor 182 to be either driven low to ground via transistor 197 (causing transistor 182 to be driving as a switch in the unregulated mode) or to VG_CASC_BIAS via transistor 193 (as in the regulated mode). In some implementations, the signals EN_OUTPUT applied to gate 195 and nEN_OUTPUT applied to transistor 193 may be skewed in time slightly to implement a non-overlapping clock generator. In general, the signal nEN_OUTPUT is essentially the inverse of EN_OUTPUT except for the slight timing skew in some implementations.

In the unregulated mode, transistors 197 and 198 are turned ON to drive transistors 182 and 184, respectively, into saturation. Accordingly, SRC_OUT is coupled to the high reference voltage REG_TOP through transistors 182 and 184 and circuit 180 sources current based on the amount of current required to be delivered by the stimulation electrode given load conditions and current distribution at the stimulated tissue site adjacent the electrode. In this manner, circuit 180 can be configured to operate as either an unregulated current path or a regulated current path.

Circuit 180 is turned OFF when the corresponding electrode is inactive, i.e., not used in an electrode configuration for delivering stimulation therapy. Transistors 191, 192, 193, 194, and 196 are turned ON and transistors 197 and 198 are turned OFF when circuit 180 is turned OFF. When transistors 191 and 192 are turned ON, the active cascode (transistors 185-190) and transistor 183 are turned OFF.

Transistors 182-198 may be implemented as N-type and P-type MOSFET transistors configured to operate in a depletion mode. It should be understood, however, that circuit 180 may be implemented using various types and configurations of transistors.

Figure 8:
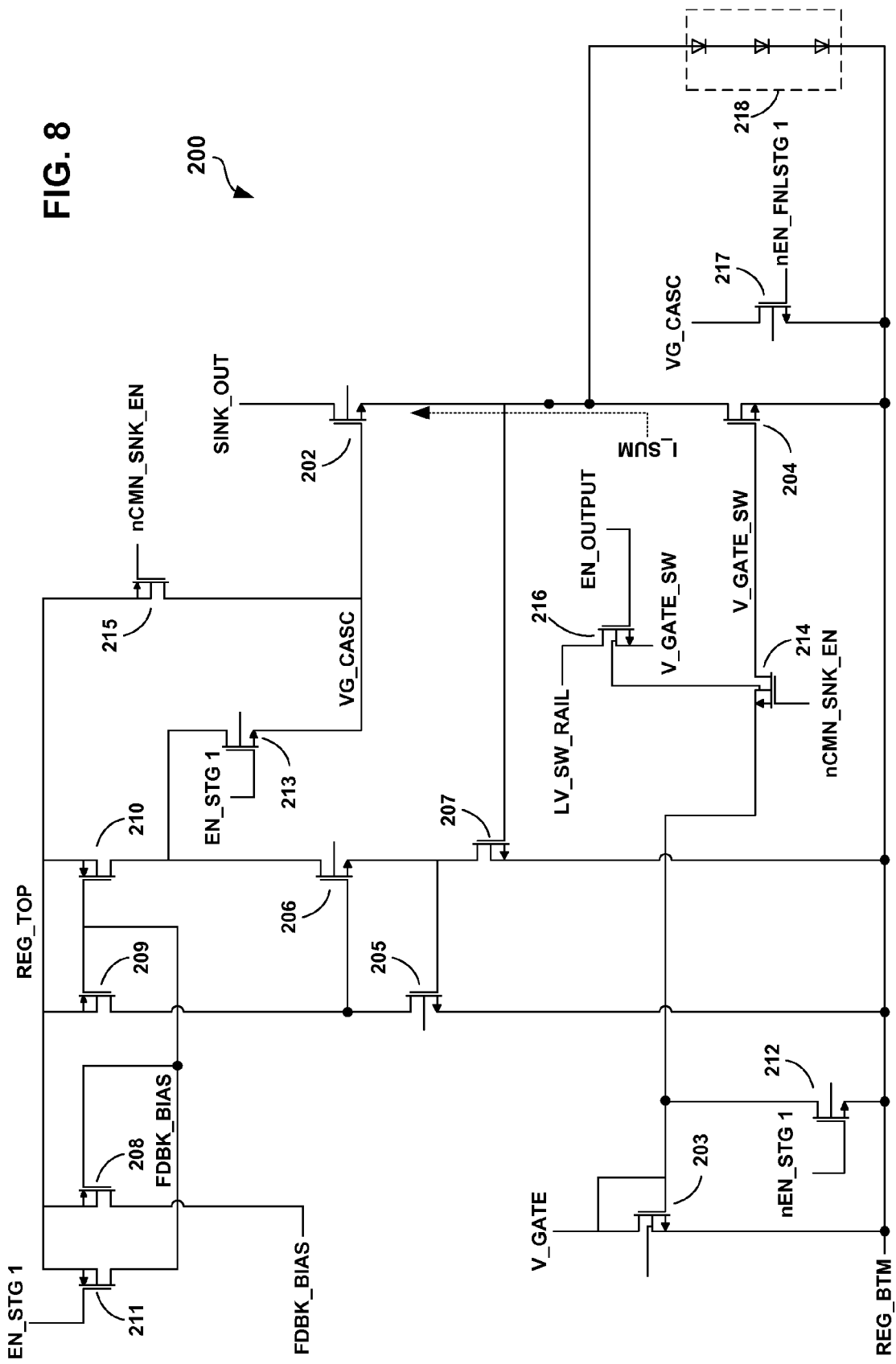

FIG. 8 is a circuit diagram illustrating an example circuit 200 that may be used to implement stimulation generator 60A as shown in FIG. 5. Example circuit 200 depicts an adaptable, regulated current sink. Inputs to circuit 200 are REG_TOP, REG_BTM, V_GATE, FDBK_BIAS, EN_STG1, nEN_STG1, and CMN_SNK_EN, and VG_CASC, as well as BPLUS, nCMN_SNK_EN, and nEN_OUTPUT. REG_TOP, REG_BTM, V_GATE, FDBK_BIAS, and LV_SW_RAIL are supply inputs that drive elements of circuit 200. EN_STG1, nEN_STG1, CMN_SNK_EN, nCMN_SNK_EN, and nEN_OUTPUT are logic inputs that are used to control the operation of circuit 200 as a current regulator or as a switch that couples a corresponding electrode to an unregulated low reference voltage, e.g., REG_BTM.

The logic inputs are also used to turn circuit 200 OFF when the corresponding electrode is not in use. Accordingly, transistors 211 and 212 may function as enable switches used to turn master transistors 208, 203, respectively, OFF and ON. Transistors 213 and 214 may function like isolation switches to selectively isolate transistors 202, 204 from the front end of the sink circuit. Transistors 215 and 216 may function as reference switches that bias transistors 202, 204 during unregulated mode. The isolation transistors 213, 214 and reference transistors 215, 216 may be operated in a coordinated manner to selectively operate the adaptable current sink as a regulated current sink or as a switch that couples the corresponding electrode to a reference voltage via an unregulated current path. In particular, isolation transistors 213, 214 and reference transistors 215, 216 may function to selectively tie transistors 202, 204 into the current mirror and activate cascode circuitry for regulated current delivery, or separate transistors 203, 204 from such circuitry for unregulated current delivery from REG_BTM. The output of circuit 200 is SNK_OUT and is applied to a corresponding electrode.

REG_TOP and REG_BTM are positive and negative voltages supplied as reference voltages. V_GATE is an analog input signal with desired stimulation parameters supplied by stimulation control module 62 when circuit 200 operates as a current regulator. Stimulation control module 62 may not supply V_GATE to circuit 200 when circuit 200 is operating as a switch or is not in use. In some examples, REG_BTM need not be a negative voltage and may instead by a ground or other reference voltage.

The following provides a description of the operation of circuit 200 as a current regulator and as a switch. When operating as a current regulator and, more specifically, as a regulated current sink, transistors 211, 212, 215, and 216 are turned OFF and transistors 213 and 214 are turned ON. In this configuration, transistor 203 controls the operation of transistor 204 by controlling the gate voltage of transistor 204, V_GATE_SW. This turns transistor 204 ON and OFF to produce a regulated current output signal with the desired signal parameters set by input signal V_GATE. Consequently, transistors 203 and 204 may be viewed as a master transistor and a slave transistor, respectively.

To operate as a regulated current sink, example circuit 200 uses a configuration that includes a current mirror with well matched transistors and a plurality of transistors operating as an active cascode configuration. Transistors 203 and 204 may be configured to operate as a current mirror and selected to be well matched to each other, and transistors 202 and 205-210 may operate as an active cascode circuit that protects transistor 204 from high voltages at SINK_OUT and monitors I_SUM so that the $V_{DS}$ of transistor 203 and the $V_{DS}$ of 204 are approximately equal over the operational range of circuit 200.

In operation, REG_TOP decreases when delivering stimulation thereby causing the voltage drop over transistors 202 and 204 to decrease proportionately due to the decreased headroom of the bilateral circuit. Because of this decrease, the $V_{DS}$ of transistor 202 decreases causing transistor 207 to begin to turn OFF. This, in turn, causes the $V_{GS}$ of transistor 205 to increase and turn transistor 205 ON more, thereby decreasing the $V_{GS}$ of transistor 206. Consequently, transistor 206 begins to turn OFF, which causes the $V_{GS}$ of transistor 202 to increase. That is, transistor 206 replaces voltage on transistor 202, VG_CASC, causing its resistive value to decrease, thereby restoring voltage on $V_{DS}$ of transistor 204.

Transistors 208-210 set the current for transistors 205-207 based on I_FDBK. I_FDBK is a reference current and may be generated by circuitry at the front end of example circuit 200. In particular, transistor 208 generates a $V_{GS}$ which is then applied to transistors 209 and 210. This then sets the current for transistor 205 and transistor 206, respectively, thereby causing transistors 209 and 210 to operate as current sources.

When circuit 200 operates as a switch, transistors 211 and 212 are turned ON and transistors 213 and 214 are turned OFF. Transistors 214 and 216 may remain OFF for a period of time before being turned ON to prevent the supply voltage from shorting through transistors 216, 214 and 212. In this configuration, transistors 215 and 215 drive transistors 202 and 204 into saturation. This results in SNK_OUT being coupled to the low reference voltage REG_BTM through transistors 202 and 204 and circuit 200 sinks an amount of current based on the amount of current required to be sunk by the stimulation electrode given load conditions and current distribution at the stimulated tissue site adjacent the electrode. In this manner, circuit 200 can be configured to operate as either an unregulated current path or a regulated current path.

Circuit 200 may be turned OFF by turning ON transistors 211, 212, 214 and 217 and turning OFF transistors 213, 215 and 216. Turning ON transistors 211 and 212 turns OFF the active cascode transistors and the master transistor, i.e., transistors 205-210, and transistor 203, respectively. Transistor 217 serves to turn transistor 202 OFF when it is need to be in a high impedance state. Transistor 217 ties the gate (VG_CASC) of transistor 202 to ground, effectively turning transistor 202 OFF.

Transistors 202-217 may be implemented as N-type and P-type MOSFET transistors configured to operate in a depletion mode. It should be understood, however, that circuit 200 may be implemented using various types and configurations of transistors. Because transistors 213-217 are small in size compared to output transistor 202, circuit 200 may be smaller in size than a circuit 130 (FIG. 9) that includes additional switches and, therefore, more easily implemented with a reduced chip size.

As mentioned above, techniques of this disclosure support delivering electrical stimulation current via a housing anode of an IMD while substantially simultaneously delivering electrical stimulation current via one or more anodes on one or more leads engaged to the IMD. Alternatively, the techniques may comprise delivering electrical stimulation current via a housing cathode of an IMD while substantially simultaneously delivering stimulation current via one or more cathodes and one or more anodes on one or more leads engaged to the IMD. Such configurations may allow a user to control current paths between a housing-based anode and a lead-based anode(s), for example, in a relative manner to achieve different electric field shapes, sizes, or locations. In some examples in which the housing electrode is configured as a cathode to deliver stimulation current substantially simultaneously with one or more cathodes and one or more anodes on one or more leads engaged to the IMD, the amplitude of the cathode current may be kept at a subthreshold level. By combining aspects of a bipolar or multipolar stimulation arrangement, e.g., by using anodes on one or more leads to source current, with aspects of a unipolar stimulation arrangement, e.g., by using an anode on the housing of the IMD, the system may provide an omnipolar stimulation arrangement that delivers to a user more localized stimulation while consuming less power than may be achievable using bipolar or multipolar stimulation.

Referring to FIGS. 6-8, in one specific example, a bipolar or multipolar stimulation arrangement may be combined with a unipolar arrangement by applying the output of circuit 180, SRC_OUT, from one current source to a lead anode, e.g., lead electrode 48A while substantially simultaneously applying SRC_OUT from another current source to the housing anode, e.g., housing electrode 48Q. The output of circuit 200, SNK_OUT, is applied to a lead cathode, e.g., lead electrode 48B (or multiple lead cathodes), in order to sink the summed current applied by the housing electrode and the lead electrode. Additional lead electrodes may be similarly configured as anodes and cathodes to source or sink additional current as needed.

Figure 9A:
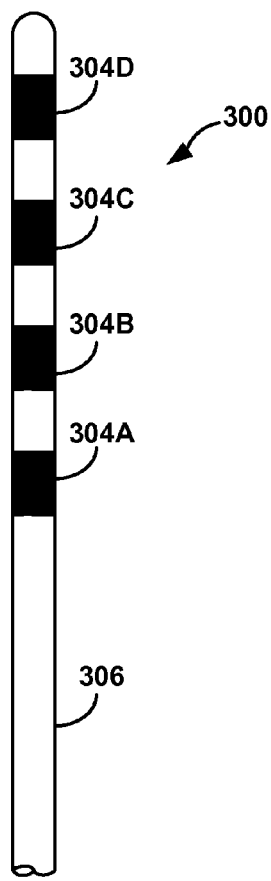
FIGS. 9A-9B are conceptual diagrams illustrating example leads and electrode configurations that may be used for delivering electrical stimulation therapy as described in this disclosure.
Figure 9B:
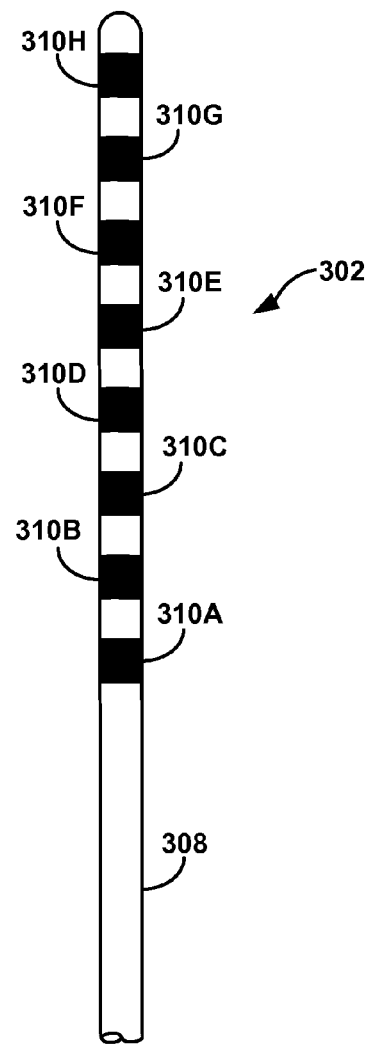

FIGS. 9A and 9B are conceptual diagrams illustrating two different implantable stimulation leads. Leads 300 and 302 are embodiments of leads 12A and 12B shown in FIGS. 1 and 2. As shown in FIG. 9A, lead 300 includes four electrodes 304 (includes electrodes 304A-304D) mounted at various lengths of lead body 306.

Electrodes 304A, 304B, 304C, and 304D are equally spaced along the axial length of lead body 306 at different axial positions. Although not depicted, in some examples, each electrode 304 may have two or more electrodes located at different angular positions around the circumference of lead body 306, forming segmented electrodes. Electrodes of one circumferential location may be lined up on an axis parallel to the longitudinal axis of lead 300. Alternatively, different electrodes may be staggered around the circumference of lead body 306. In addition, lead 300 or 302 may include asymmetrical electrode locations around the circumference of each lead or electrodes of the same level that have different sizes. These electrodes may include semi-circular electrodes that may or may not be circumferentially aligned. Lead body 306 may include a radiopaque stripe (not shown) along the outside of the lead body.

FIG. 9B illustrates lead 302 that includes more electrodes than lead 300. Lead 302 includes lead body 308. Eight electrodes 310 (310A-310H) are located at the distal end of lead 302. Each electrode 310 may be evenly spaced from one or more adjacent electrode and includes one or more electrodes. Although not depicted, in some examples, each electrode 310 includes four electrodes distributed around the circumference of lead body 308. Therefore, lead 302 may include 32 electrodes in some example configurations. Each electrode may be substantially rectangular in shape. Alternatively, the individual electrodes may have alternative shapes, e.g., circular, oval, triangular, or the like.

Figure 10:
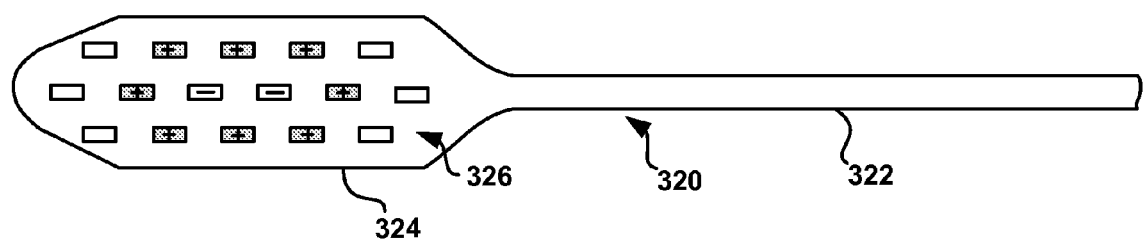
FIG. 10 is a conceptual diagram illustrating an example paddle lead that may be used for delivering electrical stimulation therapy as described in this disclosure.

FIG. 10 is a conceptual diagram illustrating an example paddle lead 320 that may be used for delivering electrical stimulation in accordance with the techniques in this disclosure. In the example of FIG. 10, lead 320 includes a lead body 322 and a lead paddle section 324 carrying an array of electrodes 326 arranged in three rows having five, six and five electrodes, respectively. Electrodes indicated by plus (+) signs are anodes, electrodes indicated by minus (−) signs are cathodes, and electrodes without signs are inactive electrodes. Paddle lead 320 may be configured to include lesser or greater numbers of electrodes. In some implementations, paddle lead 320 may be similar to the Specify™ 5-6-5 paddle lead commercially available from Medtronic, Inc. of Minneapolis, Minn.

Figure 11:
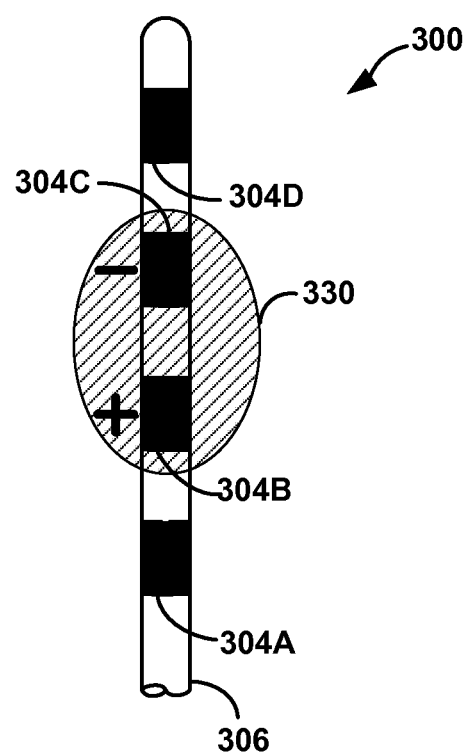
FIG. 11 is conceptual diagram illustrating a stimulation field that may be produced using a bipolar stimulation arrangement.

FIG. 11 is conceptual diagram illustrating a stimulation field that may be produced using a bipolar stimulation arrangement. FIG. 11 depicts stimulation field 330 produced using lead 300, as shown in FIG. 9A. As previously mentioned, a bipolar stimulation arrangement, i.e., an arrangement in which any anode delivering current, or cathode receiving current, is located on one or more leads, may provide stimulation fields that are smaller and have localized shapes (due to the close proximity between the anodes and cathodes) as compared to the sphere-like field created by a unipolar stimulation arrangement. In the example shown in FIG. 11, stimulation field 330 is produced when electrode 304B is configured to act as an anode and source current, and electrode 304C is configured to act as a cathode and sink the current sourced by electrode 304B, acting as an anode. Although not depicted in FIG. 11, multiple anodes and/or multiple cathodes on one or more leads may be used to create a stimulation field in multipolar stimulation arrangement. As seen in FIG. 11, a bipolar stimulation arrangement may produce a localized and tightly constrained stimulation field 330 due to the proximity of the anode and cathode, namely electrodes 304B and 304C, respectively, used to produce field 330. In this manner, a bipolar stimulation arrangement producing such a localized and tightly constrained stimulation field may be particularly useful in specifically targeting one or more stimulation sites of a patient.

Figure 12:
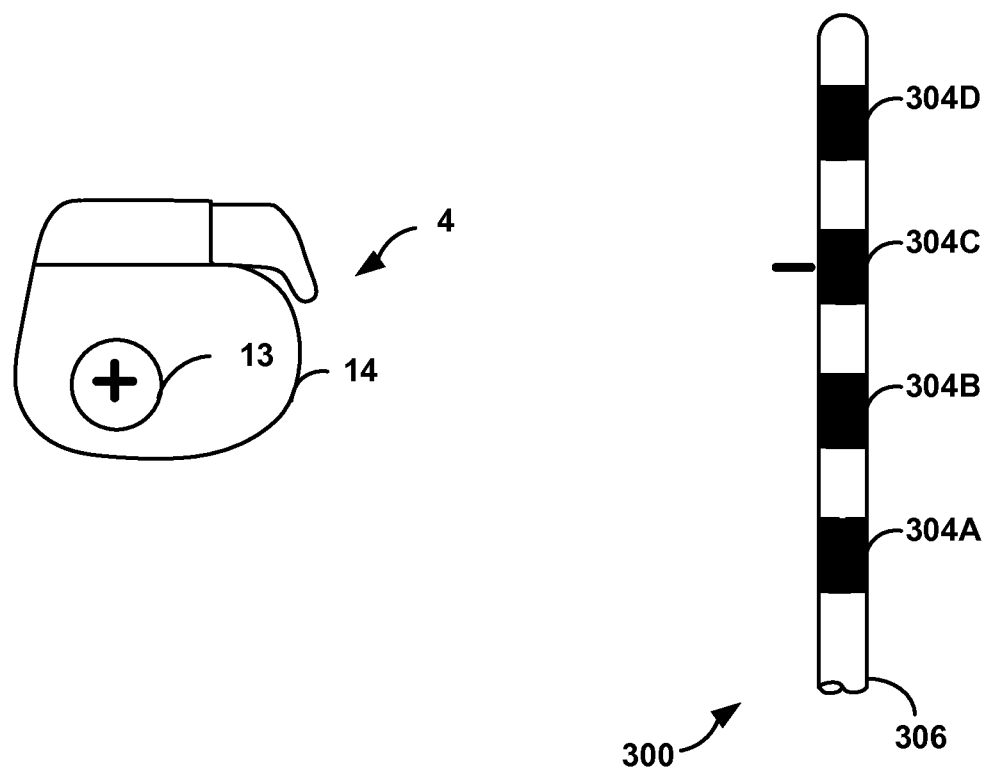
FIG. 12 is conceptual diagram illustrating a unipolar stimulation arrangement that may be produced using a unipolar stimulation arrangement.

FIG. 12 is a conceptual diagram illustrating a unipolar stimulation arrangement. FIG. 12 depicts an electrode on housing 14 of IMD 4 and an electrode on lead 300. A proximal end of lead 300 is coupled to the housing of IMD 4, although this is not shown in the example of FIG. 12. In the unipolar stimulation arrangement shown in FIG. 12, an anode on the housing, e.g., housing electrode 13 or electrode 37 (of FIG. 2), sources current and a cathode, e.g., 304C, on lead 300 sinks current. Although such a configuration may be desirable due to the lower power consumption that results from the low impedance path through the tissue of patient 6, the stimulation field produced by a unipolar stimulation arrangement may resemble a large sphere, in contrast to the localized field 330 shown in FIG. 11. A large stimulation field may, in some patients, be less desirable than a smaller stimulation field 330, like in FIG. 11, due to the increased volume of tissue activation that may result from a larger field.

In accordance with this disclosure, aspects of a unipolar stimulation arrangement and a bipolar or multipolar stimulation arrangement may be combined, providing an omnipolar stimulation arrangement and thereby allowing a user to control current paths between the can-based anode and the lead-based anode(s) in a relative manner to achieve different stimulation field shapes. Such an arrangement may allow a user, e.g., patient 6, to benefit from the lower power consumption, and thus longer battery life of IMD 4, that may result from use of a unipolar stimulation arrangement while also benefiting from the smaller, and thus more localized, stimulation field that may result from the use of a bipolar stimulation arrangement. An omnipolar stimulation arrangement as described in this disclosure may also provide programming benefits. For example, such an arrangement may require fewer electrode specifications from a user, and may automatically balance stimulation settings to produce valid settings.

FIGS. 13-16 are conceptual diagrams illustrating exemplary configurations combining bipolar or multipolar stimulation arrangements with unipolar stimulation arrangements using the techniques of this disclosure. In general, FIGS. 13-16 depict a housing anode, e.g., electrode 13 or electrode 37 (of FIG. 2), sourcing stimulation current in conjunction with one or more anodes on one or more leads 300 substantially simultaneously also sourcing current, as will be described in more detail below. One or more electrodes on one or more leads are configured as cathodes to sink stimulation current. The electrodes on the housing and on the leads are configured as anodes or cathodes by configuring current regulators coupled to the electrodes to source or sink current, respectively. In such a configuration, stimulation current is delivered to a patient using a combination of a unipolar stimulation arrangement, i.e., a housing electrode configured to act as an anode to source current, and a bipolar stimulation arrangement, i.e., an electrode on a lead configured to act as an anode to source current, thereby creating a hybrid stimulation arrangement. For ease of illustration purposes, lead wires that connect leads to IMD 4 have not been shown.

Figure 13:
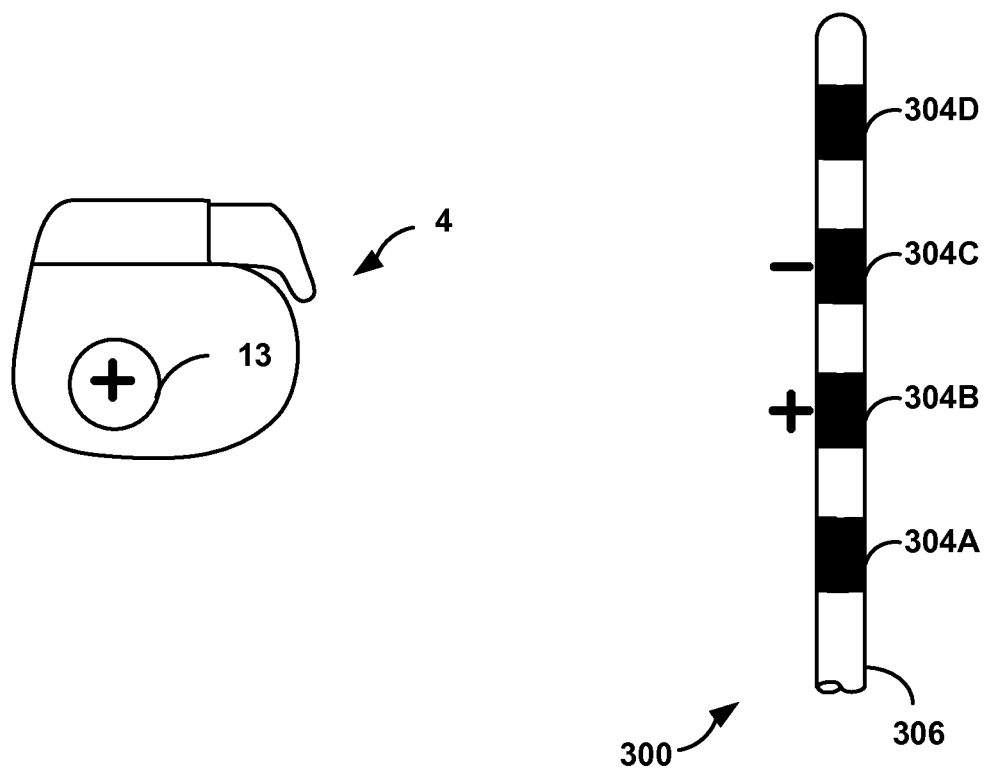
FIGS. 13-16 are conceptual diagrams illustrating various omnipolar stimulation arrangements that may be produced using the techniques of this disclosure.

FIG. 13 depicts one example of such a hybrid, omnipolar configuration, in accordance with this disclosure. FIG. 13 depicts an anode on the housing, e.g., electrode 13 or electrode 37 (of FIG. 2), configured to source current and a cathode, e.g., 304C, on lead 300 configured to sink current, thereby producing a first stimulation field (not shown) between electrodes 13, 304C. FIG. 13 further depicts electrode 304B configured to act as an anode and source current, and electrode 304C configured to act as a cathode and sink the current sourced by electrode 304B, thereby producing a second stimulation field (not shown) between electrodes 304B, 304C. Although FIG. 13 depicts electrode 304C acting as a common cathode that sinks current sourced by both electrode 13 and electrode 304B, it should be noted that a second electrode, e.g., electrodes 304A or 304D, may be configured to act as a cathode to also sink current. In other words, the two anodes need not share a common cathode.

In FIG. 13, the size of the stimulation field produced between the housing anode 13 and the lead anode 304C may be reduced and more localized when compared with a stimulation field produced using the arrangement shown in FIG. 12 in which a unipolar stimulation arrangement was used to provide stimulation. In addition, the configuration shown in FIG. 13 may produce a smaller and more localized stimulation field between lead electrodes 304B and 304C when compared with the configuration shown in FIG. 11 in which a bipolar stimulation arrangement was used to provide stimulation. By combining aspects of a bipolar stimulation arrangement, e.g., as shown in FIG. 11, with aspects of a unipolar stimulation arrangement, e.g., as shown in FIG. 12, the arrangement of FIG. 13 may deliver to a user more localized stimulation while consuming less power than would be achievable using bipolar stimulation.

In addition, in accordance with this disclosure, the example stimulation arrangements depicted in FIGS. 13-16 may allow a combination of electrodes to be selected to deliver an overall predetermined, summed stimulation current comprising the stimulation current delivered by housing anode 13 and the one or more lead anodes 304B. As mentioned previously, current is delivered substantially simultaneously by a housing anode and one or more anodes on one or more leads. For example, referring to FIG. 13, first electrode 13, second electrode 304B, and third electrode 304C may be selected to deliver an overall predetermined summed stimulation current comprising the stimulation current delivered via first electrode 13 and second electrode 304B. First electrode 13 and second electrode 304B may be configured, for example, to each deliver a pulse substantially simultaneously. That is, the pulses delivered by first electrode 13 and second electrode 304B may overlap one another in time partially or completely. In this manner, the delivered pulses (or waveforms) may sum together to produce a predetermined combined current.

By way of specific example, patient 6 may desire stimulation therapy that requires a stimulation current of about 50 mA. Patient 6 may first select a cathode, e.g., electrode 304C, on lead body 306 to sink a cathodal current, e.g., 50 mA, such that adequate therapy coverage is achieved. Housing electrode 13 may be then be recruited as an anode (source) in order to balance the required cathodal current, e.g., 30 mA, thereby taking advantage of the low impedance path through tissue, and thus the low power consumption of such a configuration. Electrode 304B on lead 300 may also be selected as an anode to deliver, substantially simultaneously with the 30 mA delivered by housing electrode 13, the remaining current requirement, i.e., 20 mA, to produce the desired therapy, thereby taking advantage of a localized stimulation field produced between the lead electrodes. In such a manner, the example implementation of FIG. 13 may provide a user with flexibility in shaping a stimulation field, minimizing side effects, and fine tuning therapy, while also conserving the power of IMD 4. The example implementation of FIG. 13 delivers an overall predetermined summed stimulation current, e.g., 50 mA, by delivering current via first electrode 13 (30 mA) substantially simultaneously with current delivered via second electrode 304B (20 mA).

In the above example, the specific current levels between the housing electrode and the lead electrode may be based on a percentage of the overall current to be delivered, or the actual current amplitudes. For example, if the overall current to be delivered is 50 mA, housing electrode 13 may be selected to deliver 60% of the overall current (30 mA) and electrode 304B may be selected to deliver the remaining 40% of the overall current (20 mA). Or, rather than use percentages, housing electrode 13 may be selected to deliver a specific current, e.g., 30 mA, and electrode 304B may be selected to deliver the remaining current, e.g., 20 mA. In another example, the user may select specific values for two of three electrodes to be used in delivering stimulation therapy, and the system would then automatically calculate the current to be sourced or sunk by the third electrode in order to balance the currents, i.e., overall source current=overall sink current. In one example, housing electrode 13 would be adjusted in order to balance the other electrode currents.

As mentioned above, programs generated by a clinician programmer and selected by a user using a patient programmer, for example, specify stimulation parameters. The programs may be defined by the duration, current or voltage source amplitude, current or voltage sink amplitude, pulse width and pulse rate of the stimulation as well as the electrode combination, the percentage of source current distributed among or contributed by a housing anode and one or more lead anodes on one or more leads, and the percentage of sink current sunk by one or more cathodes.

Continuing the example above, a user may select, e.g., using a patient programmer, a program that delivers an overall current of 50 mA, with the housing electrode 13 delivering 60% of the overall current (30 mA) and electrode 304B delivering the remaining 40% of the overall current (20 mA). Processor 50 may retrieve the specific stimulation parameters defined by the selected program from memory and control stimulation generator 60 to deliver stimulation according to the selected program. In particular, stimulation control module 62 of stimulation generator 60A, for example, may generate a control signal to close a switch, thereby coupling lead electrode 304B to a regulated current source 72A, thus configuring lead electrode 48A as a regulated anode.

Stimulation control module 62 may then generate a control signal to close another switch, thereby coupling housing electrode 13 to a regulated current source, thus configuring housing electrode 13 as a regulated anode. Stimulation control module 62 may also configure a lead electrode, e.g., lead electrode 304C, as a regulated cathode by generating a control signal to a close switch, thereby coupling lead electrode 304C to a regulated current sink. The regulated current sink receives specified amounts of regulated currents from anode 13 and 304B. In order for housing electrode 13 to deliver 60% of the overall current, stimulation control module 62 may activate 60 percent of the N parallel current regulators that comprise the current regulator to which electrode 13 is coupled. Likewise, in order for lead electrode 304B to deliver 40% of the overall current, stimulation control module 62 may activate 40 percent of the N parallel current regulators that comprise the current regulator to which electrode 304B is coupled.

In addition, the example implementation of FIG. 13 may allow a user to more effectively shape, focus or steer a stimulation field. Steering a stimulation field may allow a user to transition between a unipolar stimulation arrangement and a bipolar (or multipolar) stimulation arrangement or between a bipolar (or multipolar) arrangement and a unipolar arrangement, permitting the user to select different weighted combinations of current delivered to one or more lead cathodes by the housing anode and lead anode. The user may stop the transition at a desired point to use both a housing anode and at least one lead anode. This may allow more flexibility in selecting the strength of the anode "shields" on the lead that are in proximity to the cathodes. Further, the example configuration of FIG. 13 may automatically adjust the housing electrode to balance the currents after a user-requested change to the contribution of any other electrode. This feature may enhance usability by relieving the user of having to manually balance currents.

Figure 14:
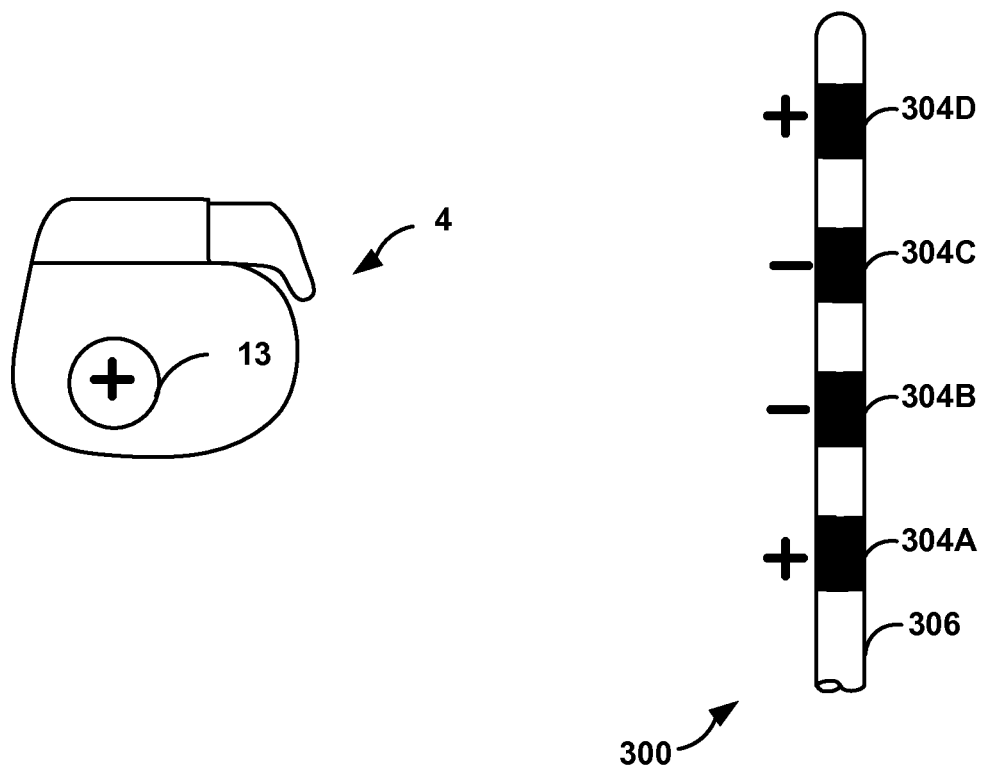

FIG. 14 depicts another example of a stimulation arrangement, in accordance with this disclosure. The configuration depicted in FIG. 14 may produce a first stimulation field using an electrode on IMD 4 and an electrode on lead 300. In particular, an anode on the housing, e.g., electrode 13 or electrode 37 (of FIG. 2), sources current and a cathode, e.g., 304B, on lead 300 sinks current, thereby producing a first stimulation field (not shown). A second stimulation field may be produced when electrode 304A is configured to act as an anode and source current, and electrode 304B is configured to act as a cathode and sink the current sourced by electrode 304A. Although FIG. 14 depicts electrode 304B acting as a common cathode that sinks current sourced by both electrode 13 and electrode 304A, it should be noted that a second electrode may be configured to act as a cathode to also sink current. In other words, the two anodes need not share a common cathode.

The configuration shown in FIG. 14 may also produce a third stimulation field when electrode 304D is configured to act as an anode and source current, and electrode 304C is configured to act as a cathode and sink the current sourced by electrode 304D. The three stimulation fields add together to form one overall field. As in FIG. 13, electrodes may be selected to deliver an overall predetermined summed stimulation current comprising the stimulation current delivered via first electrode 13 second electrode 304A, and third electrode 304D.

By way of specific example, patient 6 may desire stimulation therapy that requires a stimulation current of 50 mA. Electrodes 304A and 304D on lead 300 may be selected as anodes to deliver, e.g., 30 mA, to produce the desired therapy, thereby taking advantage of the resulting localized stimulation fields (not shown). Can electrode 13 may then default to an anode in order to deliver the remaining current requirement, e.g., 20 mA, substantially simultaneously with the 30 mA delivered by electrodes 304A and 304D, for example, thereby taking advantage of the low impedance path through tissue, and thus the low power consumption of such a configuration. In one example, a user may select a stimulation program that divides the 20 mA approximately equally such that two localized stimulation fields (not shown) are each produced by stimulation currents of approximately 10 mA. In such a manner, the example implementation of FIG. 14 may provide a user with flexibility in shaping multiple stimulation fields using a single lead while also conserving the power, and thus extending the battery life, of IMD 4.

Figure 15:
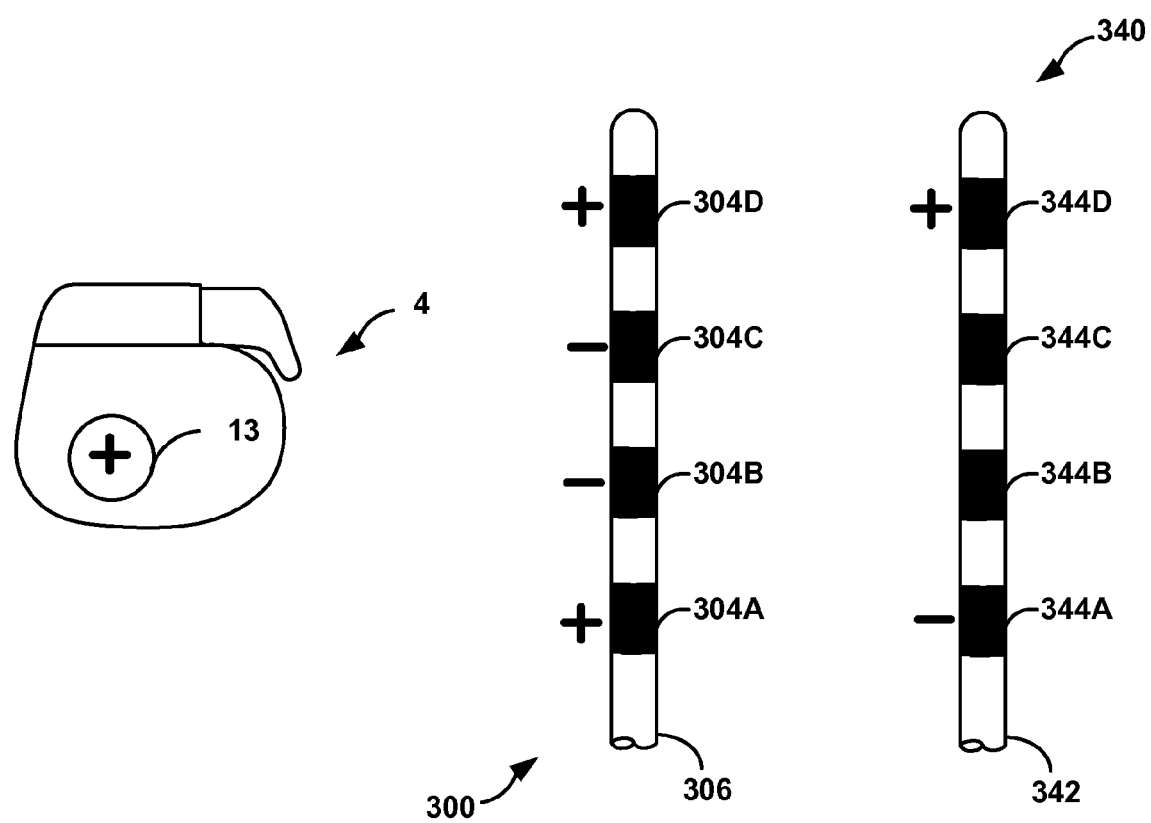

FIG. 15 depicts another example of a stimulation arrangement, in accordance with this disclosure. FIG. 15 is similar to the implementation shown in FIG. 14, with the addition of a second lead 340 having lead body 342 having four electrodes 344 (electrodes 344A-344D) mounted at various lengths of lead body 342. Like FIG. 14, the configuration shown in FIG. 15 produces a first stimulation field using a housing electrode on IMD 4 and an electrode on lead 300. In particular, an anode on the housing, e.g., electrode 13, sources current and a cathode, e.g., 304B, on lead 300 sinks current, thereby producing the first stimulation field. A second stimulation field is produced when electrode 304A is configured to act as an anode and source current, and electrode 304B is configured to act as a cathode and sink the current sourced by electrode 304A. A third stimulation field is produced when electrode 304D is configured to act as an anode and source current, and electrode 304C is configured to act as a cathode and sink the current sourced by electrode 304D.

In the implementation shown in FIG. 15, a fourth stimulation field may be produced on the second lead, e.g., lead 340. The four fields add together to produce one overall stimulation field. The fourth stimulation field may be produced when electrode 344A on lead 340 is configured to act as an anode and source current, and electrode 344D on lead 340 is configured to act as a cathode and sink the current sourced by electrode 344A. The fourth stimulation field may be larger than the second and third stimulation fields produced by electrodes on lead 300 due to the fact that the currents sourced and sunk by the anode and cathode, electrodes 344A and 344D, respectively, creating the fourth stimulation field are larger than the currents sourced and sunk by the electrodes used to produce each of second and third stimulation fields. As in FIG. 14, electrodes may be selected to deliver an overall predetermined summed stimulation current comprising the stimulation current delivered via first electrode 13, second electrode 304A, and third electrode 304D on lead 300. In addition, second lead 340 may also provide further flexibility in delivering stimulation therapy by allowing additional stimulation field shapes to be used for stimulation.

Figure 16:
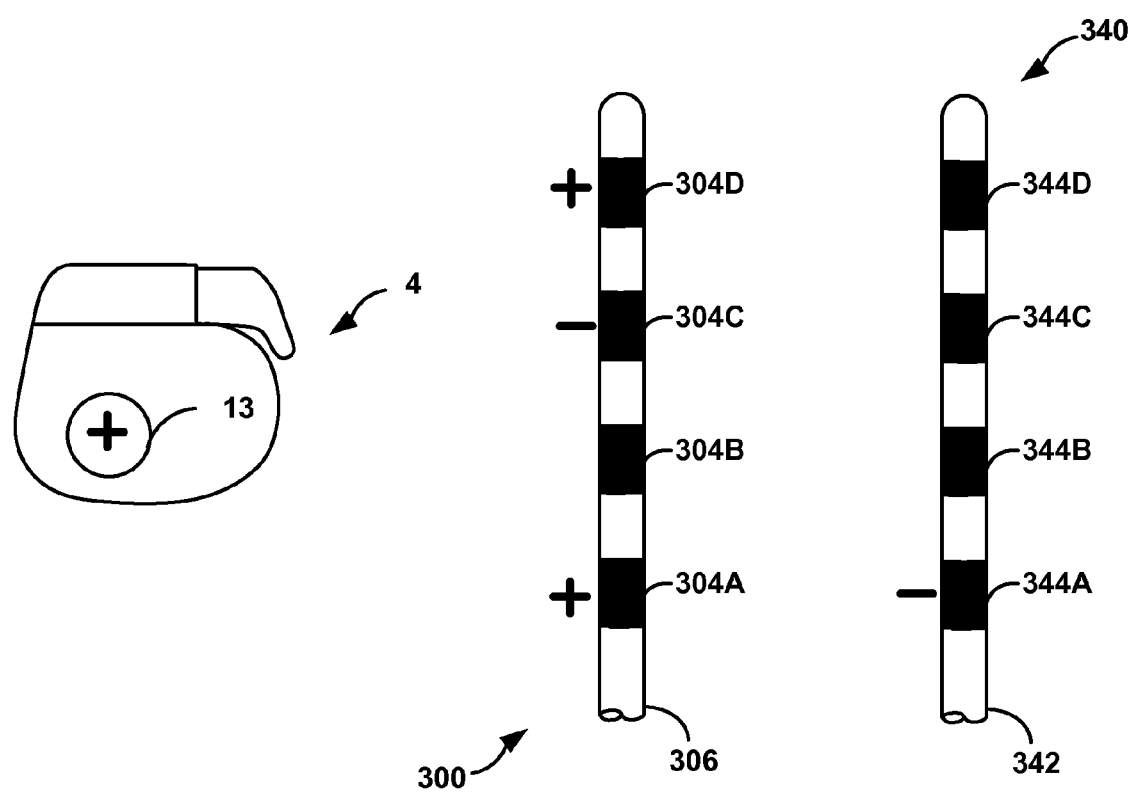

FIG. 16 depicts another example of a stimulation arrangement, in accordance with this disclosure. FIG. 16 is similar to the implementation shown in FIG. 15, depicting IMD 4, first lead 300, and second lead 340. As in FIG. 15, the configuration depicted in FIG. 16 may produce a first stimulation field using an electrode on IMD 4 and an electrode on lead 300. In particular, an anode on the housing, e.g., electrode 13, sources current and a cathode, e.g., 304B, on lead 300 sinks current, thereby producing the first stimulation field. A second stimulation field may be produced when electrode 304A is configured to act as an anode and source current, and electrode 304B is configured to act as a cathode and sink the current sourced by electrode 304A.

Like FIG. 15, the example implementation shown in FIG. 16 includes second lead 340. In contrast to FIG. 15, however, a third stimulation field may be created between leads 300, 340. The third stimulation field (not shown) may be produced when electrode 304D on lead 300 is configured to act as an anode and source current, and electrode 344C on lead 340 is configured to act as a cathode and sink the current sourced by electrode 304D. As in FIGS. 13-15, electrodes may be selected to deliver an overall predetermined summed stimulation current.

By way of specific example, patient 6 may desire stimulation therapy that requires a stimulation current of 50 mA. Can electrode 13 may be selected as an anode in order to deliver the majority of the current, e.g., 30 mA, thereby taking advantage of the low impedance path through tissue, and thus the low power consumption of such a configuration. Electrode 304A on lead 300 may also be selected as an anode to deliver, substantially simultaneously with the 30 mA delivered by can electrode 13, the remaining current requirement, e.g., 20 mA, to produce the desired therapy, thereby taking advantage of the resulting localized stimulation field (not shown). In such a manner, the example implementation of FIG. 13 may provide a user with flexibility in shaping a stimulation field while also conserving the power of IMD 4. Further, the user may also select a stimulation program that generates the stimulation field (not shown), thereby providing the user with additional therapeutic effects that may otherwise be unavailable if a single lead were used.

It should be noted that although leads similar to lead 300 depicted in FIG. 9A were used in the example implementations shown in FIGS. 13-16, leads similar to lead 302 depicted in FIG. 9B may also be used. In addition, leads used to implement techniques of this disclosure are not limited to the leads shown in FIGS. 9A-9B, or the four-electrode configurations depicted in FIGS. 13-16. In some examples, leads may include more or less than four electrodes.

In addition, although not depicted, a paddle lead, e.g., paddle lead 320 shown in FIG. 10, may also be used to implement the techniques of this disclosure. For example, a paddle lead may replace the single lead 300 depicted in FIG. 13. Or, in another example, two paddle leads may replace the two leads 300, 340 depicted in FIG. 15. In accordance with this disclosure, an anode on the can may deliver stimulation current substantially simultaneously with current delivered by an anode on the paddle lead.

It should also be noted that the techniques of this disclosure are not limited to implementations that use one or two leads. Rather, any number of leads may be used. For example, in some implementations, four leads may be used. In addition, although the example configurations depicted in FIGS. 13-16 depict can electrode 13 as an anode, as mentioned above, can electrode 13 may also be configured as a cathode. Can cathode 13 may be used together with one or more cathodes and one or more anodes on one or more leads in order to deliver stimulation in a manner similar to that described above.

Figure 17:
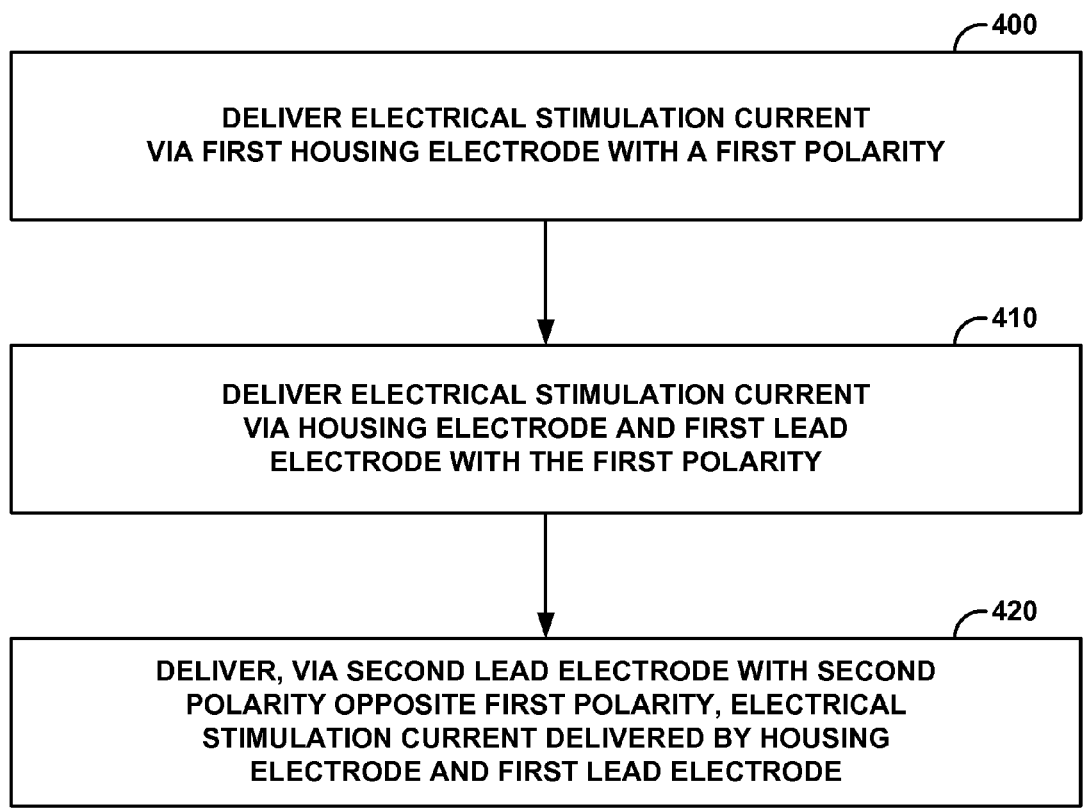
FIG. 17 is a flow diagram illustrating an example method of delivering electrical stimulation using the techniques of this disclosure.

FIG. 17 is a flow diagram illustrating an example method of delivering electrical stimulation using the techniques of this disclosure. In the method shows in FIG. 17, IMD 4, and in particular, stimulation generator 60, delivers electrical stimulation current with a first polarity (i.e., positive or negative) via a first, or housing/case, electrode of IMD 4 carried by housing 14 of IMD 4, e.g., housing electrode 13 or housing electrode 37 (400). Substantially simultaneously with the electrical stimulation current delivered via the first electrode, IMD 4, and in particular, stimulation generator 60, delivers electrical stimulation current with the first polarity (i.e., positive or negative) via a second electrode, e.g., electrode 304B carried by a lead, e.g., lead 300, coupled to housing 14 of IMD 4 (410). A third electrode of IMD 4, e.g., electrode 304C, delivers electrical stimulation current with a second polarity opposite the first polarity (i.e., negative or positive) delivered via the first electrode and the second electrode (420). The third electrode may be carried by the lead that includes the second electrode, or the third electrode may be carried by another lead. The electrical stimulation may be selected to provide at least one of deep brain stimulation and spinal cord stimulation.

In one example, the first electrode is a first anode, the second electrode is a second anode, and the third electrode is a cathode. In another example, the stimulation is selected to provide at least one of deep brain stimulation and spinal cord stimulation. In yet another example, the first electrode is a first cathode, the second electrode is a second cathode, and the third electrode is an anode.

In one example, using the techniques of this disclosure, the first electrode, the second electrode, and the third electrode are selected to deliver an overall predetermined summed stimulation current comprising the stimulation current delivered via the first electrode and the second electrode.

In some examples, the first electrode is a first anode, and the second electrode is one of a plurality of anodes integral with the lead. In another example, the lead is a first lead, and the plurality of anodes is a first plurality of anodes. In such an example, IMD 4 may deliver electrical stimulation current via one of a second plurality of anodes integral with a second lead substantially simultaneously with the electrical stimulation current delivered via the first anode and the one of a second plurality of anodes. In some examples, at least one cathode, e.g., electrode 344C, on the second lead, e.g., lead 340, may receive electrical current.

In some examples, stimulation generator 60A may couple the first electrode, e.g., electrode 13 or electrode 37, to a first regulated current path to deliver a first amount of the electrical stimulation current. Stimulation generator 60A may also couple the second electrode, e.g., electrode 304B, via switch array 66, to a second regulated current path to deliver a second amount of the electrical stimulation current. Stimulation generator 60A may couple a third electrode, e.g., electrode 304C, to a regulated current path to receive a third amount of the electrical stimulation current approximately equal to a sum of the first and second amounts of the electrical stimulation current. In one example, the first amount of the electrical stimulation current is a first regulated source current, the second amount of the electrical stimulation current is a second regulated source current, and the third amount of the electrical stimulation current is a regulated sink current that is approximately equal to a sum of the first and second regulated source currents.

As mentioned above, the electrical stimulation may be constant current-based or constant voltage-based stimulation in the form of pulses or continuous waveforms. In one constant voltage-based implementation, the electrical stimulation current delivered by the first electrode (anode), i.e., the housing electrode, is a first stimulation current, the electrical stimulation current delivered by the second electrode is a second stimulation current, and the electrical stimulation current received by the third electrode is a third stimulation current. The first electrode may be coupled to a first regulated voltage source to deliver the first stimulation current, the second electrode may be coupled to a second regulated voltage source to deliver the second stimulation current, and the third electrode may be coupled to a third voltage source to deliver the third stimulation current. In some example constant voltage-based implementations, the third stimulation current delivered is approximately equal to the sum of the first stimulation current and the second stimulation current.

In some example configurations, the case electrode may act as a cathodal current sink. In constant voltage-based implementations of such example configurations, the first electrode (cathode), i.e., the housing electrode, may be coupled to a first regulated voltage source to deliver (sink) a first stimulation current, a second electrode may be coupled to a second regulated voltage source to deliver (sink) a second stimulation current, and a third electrode may be coupled to a third voltage source to deliver (source) a third stimulation current. In some example constant voltage-based implementations, the third stimulation current is approximately equal to the sum of the first stimulation current and the second stimulation current.

Numerous other configurations are considered to be within the scope of this disclosure. Such configurations may include, but are not limited to the following examples. One example configuration delivers (sources) regulated current via a housing electrode, delivers (sources) regulated current via a first electrode on a lead, and delivers (sinks) regulated current via a second electrode on the same or on a different lead.

Another example configuration delivers (sources) regulated current via a housing electrode, delivers (sources) regulated current via a first electrode on a lead, and delivers (sinks), via a second electrode on the same lead or on a different lead, unregulated current to a reference voltage. That is, the second electrode is electrically coupled to a reference voltage to deliver (sink) unregulated current.

Another example configuration delivers (sources) regulated current via a housing electrode, delivers (sources) regulated current via a first electrode on a lead, and delivers, via a second electrode on the same lead or on a different lead, unregulated current (sources) from a reference voltage. That is, the second electrode is electrically coupled to a reference voltage to deliver (source) unregulated current.

Another example configuration delivers (sinks), via a housing electrode, unregulated current, to a reference voltage (i.e., the housing electrode is electrically coupled to a reference voltage to deliver (sink) unregulated current), delivers regulated current (sources) via a first electrode on a lead, and delivers (sources) regulated current via a second electrode on the same lead or on a different lead.

Another example configuration delivers (sources), via a housing electrode, unregulated current, from a reference voltage (i.e., the housing electrode is electrically coupled to a reference voltage to deliver (sources) unregulated current), delivers regulated current (sources) via a first electrode on a lead, and delivers (sinks) regulated current via a second electrode on the same lead or on a different lead.

Another example configuration delivers (sinks), via a housing electrode, unregulated current, to a reference voltage (i.e., the housing electrode is electrically coupled to a reference voltage to deliver (sink) unregulated current), delivers (sources), from a regulated voltage source, unregulated current via a first electrode on a lead, and delivers (sinks), to a regulated voltage source, unregulated current via a second electrode on the same lead or on a different lead.

Another example configuration delivers (sources), via a housing electrode, unregulated current, from a reference voltage (i.e., the housing electrode is electrically coupled to a reference voltage to deliver (sources) unregulated current), delivers (sources), from a regulated voltage source, unregulated current via a first electrode on a lead, and delivers (sinks), to a regulated voltage source, unregulated current via a second electrode on the same lead or on a different lead.

FIGS. 18-25 are schematic diagrams illustrating example user interfaces presented by the programmer 40 of FIG. 4. Programmer 40 may represent clinician programmer 20 and/or a patient programmer 22 of FIG. 1. FIGS. 18-25 generally depict user interfaces that may permit a clinician and/or patient to transition between a stimulation setting that uses a unipolar electrode arrangement to a stimulation setting that uses a bipolar (or multipolar) electrode arrangement, or transition between a stimulation setting that uses a bipolar (or multipolar) electrode arrangement to a stimulation setting that uses a unipolar electrode arrangement, and permit a range of hybrid, omnipolar electrode arrangements that make use of various combinations of unipolar and bipolar or multipolar relationships between the electrodes. As will be described in more detail below, FIGS. 18-25 depict two types of programming, electrode-based programming and zone-based programming.

Figure 18:
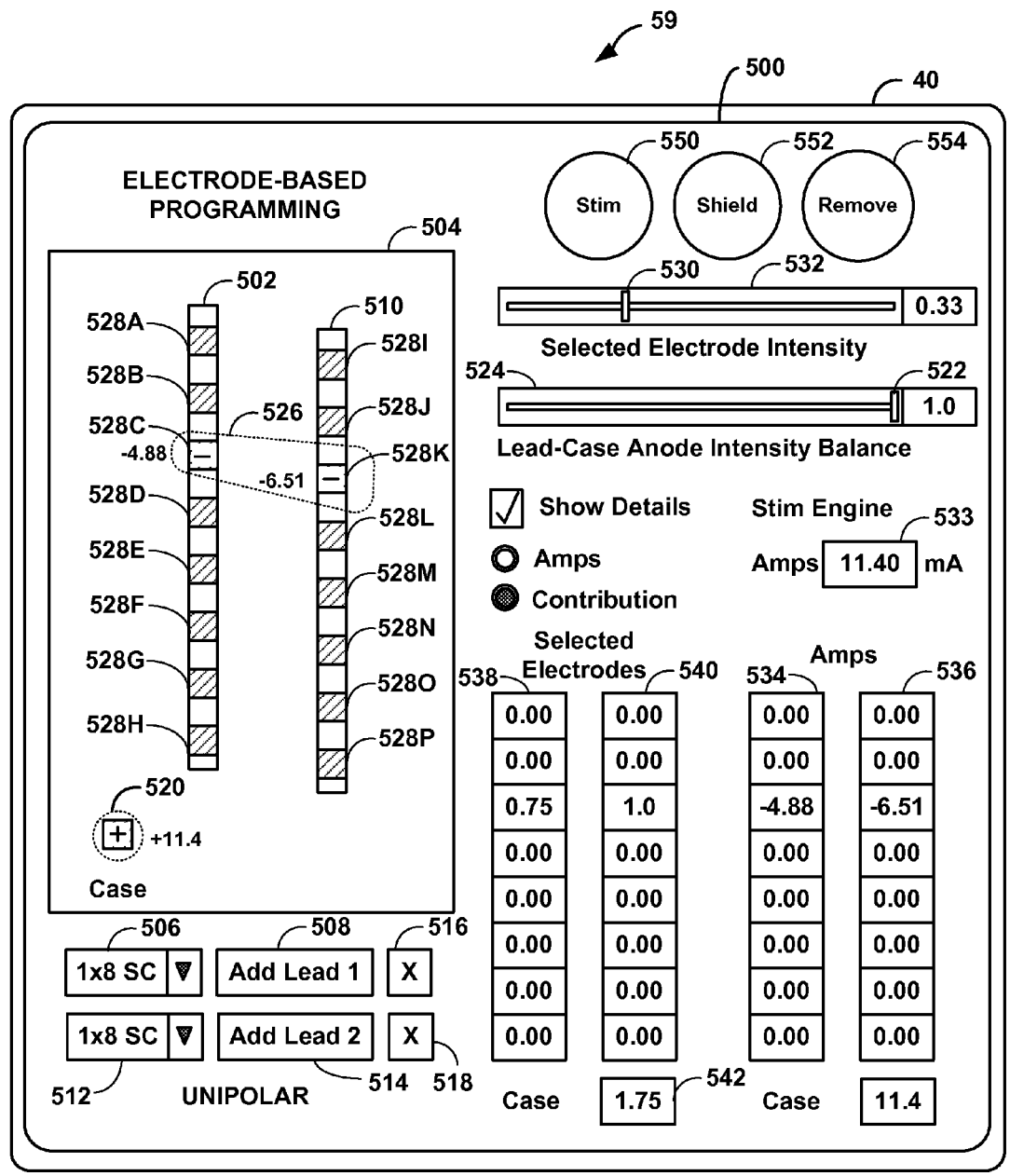
FIGS. 18-22 are schematic diagrams illustrating example user interfaces presented by the programmer of FIG. 4.

FIG. 18 depicts a user interface illustrating a unipolar stimulation arrangement created using electrode-based programming. FIG. 18 depicts user interface 59 provided by programmer 40. User interface 59 includes display screen 500. Display screen 500 may be a touchscreen such that a stylus, mouse or other pointing device may be used to make selections directly on screen 500. Alternatively, or in addition, keys, buttons, wheels and other input devices may be provided on programmer 40, independently of display 500. First lead 502 may be added to window 504 by first selecting a desired type of lead from pull-down menu 506 and then selecting "Add Lead 1" via icon 508. Similarly, second lead 510 may be added to window 504 by selecting the type of lead from pull-down menu 512 and then selecting "Add Lead 2" via icon 514. Icons 516, 518 allow a user to remove a lead from window 504. It should be noted that in some examples, the "Add Lead" icons may not be displayed. The housing electrode, or "case" electrode, indicated at 520 may, in some examples, be permanently displayed in window 504.

In order to select a unipolar stimulation arrangement, a user may first use a stylus to move indicator 522 along horizontal scroll bar 524 until the Lead-Case Anode Intensity Balance indicates 1.0, as shown in FIG. 18. This indicates that intensity is balanced entirely toward a unipolar stimulation arrangement. Next, in order to create field 526, as in FIG. 18, a user may use a stylus, for example, and touch the particular electrodes 528A-528P depicted on leads 502, 510 that the user seeks to create field 526. The user may then use a stylus to move indicator 530 along horizontal scroll bar 532 to select the desired electrode intensity. In FIG. 18, the Selected Electrode Intensity is 0.33, which is used to weight or scale the electrode contributions by the desired intensity to get amplitude outputs in stimulation current. The Selected Electrode Intensity of 0.33 equates in this example to 11.4 mA of overall current stimulation, as indicated in current window 533.

Upon selecting the desired electrode intensity, processor 53 of programmer 40 generates field 526 and depicts the currents associated with the selected electrodes that are needed to generate field 526. Field 526 may be represented by a line, dashed line, colored region, shaded region, or the like. As shown in FIG. 18, case electrode 520 sources the desired 11.4 mA of current while electrode 528C sinks 4.88 mA and electrode 528K sinks the remaining 6.51 mA needed to balance the system. The currents needed to generate field 526 are shown in window 504 as well as in arrays 534, 536, which depict each of the electrodes on each of the two leads and the current in milliamps associated with the electrodes originally selected by the user. Sliding indicator 530 to the right increases the electrode intensity, and thus the overall current delivered and field intensity. As such, the currents needed to create field 526 will increase. Sliding indicator 530 to the left decreases the electrode intensity, and thus the overall current delivered and field intensity. As such, the currents needed to create field 526 will decrease.

In addition, arrays 538, 540 indicate the contributions of the electrodes originally selected by the user. In the example depicted in FIG. 18, the selected electrode that sinks (or sources, in other examples) the most current to produce a given field is assigned a first contribution of 1.0, and the contributions of the remaining electrodes used to produce that particular field are scaled in relation to the electrode having the largest contribution such that the remaining electrodes are assigned contributions that are a percentage of that first contribution. In FIG. 18, electrode 528K sinks 6.51 mA, a value greater than the 4.88 mA sunk by electrode 528C. As such, electrode 528K has a contribution of 1.0, and electrode 528C has a contribution of 4.88 mA/6.51 mA or about 0.75, as indicated in arrays 538, 540. In a unipolar arrangement, like in FIG. 18, the case electrode must source all of the desired current and, as such, it has a contribution of 1.0+0.75=1.75, as indicated at 542.

As mentioned above, in FIG. 18, when the Lead-Case Anode Intensity Balance indicates 1.0, the intensity is balanced entirely toward a unipolar stimulation arrangement. The system then defaults to a unipolar mode, and activates the case to balance the sum of the two electrodes activated (4.88+6.51=11.40 with a small rounding error). This may be advantageous because it may require fewer user actions, e.g., the system automatically configures case electrode 520, and no user interaction on subsequent intensity changes, e.g., the user does not have to balance stimulation in order for the system to enter a valid, programmable state. The system may also default into a more energy efficient mode such that losses in the lead array are only applied once, because the return path does not traverse the lead array wires a second time.

Figure 19:
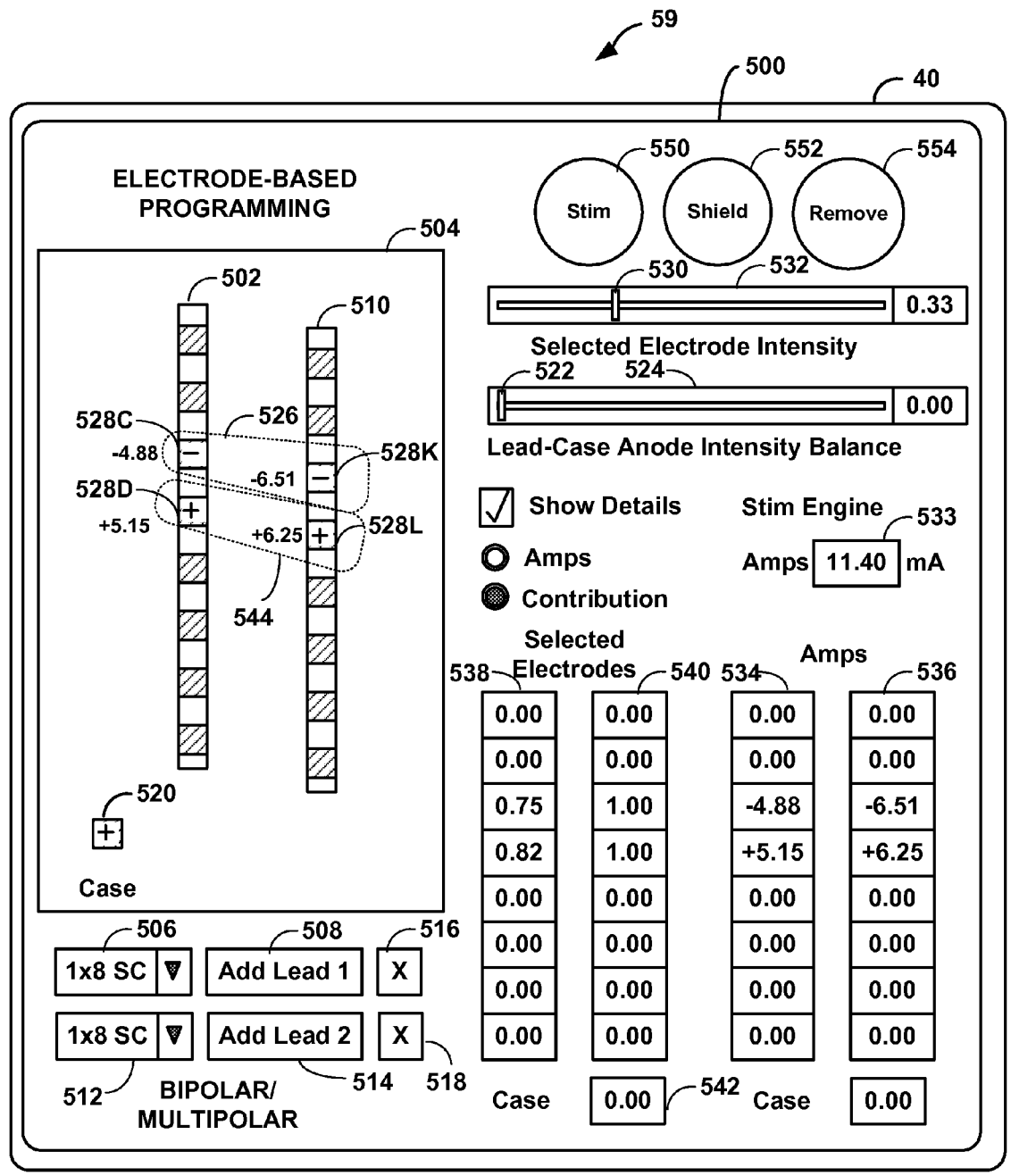

FIG. 19 depicts a user interface illustrating a bipolar/multipolar stimulation arrangement created using electrode-based programming. FIG. 19 depicts user interface 59 provided by programmer 40, similar to that shown in FIG. 18.

In order to select a bipolar/multipolar stimulation arrangement, a user may first use a stylus to move indicator 522 along horizontal scroll bar 524 until the Lead-Case Anode Intensity Balance indicates 0.0, as shown in FIG. 19. This indicates that intensity is balanced entirely toward a bipolar/multipolar stimulation arrangement, i.e., case electrode 520 will not source any current. Next, in order to create the desired fields 526, 544 as in FIG. 19, a user may use a stylus, for example, and touch the electrodes depicted on leads 502, 510 that the user seeks to create fields 526, 544. The user may then use a stylus to move indicator 530 along horizontal scroll bar 532 to select the desired electrode intensity.

In FIG. 19, the Selected Electrode Intensity is 0.33, which is used to scale the electrode contributions by the desired intensity to get amplitude outputs in stimulation current. The Selected Electrode Intensity of 0.33 equates in this example to 11.4 mA of overall current stimulation, as indicated in current window 533, assuming a maximum current of 35 mA. Upon selecting the desired electrode intensity, processor 53 of programmer 40 generates fields 526, 544 and depicts the currents associated with the selected electrodes that are needed to generate fields 526, 544. As shown in FIG. 19, electrodes 528D and 528L, configured as anodes, source 5.15 mA and 6.25 mA (a total of 11.4 mA), respectively. Electrodes 528C and 528K, configured as cathodes, sink 4.88 mA and 6.51 mA (a total of 11.4 mA with a small rounding error), respectively. The currents needed to generate fields 526, 544 are shown in window 504 as well as in arrays 538, 540, which depict each of the electrodes on each of the two leads and the current in milliamps associated with the electrodes originally selected by the user. Sliding indicator 530 to the right increases the electrode intensity, and thus the overall current delivered and field intensity. As such, the currents needed to create fields 526, 544 will increase. Sliding indicator 530 to the left decreases the electrode intensity, and thus the overall current delivered and field intensity. As such, the currents needed to create fields 526, 544 will decrease. It should be noted that sliding indicator 530 all the way to the left, i.e., lead-case anode intensity balance equals zero, may require the user to balance the sink and source currents before a valid combination is achieved.

In addition, arrays 538, 540 indicate the contributions of the electrodes originally selected by the user. In the example depicted in FIG. 19, the selected electrode that sinks (or sources) the most current to produce a given field has a first contribution of 1.0, and the contributions of the remaining electrodes used to produce that particular field are a percentage of that first contribution. In FIG. 19, electrode 528K sinks 6.51 mA, a value greater than the 4.88 mA sunk by electrode 528C. As such, electrode 528K has a contribution of 1.0, and electrode 528C has a contribution of 4.88 mA/6.51 mA or about 0.75, as indicated in arrays 538, 540. Similarly, electrode 528L sources 6.25 mA, a value greater than the 5.15 mA sourced by electrode 528D. As such, electrode 528L has a contribution of 1.0, and electrode 528D has a contribution of 5.15 mA/6.25 mA or about 0.82, as indicated in arrays 538,

540. In a multipolar arrangement, like in FIG. 19, the case electrode does not source any current. As such, it has a contribution of 0.0 mA, as indicated at 542.

Figure 20:
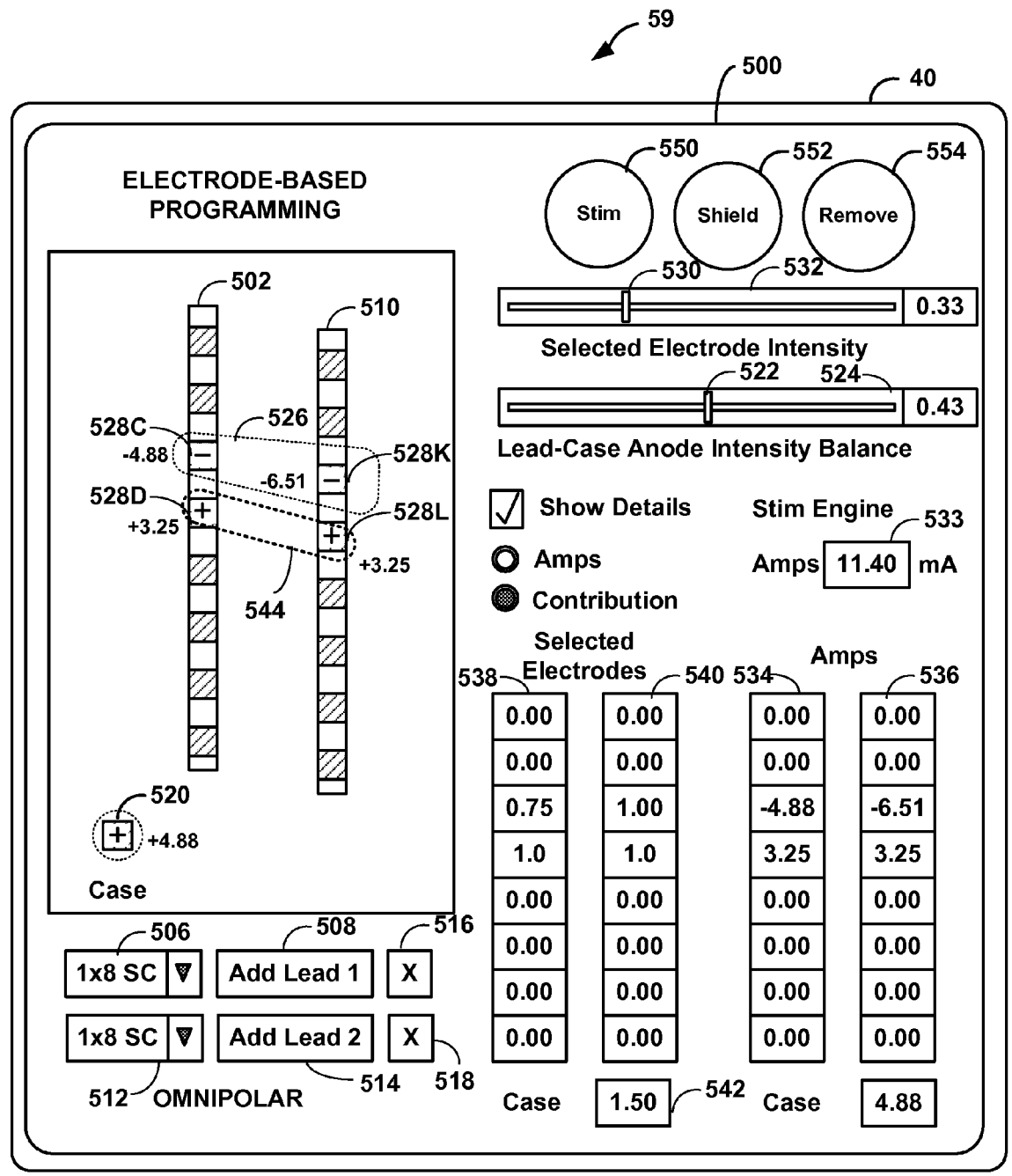

FIG. 20 depicts a user interface illustrating a hybrid, or omnipolar, electrode arrangement that makes use of various combinations of unipolar and bipolar relationships between the electrodes, in accordance with the techniques described above, created using electrode-based programming. FIG. 20 depicts user interface 59 provided by programmer 40, similar to that shown in FIGS. 18-19.

In order to select an omnipolar stimulation arrangement, a user may first use a stylus to move indicator 522 along horizontal scroll bar 524 until the Lead-Case Anode Intensity Balance indicates a value between 1.0, or unipolar, and 0.0, or bipolar/multipolar. As shown in FIG. 20, the Lead-Case Anode Intensity Balance indicates a value of 0.43, approximately equally balanced between a unipolar and bipolar/multipolar stimulation arrangement. Next, in order to create the desired fields 526, 546 as in FIG. 20, a user may use a stylus, for example, and touch the electrodes depicted on leads 502, 510 that the user seeks to create fields 526, 546. The user may then use a stylus to move indicator 530 along horizontal scroll bar 532 to select the desired electrode intensity.

In FIG. 20, the Selected Electrode Intensity is 0.33, which is used to scale the electrode contributions by the desired intensity to get amplitude outputs in stimulation current. The Selected Electrode Intensity of 0.33 equates in this example to 11.4 mA of overall current stimulation, as indicated in current window 533. Upon selecting the desired electrode intensity, processor 53 of programmer 40 generates fields 526, 546 and depicts the currents associated with the selected electrodes that are needed to generate fields 526, 546. As shown in FIG. 20, electrodes 528D and 528L, configured as anodes, source 3.25 mA and 3.25 mA (a total of 6.5 mA), respectively. Electrodes 528C and 528K, configured as cathodes, sink 4.88 mA and 6.51 mA (a total of 11.4 mA with a small rounding error), respectively. The remaining current, 4.88 mA, is sourced by case electrode 520. The currents needed to generate fields 526, 546 are shown in window 504 as well as in arrays 534, 536, which depict each of the electrodes on each of the two leads and the current in milliamps associated with the electrodes originally selected by the user.

In addition, arrays 538, 540 indicate the contributions of the electrodes originally selected by the user. In the example depicted in FIG. 20, the selected electrode that sinks (or sources) the most current to produce a given field has a first contribution of 1.0, and the contributions of the remaining electrodes used to produce that particular field are a percentage of that first contribution. In FIG. 20, electrode 528K sinks 6.51 mA, a value greater than the 4.88 mA sunk by electrode 528C. As such, electrode 528K has a contribution of 1.0, and electrode 528C has a contribution of 4.88 mA/6.51 mA or about 0.75, as indicated in arrays 538, 540. Similarly, electrode 528D sources 3.25 mA, a value equal to the 3.25 mA sourced by electrode 528L. As such, electrodes 528D, 528L each have a contribution of 1.0, as indicated in arrays 538, 540. The current sourced by case electrode 520 is compared to the contributions by the other anodes. As seen in FIG. 20, case electrode has a contribution of 4.88 mA/3.25 mA, or 1.50, as indicated at 542.

The programming techniques discussed above with respect to FIGS. 18-20 may provide a convenient and efficient mechanism to balance different omnipolar current distributions and electrode combinations and evaluate the results. The techniques may allow a user to transition between a stimulation setting that uses a unipolar electrode arrangement to a stimulation setting that uses a bipolar electrode arrangement, and permit a range of hybrid electrode arrangements that make use of various combinations of unipolar and bipolar relationships between the electrodes.

Figure 21:
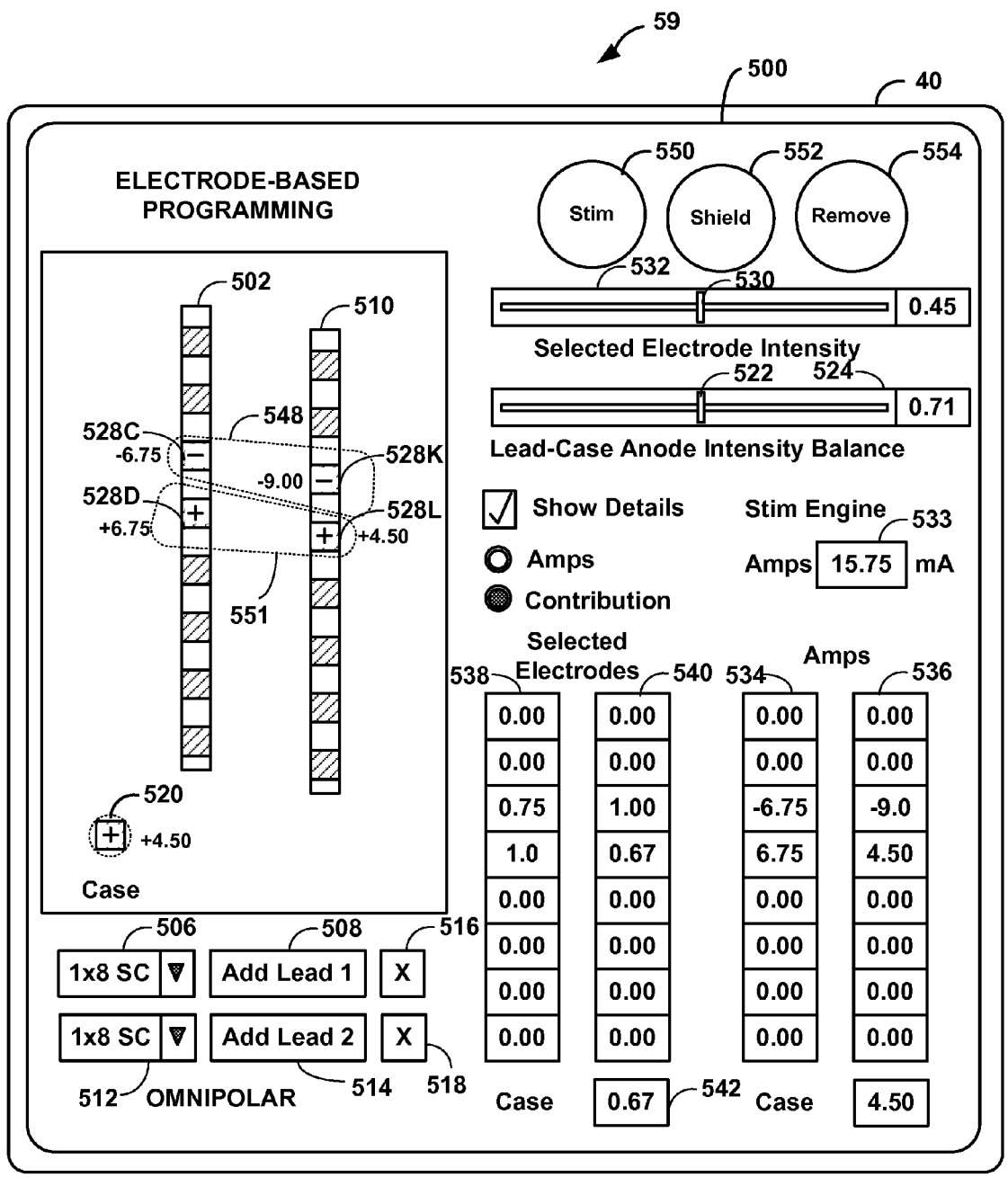

FIG. 21 depicts a user interface illustrating another hybrid, or omnipolar, electrode arrangement that makes use of various combinations of unipolar and bipolar relationships between the electrodes, in accordance with the techniques described above, created using electrode-based programming. FIG. 21 depicts user interface 59 provided by programmer 40, similar to that shown in FIGS. 18-20.

As shown in FIG. 21, the Lead-Case Anode Intensity Balance indicates a value of 0.71, indicating that the balance of the stimulation arrangement has been shifted toward a unipolar stimulation arrangement. As before, in order to create the desired fields 548, 551 as in FIG. 21, a user may use a stylus, for example, and touch the electrodes depicted on leads 502, 510 that the user seeks to create fields 548, 551. The user may then use a stylus to move indicator 530 along horizontal scroll bar 532 to select the desired electrode intensity. In FIG. 21, the Selected Electrode Intensity has been increased to 0.45, which is used to scale the electrode contributions by the desired intensity to get amplitude outputs in stimulation current. The Selected Electrode Intensity of 0.45 equates in this example to 15.75 mA of overall current stimulation, as indicated in current window 533. Upon selecting the desired electrode intensity, processor 53 of programmer 40 generates fields 548, 551 and depicts the currents associated with the selected electrodes that are needed to generate fields 548, 551. As shown in FIG. 21, electrodes 528D and 528L, configured as anodes, source 6.75 mA and 4.50 mA (a total of 11.25 mA), respectively. Electrodes 528K and 528C, configured as cathodes, sink 9.00 mA and 6.75 mA (a total of 15.75 mA), respectively. The remaining current, 4.50 mA, is sourced by case electrode 520. The currents needed to generate fields 548, 551 are shown in window 504 as well as in arrays 534, 536, which depict each of the electrodes on each of the two leads and the current in milliamps associated with the electrodes originally selected by the user.

In addition, arrays 538, 540 indicate the contributions of the electrodes originally selected by the user. In FIG. 21, electrode 528K sinks 9.00 mA, a value greater than the 6.75 mA sunk by electrode 528C. As such, electrode 528K has a contribution of 1.0, and electrode 528C has a contribution of 6.75 mA/9.00 mA or about 0.75, as indicated in arrays 538, 540. Similarly, electrode 528D sources 6.75 mA, a value greater than the 4.50 mA sourced by electrode 528L. As such, electrode 528D has a contribution of 1.0, and electrode 528L has a contribution of 4.50 mA/6.75 mA or about 0.67, as indicated in arrays 538, 540. The current sourced by case electrode 520 is compared to the contributions by the other anodes. As seen in FIG. 21, case electrode delivers the same amount of current as electrode 528L and, as such, has a contribution of 0.67, as indicated at 542.

Figure 22:
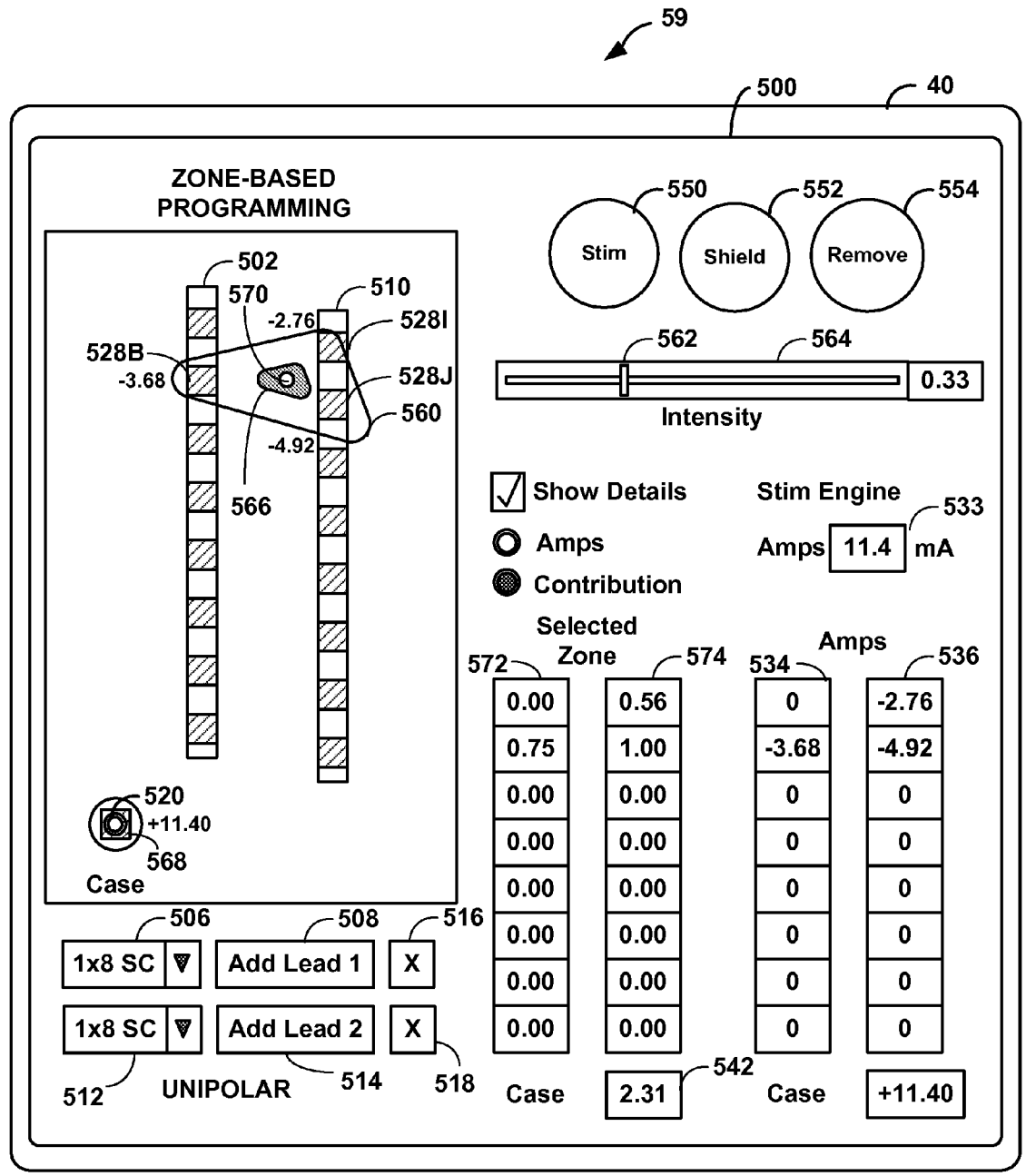

FIG. 22 depicts a user interface illustrating a unipolar stimulation arrangement created using zone-based programming, in contrast to the electrode-based programming shown in FIGS. 18-21. In zone-based programming, a user may graphically define a desired stimulation field(s) within zones on or adjacent to one or more leads, and processor 53 of programmer 40 may generate the current stimulation required to create the stimulation field.

FIG. 22 depicts user interface 59 provided by programmer 40, similar to that shown in FIGS. 18-21. User interface 59 includes stimulation icon 550, shield icon 552, and removal icon 554 that may be used to create a desired stimulation field(s), as will be described in more detail below. User interface 59 includes display screen 500. Display screen 500 may be a touchscreen such that a stylus or other pointing media may be used to make selections directly on screen 500. Alternatively, or in addition, keys, buttons, wheels and other input devices may be provided on programmer 40, independently of display 500.

As described previously, first lead 502 may be added to window 504 by first selecting a desired type of lead from pull-down menu 506 and then selecting "Add Lead 1" via icon 508. Similarly, second lead 510 may be added to window 504 by selecting the type of lead from pull-down menu 512 and then selecting "Add Lead 2" via icon 514. Leads may be added to window 504 by using a stylus, for example, and touching a location in the window for placement of the leads. In addition, the user may drag the leads placed in window 504 to a desired location. Icons 516, 518 allow a user to remove a lead from window 504. The housing electrode, or "case" electrode, indicated at 520 may, in some examples, be permanently displayed in window 504.

In order to create field 560, as in FIG. 22, a user may use a stylus, for example, and touch stimulation ("Stim") icon 550. The user may then use the stylus and touch a location, or zone, within window 504. For example, the user may touch an electrode on one of leads 502, 510, or a location near one of the electrodes or leads, e.g., between electrodes and leads. Touching an electrode with the stylus places a stimulation field on the selected zone, e.g., the lead at the electrode. Touching an area or zone between a lead or electrode places a stimulation field on the selected zone, i.e., between the lead or electrode. Individual electrode values may be determined by their relative proximity to the location of the placed field such that the nearest electrode is a full contributor (1.0) and others are scaled proportionally. The user may shape, move, shrink, and expand the stimulation field by dragging, for example, the stimulation field via the stylus to other areas, or zones, in window 504, e.g., electrodes or areas adjacent to electrodes, in order to create the desired shape of stimulation field 560. Touching removal icon 554 with a stylus will remove the stimulation field.

After a zone has been placed on the display screen, programmer 40 and in particular processor 53 recruits a set of electrodes, e.g., up to four electrodes, to generate the zone. In some examples, one or more electrodes may be recruited based on their relative distance from the placed zone such that their contributions are greater than a minimum threshold. The electrodes recruited by a zone may have independent contributions to the shape of the zone between 0 and 1.0, dependent on the relative distance from the electrode to the zone center. Electrode contributions may be scaled on a per zone basis such that the highest contributing electrode(s) are 1.0 and all others are less than or equal to 1.0.

In some examples the scaling of electrodes may be accomplished by finding the distance between the selected zone placement point and all electrode centers of leads in the lead placement region. The four shortest distances that do not cause a lead to be crossed are then selected for recruitment. Contributions are determined by finding the distance from the point to the recruited electrodes as a ratio of the total distance between electrodes separately in the x and y dimensions.

Figure 23:
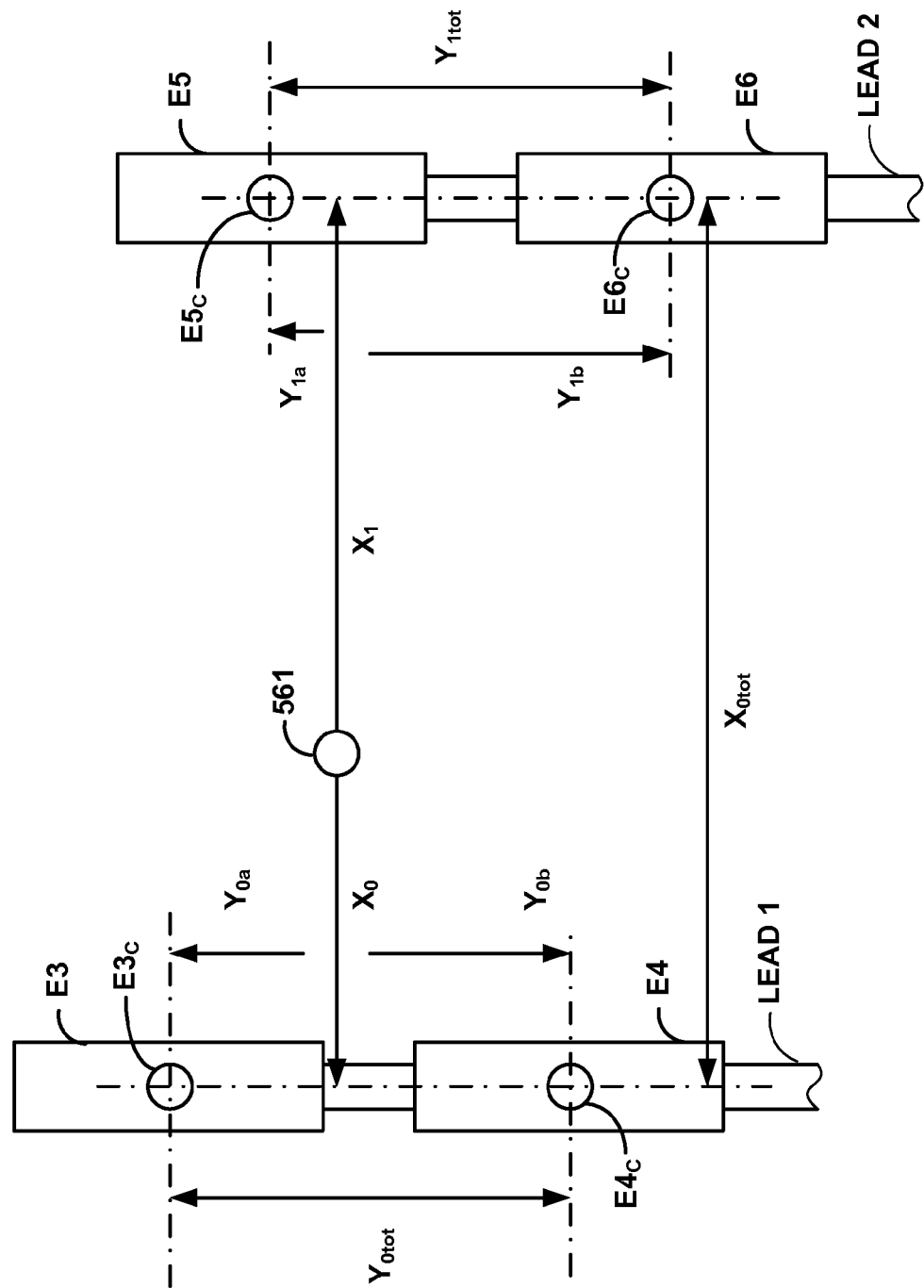
FIG. 23 is a schematic illustrating an example electrode contribution determination.

FIG. 23 is a schematic illustrating an example electrode contribution determination. In FIG. 23, the contributions of electrodes E3 and E4 on lead 1 (the left lead) and electrodes E5 and E6 on lead 2 (the right lead) are determined by finding the distance from the selected zone placement point, shown at 561, as a ratio of the total distance between the centers of the electrodes, separately in the x and y dimensions. The centers of electrodes E3, E4, E5, and E6 are shown in FIG. 23 at $E3_C$, $E4_C$, $E5_C$, and $E6_C$, For lead 1 (the left lead), the electrode contributions are determined as follows:

$$E3=(X_1/X_{tot})*(Y_{0b}/(Y_{0tot})$$

$$E4=(X_1/X_{tot})*(Y_{0a}/(Y_{0tot})$$

And, for lead 2 (the right lead), the electrode contributions are determined as follows:

$$E5=(X_0/X_{tot})*(Y_{1b}/Y_{1tot})$$

$$E6=(X_0/X_{tot})*(Y_{1a}/Y_{1tot})$$

The user may then use a stylus to move indicator 562 along horizontal scroll bar 564 to select the desired electrode intensity. Referring again to FIG. 22, the Selected Zone Intensity is 0.33, which is used to scale the electrode contributions of electrodes automatically selected to create stimulation field 560 by the desired intensity to generate stimulation current amplitudes. Moving indicator 562 may modify all of the electrodes associated with a placed field or zone together. In addition, the intensity of the stimulation field is graphically depicted at 566. The Selected Zone Intensity of 0.33 equates in this example to 11.4 mA of overall current stimulation, as indicated in current window 533. As indicator 562 of horizontal scroll bar 564 is moved to the right, the intensity is increased, depicted graphically at 566 and as indicator 562 of horizontal scroll bar 564 is moved to the left, the intensity is decreased. In some examples, the intensity of case electrode 520 may be automatically set in order to balance the other currents. In other examples, the user may explicitly set the intensity of case electrode 520. In one example, case electrode 520 may be automatically configured as an anode, and the user may explicitly increase or decrease its intensity using horizontal scroll bar 564 in the manner described above. The intensity of case electrode 520 is graphically illustrated at 568. Upon selecting the desired electrode intensity, processor 53 of programmer 40 generates and depicts the current amplitudes associated with the desired field 560, as seen in window 504. In another example, the user may specify whether case electrode 520 is an anode or cathode by selecting either the shield or sink icon, respectively, dragging the field, and then setting the intensity via horizontal scroll bar 564.

A user may shape the stimulation field by dragging, for example, the stimulation field boundaries via the stylus to other areas in window 504. For example, the user may click on a border, i.e., an outer perimeter, or an area near the border, of the stimulation field, and drag it inward or outward to resize the stimulation field. When a user clicks on the stimulation field border and drags it, the stimulation field may, for example, expand in the direction in which the user drags the stimulation field.

In addition to shaping the stimulation field by dragging, for example, the stimulation field boundaries via the stylus to other areas in window 504, the center of stimulation field 560 may be moved by dragging, for example, icon 570 representing the intensity of the stimulation field. Dragging center icon 570 of stimulation field 560 may result in the entire stimulation field moving in the direction in which the user drags the stimulation field. Dragging the stimulation field may result in adjustments to the currents sunk (or sourced) by the electrodes producing stimulation 560.

Unlike the examples shown in FIGS. 18-21, zone-based programming displays may not include a horizontal scroll bar for controlling Lead-Case Anode Intensity Balance. Rather, the system automatically determines the contributions of the three electrodes on the lead, 0.56, 0.75, and 1.00, shown in arrays 572, 574, which depict each of the zones on each of the two leads. Individual electrode values may be determined by their relative proximity to the location of the placed field such that the nearest electrode is a full contributor (1.0) and others are scaled proportionally. The system then scales the contributions by the desired intensity to generate stimulation current amplitudes. The system then defaults to a unipolar mode, and activates case electrode 520 to balance the sum of the three electrodes activated (4.92 mA+3.68 mA+2.76 mA=11.35 mA, with a small rounding error). This may be advantageous because it may require fewer user actions, e.g., the system automatically configures the case electrode, and may eliminate the need for user interactions on subsequent intensity changes, e.g., the user does not have to balance stimulation in order for the system to enter a valid, programmable state. The system may also default to the most energy efficient mode such that losses in the lead array are only applied once, because the return path does not traverse the lead array wires a second time.

As shown in FIG. 22, case electrode 520 sources the desired 11.4 mA of current while electrodes 528I, 528B, 528J sink 2.76 mA, 3.68 mA, and 4.92 mA, respectively. The currents needed to generate field 560 are shown in window 504 as well as in arrays 534, 536, which depict each of the electrodes on each of the two leads and the current in milliamps associated with the electrodes within the zones originally selected by the user. In addition, arrays 572, 574 indicate the contributions of the electrodes in the zone(s) originally selected by the user. In the example depicted in FIG. 22, the electrode that sinks (or sources, in other examples) the most current to produce a given field has a first contribution of 1.0, and the contributions of the remaining zones used to produce that particular field are a percentage of that first contribution. In FIG. 22, electrode 528J sinks 4.92 mA, a value greater than the currents sunk by electrodes 528B, 528I. As such, electrode 528J has a contribution of 1.0, and electrodes 528B, 528I have a contribution of 3.68 mA/4.92 mA or about 0.75 and 2.76 mA/4.92 mA, respectively, as indicated in arrays 572, 574. In a unipolar arrangement, like in FIG. 22, case electrode 568 must source all of the desired current and, as such, it has a contribution of 1.0+0.75+0.56=2.31, as indicated at 542.

Figure 24:
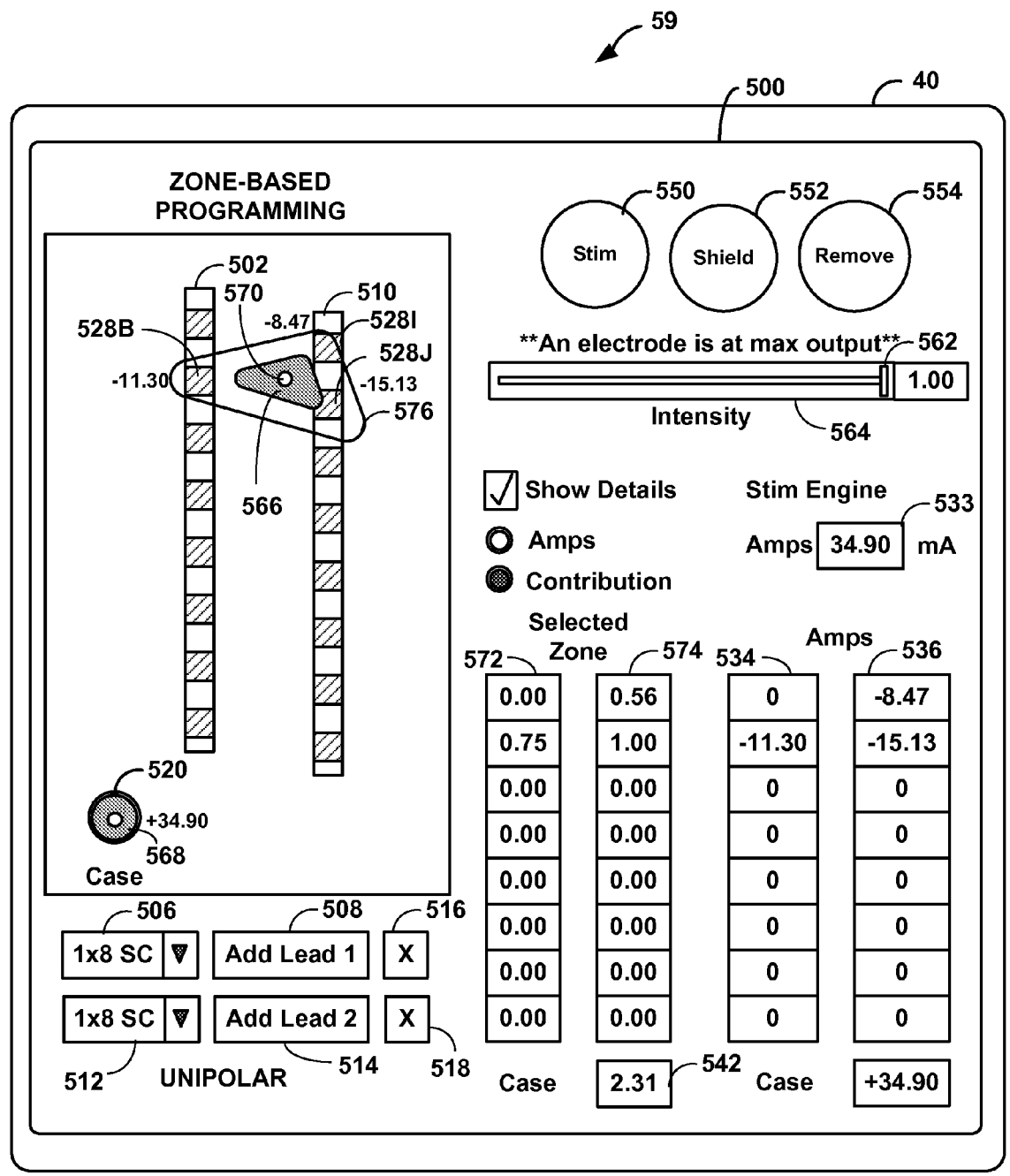
FIGS. 24-26 are schematic diagrams illustrating example user interfaces presented by the programmer of FIG. 4.

FIG. 24 depicts a user interface illustrating another unipolar stimulation arrangement created using zone-based programming. FIG. 24 is similar to the user interface described above with respect to FIG. 22. In FIG. 24, however, indicator 562 of horizontal scroll bar 564 has been moved all the way to the right, thereby maximizing electrode intensity at 1.0 for a selected electrode, creating stimulation field 576. In FIG. 24, case electrode has been selected to operate at maximum intensity. Maximum intensity may be indicated, for example, by a text message. In FIG. 24, the text message states "An electrode is at max output." In other words, one of the electrodes (here, case electrode 520) is stimulating at, or near, its maximum of 35 mA. The intensity of case electrode 520 is graphically illustrated at 568. The increased intensity of stimulation field 576 is shown graphically at 566.

Figure 25:
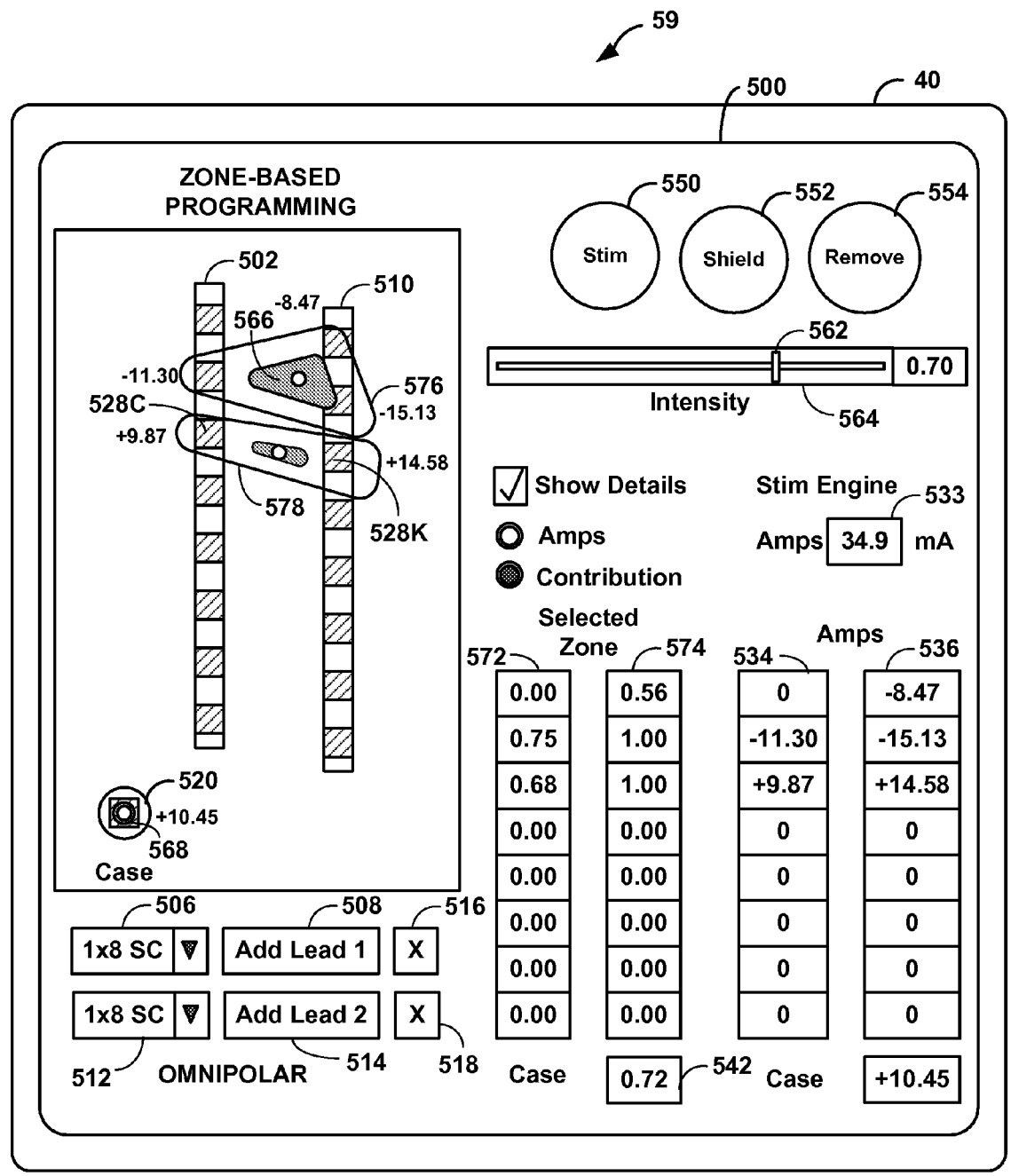

In this condition, or in a condition where the user desires to place an anode on the lead array to affect the stimulation field or to guard a physiological structure such as a dorsal root by causing its neurons to be hyperpolarized, for example, an anodal 'shield' zone can be placed on the lead array, as will be described in more detail with respect to FIG. 25. For example, a user may use a stylus, for example, and touch shield ("Shield") icon 552. The user may touch an electrode on one of leads 502, 510. Touching an electrode with the stylus places an anodal shield zone on the lead at the electrode. The anodal shield zone may then be shaped by dragging, for example, the shield zone via the stylus to other areas in window 504, e.g., electrodes, in order to create the desired shape. Similar to the stimulation field, the intensity of the anodal shield zone may be increased or decreased by selecting the electrode or electrode combination and moving indicator 562 along horizontal scroll bar 564 to select the desired electrode intensity. As the anodal shield zone is increased in intensity, for example, the system can continue to automatically balance the stimulation by preferentially modifying case electrode 520 to balance the more therapeutic lead electrodes such that net output current is zero, i.e., current sourced by anodes equals current sunk by cathodes, as seen in FIG. 25. Thus, after receiving user input specifying an adjustment to at least one electrode (e.g., dragging a stimulation field and/or anodal shield zone), the system may automatically determine for each electrode not adjusted by the user input, an amount of electrical stimulation current such that the sum of the electrical stimulation currents to be supplied by each of the first, second, and third electrodes equals zero. Then, the system may define a new program to control delivery of the electrical stimulation by the stimulator based on the automatically determined amounts of electrical stimulation currents. In this manner, the system may automatically balance, or re-balance, electrical stimulation currents after a user makes changes to a stimulation field and/or an anodal shield zone.

FIG. 25 depicts a user interface illustrating a hybrid, or omnipolar, electrode arrangement that makes use of various combinations of unipolar and bipolar relationships between the electrodes, in accordance with the techniques described above, created using zone-based programming. In FIG. 25, the system is operating in a dual mode fashion, such that stimulation is partially unipolar and partially bipolar/multipolar in nature. FIG. 25 depicts the original stimulation field 576 shown in FIG. 24. In addition, anodal shield zone 578 is depicted in FIG. 25 with the currents associated with the electrodes required to create shield zone 578. By moving indicator 562 along horizontal scroll bar 564 to increase the desired electrode intensity of the electrodes used to create shield zone 578, the currents associated with the electrodes required to create shield zone 578 also increase.

As mentioned above, as anodal shield zone 578 increases in intensity, the system can continue to automatically rebalance the stimulation such that net output current is zero by decreasing the amount of current sourced by case electrode 520. For example, in FIG. 24, the stimulation zone currents of 8.47 mA, 11.30 mA, and 15.13 mA were balanced by case electrode current of 34.90 mA. In FIG. 25, the addition of anodal shield zone 578 and its associated currents of 9.87 mA and 14.58 mA from electrodes 528C and 528K, respectively, require a corresponding drop in the current sourced by case electrode 520 in order to maintain the system balance. In particular, case electrode 250 decreases by 9.87 mA+15.58 mA=24.45 mA to 10.45 mA. In this manner, the system transitions from operating in a unipolar stimulation arrangement, as in FIG. 24, to operating in a dual mode fashion such that stimulation is partially unipolar and partially bipolar/multipolar in nature. That is, current is sourced by anodes on the lead substantially simultaneously with current sourced by the case electrode.

Figure 26:
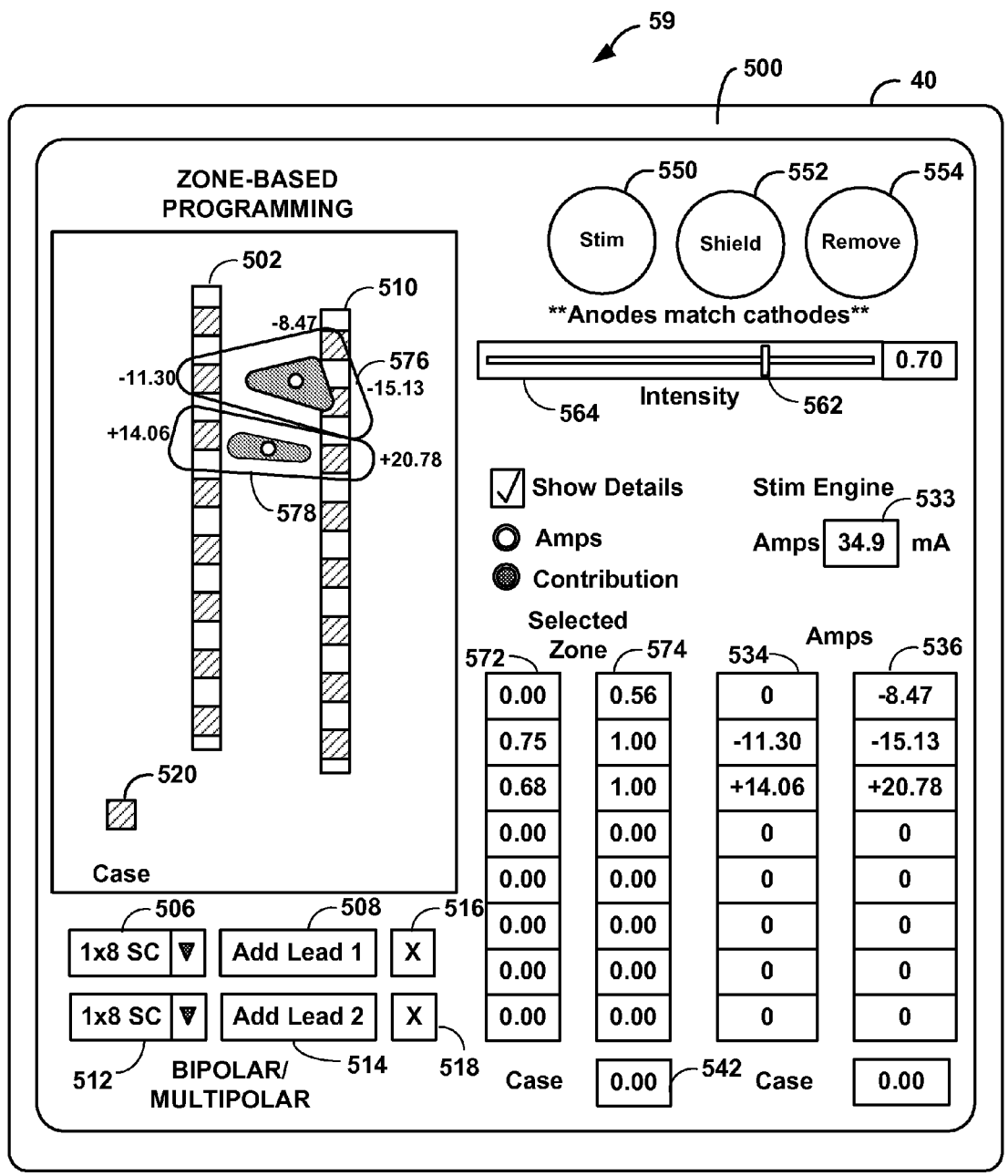

FIG. 26 depicts a user interface illustrating a bipolar/multipolar stimulation arrangement created using zone-based programming. In particular, as the intensity of anodal shield zone 578 is increased, the utilization of case electrode 520 decreases until it is eventually turned off, as shown in FIG. 26. In FIG. 26, a current of 0.06 mA ((14.06 mA+20.78 mA)−(8.47 mA+11.30 mA+15.13 mA)) sourced by case electrode is insignificant and, as such, may be turned off to maintain efficiency. The system is now operating in a fully bipolar/multipolar mode. The user may receive an indication that the system has transitioned to a bipolar/multipolar via text message. For example, FIG. 26 displays a text message indicating that "Anodes match cathodes."

Thus, in the manner shown in FIGS. 18-26, the techniques of this disclosure allow a user to transition between a stimulation setting that uses a unipolar electrode arrangement to a stimulation setting that uses a bipolar electrode arrangement, and permit a range of hybrid electrode arrangements that make use of various combinations of unipolar and bipolar relationships between the electrodes.

It should be noted that, in some examples, it may be possible to continue increasing the anodal shield zone such that case electrode 520 is driven into a cathodal stimulation mode. That is, although the case electrode, in general, acts as an additional anodal current source in the examples described above, in some examples, the case electrode may act as a cathodal current sink, provided that stimulation at the case remains at a subthreshold or otherwise innocuous level. Such a configuration may result in a small, focused area of stimulation on the lead(s) surrounded by strong anodal shields. In addition, it should be noted that each time the intensity, zone, field, or any other parameter is adjusted via the programmer, these adjustments may be applied to the patient by downloading the necessary programs, commands, and/or adjustments to the implantable stimulator, e.g., implantable stimulator 34, by wireless telemetry. The results of the adjustments may then be evaluated, e.g., to determine efficacy.

The programming techniques discussed above with respect to FIGS. 22-26 may provide a convenient and efficient mechanism to balance different omnipolar current distributions and electrode combinations and evaluate the results. The techniques may allow a user to transition between a stimulation setting that uses a unipolar electrode arrangement to a stimulation setting that uses a bipolar electrode arrangement, and permit a range of hybrid electrode arrangements that make use of various combinations of unipolar and bipolar relationships between the electrodes.

It should be noted that an omnipolar stimulation arrangement may deliver omnipolar electrical stimulation over an entire pulse or over only a portion of a pulse. For example, the first half of a pulse may deliver electrical stimulation using an omnipolar stimulation arrangement and the second half of the pulse may deliver electrical stimulation using a bipolar/multipolar arrangement. By way of specific example, assume a 200 microsecond pulse may be divided into a first half of 100 microseconds and a second half of 100 microseconds. During the first half of the pulse, i.e., the first 100 microseconds, the housing electrode may source, i.e., as an anode, 4 mA, a first electrode on a lead may source 1 mA, a second electrode on a lead may sink 6 mA, and a third electrode on a lead may source 1 mA. The first, second, and third electrodes may be on the same lead or multiple leads. Then, during the second half of the pulse, i.e., the second 100 microseconds, the housing electrode may be turned off, the first electrode may source, i.e., as an anode, 3 mA, the second electrode may sink 6 mA, and the third electrode may source 3 mA. In this manner, only a portion of a pulse is delivered via an omnipolar stimulation arrangement.

Figure 27:
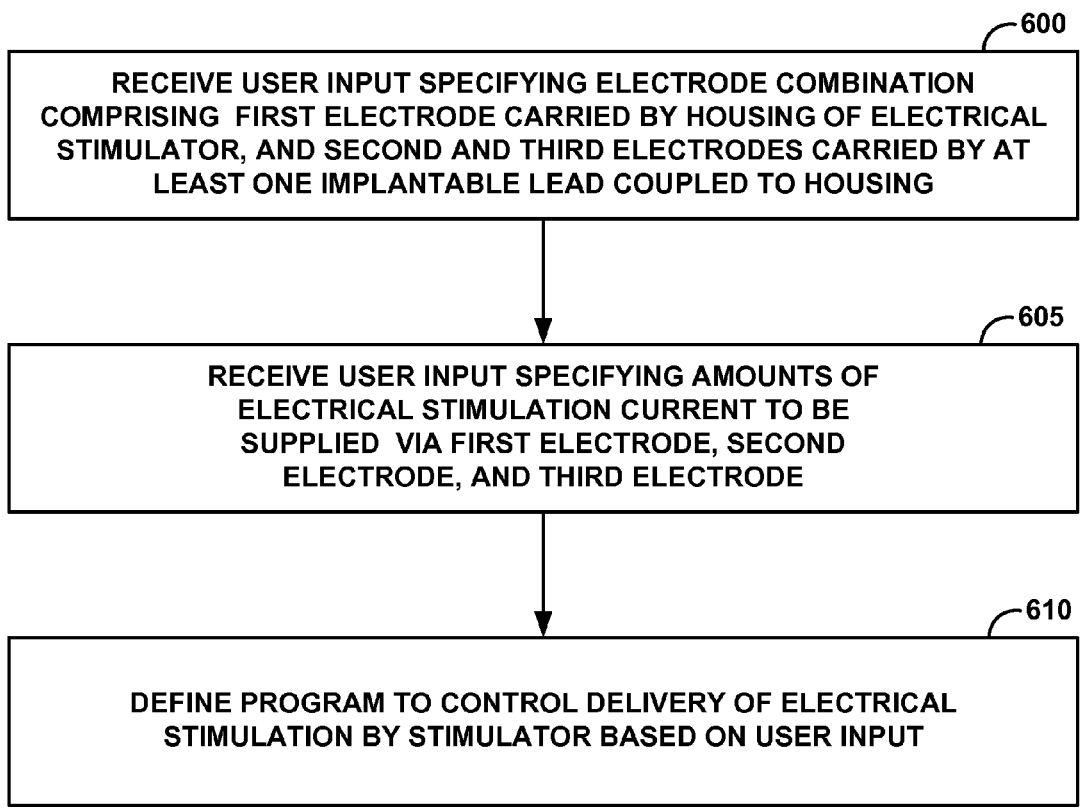
FIG. 27 is a flow diagram illustrating example operation of the programmer for generating a program to control delivery of electrical stimulation.

FIG. 27 is a flow diagram illustrating example operation of the programmer for generating a program to control delivery of electrical stimulation. In FIG. 27, a programmer, e.g., external programmer 40, receives, via user interface 59, user input specifying an electrode combination for delivery of electrical stimulation from an electrical stimulator to a patient. The electrode combination comprises at least a first electrode carried by a housing of the electrical stimulator, e.g., case electrode 520, and a second electrode and a third electrode carried by at least one implantable lead, e.g., leads 502, 510, a coupled to the housing (600). The second electrode and the third electrode may be carried by the same lead, or by two different leads. For example, electrodes 528A and 528B may form the second and third electrodes, respectively, or electrodes 528A and 528I may form the second and third electrodes, respectively. In some examples, the first electrode is an anode, the second electrode is an anode, and the third electrode is a cathode. In other examples, the first electrode is a cathode, the second electrode is a cathode, and the third electrode is an anode. In some examples, specifying an electrode combination comprises using a pointing media to select electrodes of the electrode combination. In other examples, specifying an electrode combination comprises drags a stimulation field relative to the one or more leads. The user may additionally add and drag a shield zone relative to the at least one lead.

Additionally, a programmer, e.g., external programmer 40, may receive, via user interface 59, user input specifying amounts of electrical stimulation current to be supplied via the first electrode, the second electrode, and the third electrode. For example, a user may select an electrode and then slide indicator 530 along horizontal scroll bar 532 in order to specify the amounts of current to be supplied by each one of the first, second, and third electrodes (605). For example, specifying the amounts of current may comprise specifying a balance of current between the first electrode, the second electrode, and the third electrode. Specifying the amounts of current may include applying current levels explicitly, e.g., entering numeric values, using a slider bar, e.g., a vertical or horizontal scroll bar, by resizing or reshaping a zone, or by other means. The balance of current may comprise an indication of weights assigned to the first electrode, the second electrode, and the third electrode. In some examples, the weights are assigned to the first electrode, the second electrode, and the third electrode by adjusting a slidable medium within a range, for example indicator 530 of horizontal scroll bar 532.

Finally, the programmer, and in particular processor 53, may define a program to control delivery of the electrical stimulation by the stimulator based on the user input received via user interface 59 (610). The program may include the electrode combinations specified as well as stimulation parameters such as duration, current or voltage amplitude, pulse width and pulse rate. The programmer may then download the program to the stimulator to deliver stimulation.

Figure 28:
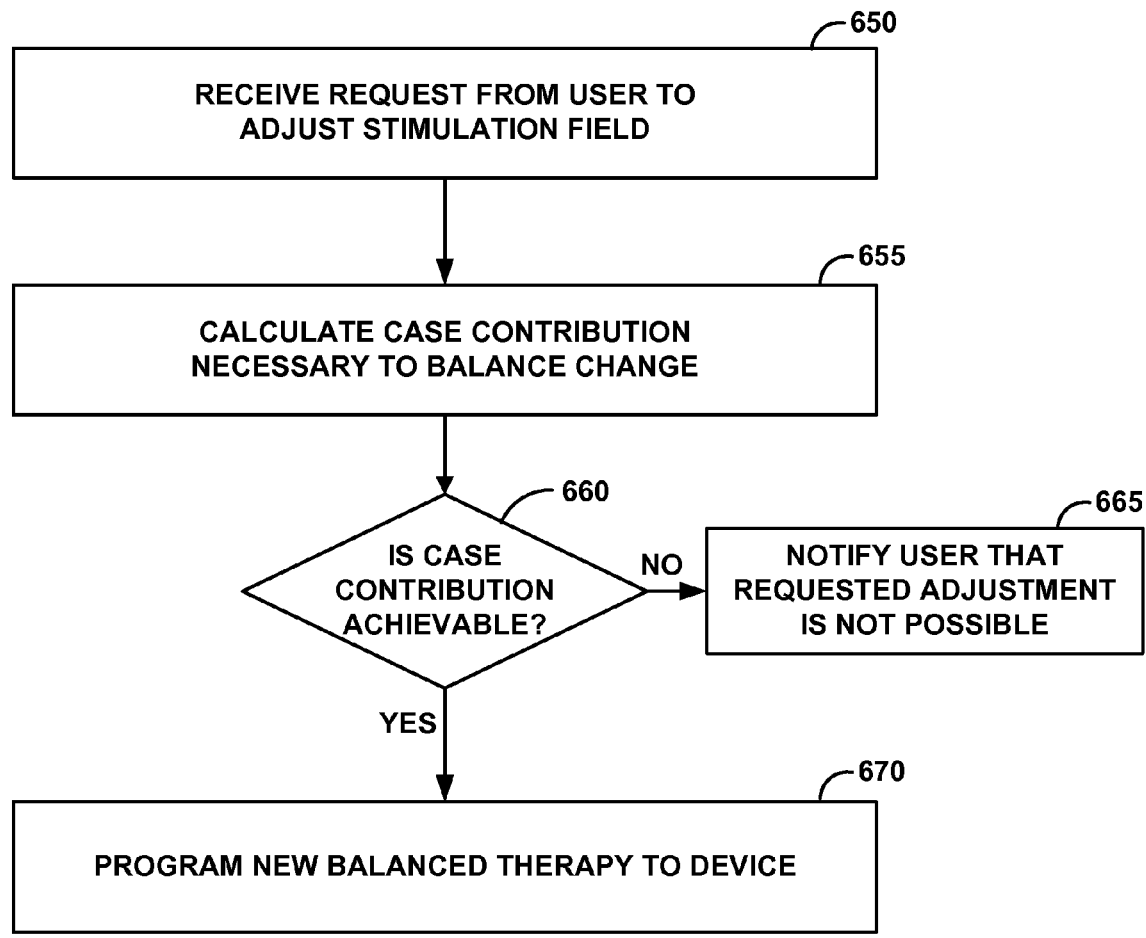
FIG. 28 is a flow diagram illustrating another example operation of the programmer for generating a program to control delivery of electrical stimulation.

FIG. 28 is a flow diagram illustrating another example operation of the programmer for generating a program to control delivery of electrical stimulation. FIG. 28 depicts an example in which stimulation is automatically balanced after a user adjusts one or more aspects of stimulation, e.g., a change in one or more electrode contributions, a change in the intensity of one or more aspects of a field, or other changes that would result in unbalanced stimulation. A programmer, e.g., external programmer 40, may receive a request from a user via user interface 59 to adjust a stimulation field (650). In response, the programmer, and in particular processor 53, calculates the case electrode contribution necessary to balance the change caused by the requested adjustment (655). Processor 53 may, for example, compare the calculated case contribution with a case contribution threshold value in order to determine if the case contribution calculated is achievable (660). If the calculated case contribution is not achievable, e.g., the calculated case contribution exceeds the threshold value ("NO" at block 660), the user is notified, e.g., via user interface 59, that the requested adjustment is not possible (665). If the calculated case contribution is achievable, e.g., the calculated case contribution does not exceed the threshold value ("YES" at block 660), then the programmer programs the new balanced therapy to the device. The adjustment requested by the user may result, for example, in case electrode 520 sourcing more or less current, changing from an anode (source) to a cathode (sink), or turning off, e.g., if the current sourced or sunk by the case electrode after the user adjustment is approximately zero or otherwise insignificant.

Figure 29:
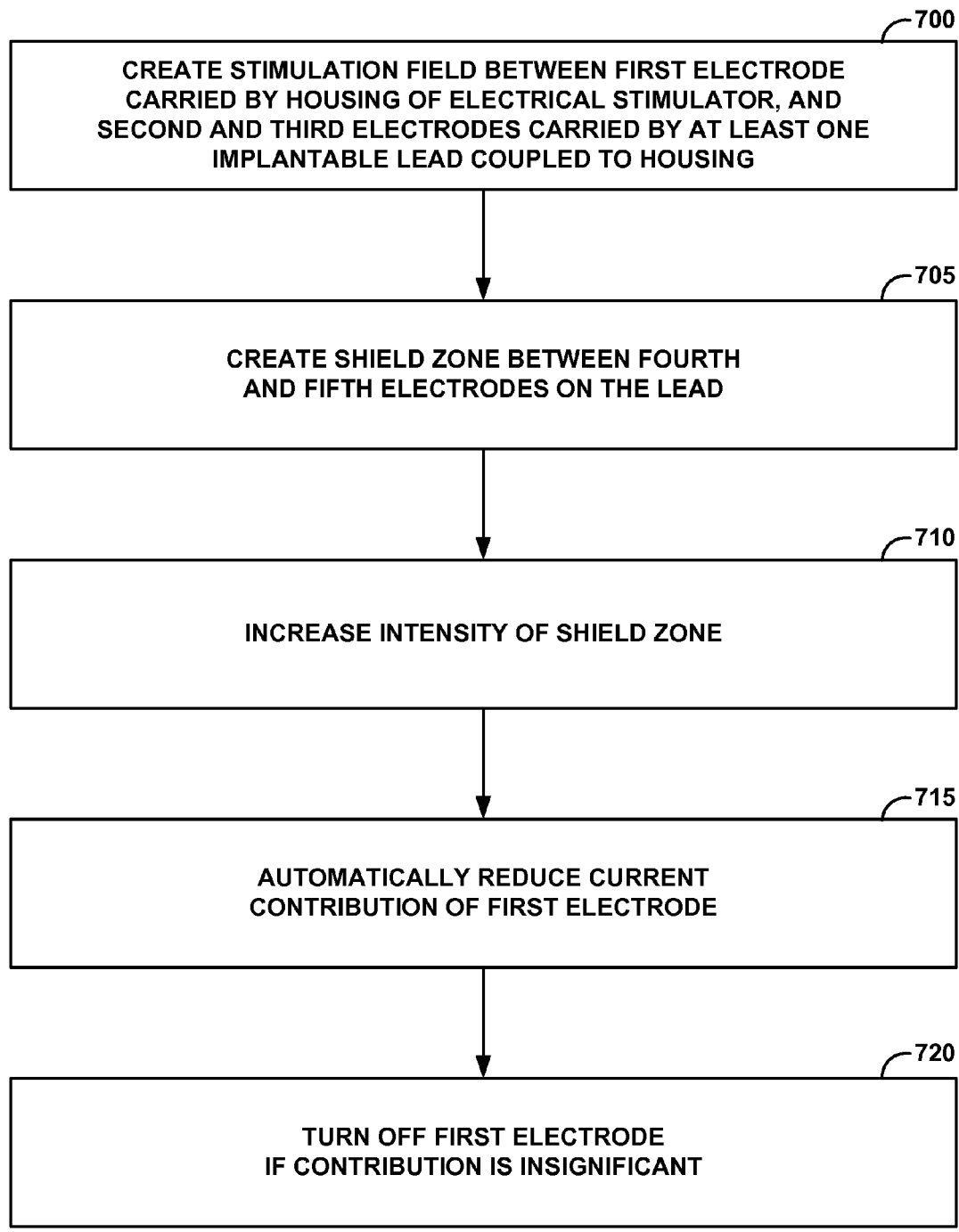
FIG. 29 is a flow diagram illustrating example operation of the programmer for transitioning from a unipolar stimulation arrangement to a hybrid stimulation arrangement, and finally to a bipolar or multipolar stimulation arrangement.

FIG. 29 is a flow diagram illustrating example operation of the programmer for transitioning from a unipolar stimulation arrangement to a hybrid stimulation arrangement, and finally to a bipolar or multipolar stimulation arrangement. Using user interface 59 of programmer 40, for example, a user creates a stimulation field between a first electrode carried by the housing of the electrical stimulator, e.g., case electrode 520, and a second and third electrodes carried by one or more implantable leads, e.g., leads 502, 510, coupled to the housing (700). In this arrangement, the system is configured to perform in a unipolar stimulation arrangement. The user may then use user interface 59 to create an anodal shield zone, e.g., shield zone 578, between a fourth and fifth electrode on the one or more leads (705).

In this arrangement, the system is configured to perform in a dual mode, using aspects of both unipolar stimulation and bipolar/multipolar stimulation. As the user increases the intensity of the shield zone (710), e.g., by sliding indicator 562 along horizontal scroll bar 564, the system automatically reduces the current contribution of the first electrode, e.g., case electrode 520 (715). The system may turn off the current contribution of the first electrode when that contribution is insignificant, i.e., when it falls below a minimum threshold. In this arrangement, the system is now configured to perform only in a bipolar/multipolar arrangement because the case electrode has been turned off. Thus, the system may be configured in a unipolar stimulation arrangement, transition to a hybrid configuration in which aspects of both unipolar stimulation and bipolar/multipolar stimulation are used to provide an overall effect to a patient, and then finally transition to a bipolar/multipolar stimulation configuration. Although the above description begins with a unipolar arrangement and finishes with a bipolar/multipolar arrangement, the reverse is also contemplated. That is, the system may be configured in a bipolar/multipolar stimulation arrangement, transition to a hybrid configuration in which aspects of both unipolar stimulation and bipolar/multipolar stimulation are used to provide an overall effect to a patient, and then finally transition to a unipolar stimulation configuration.

Various techniques have been described above that substantially simultaneously deliver electrical stimulation via one or more electrodes on an implantable medical device (IMD) housing and two or more electrodes on one or more leads coupled to the housing. As described in detail above, the one or more housing electrodes may be configured to deliver electrical stimulation and automatically balance stimulation currents delivered by two or more lead electrodes to produce valid stimulation settings. Such configurations may require fewer electrode specifications from a user. Similar automatic balancing may be achieved utilizing various other configurations, as will be described in detail below.

For example, rather than utilizing one or more housing electrodes to automatically balance the stimulation currents delivered by two or more selected (e.g., user selected via lead or zone-based programming as described herein) electrodes on one or more leads as described above, one or more other non-selected electrodes, may be automatically configured to deliver balancing current. The term "selected" electrode as described herein refers to an electrode selected by a user to perform a specific purpose such as to generate a stimulation field or shield zone in patient tissue. The term "non-selected" as described herein refers to an electrode not selected by a user to perform a specific purpose.

This disclosure describes delivery of electrical stimulation by at least one first user-selected electrode and at least one second user-selected electrode configured to deliver electrical stimulation and automatically selecting, by a programmer, at least one third electrode not selected by the user to deliver electrical stimulation to substantially balance stimulation delivered by the at least one first and at least one second electrode. For example, the at least one third electrode may substantially balance the electrical stimulation delivered by the at least one first and at least one second user-selected electrodes by balancing at least a portion of the electrical stimulation delivered by the at least one first and at least one second user-selected electrodes. In some examples, a substantially balancing current delivered by the at least one third electrode may be substantially equal to a difference in current delivered by the at least one first and at least one second user-selected electrodes as specified by a user, e.g., such that the balancing current balances substantially all of the difference in current delivered by the at least one first and at least one second user-selected electrodes. In other examples, a substantially balancing current may balance a portion of a difference between currents delivered by the at least one first and at least one second user-selected electrodes as specified by a user. The balancing current may be a sink current or a source current, as appropriate, depending on the polarity of the difference between currents generated by the at least one first and at least one second user-selected electrodes. In this case, other portions of the difference may be balanced by one or more additional third electrodes.

In some examples, it may be desirable for a balancing current delivered by the non-selected electrode to be sub-threshold current, i.e., energy (e.g., current, voltage) delivered at amplitude levels below a threshold at which stimulation can be perceived by a patient. It may be desirable to maintain a charge density of energy delivered by the non-selected electrodes at a lower level than a charge density of energy delivered at or above a threshold in which stimulation may be perceived by the patient. In some examples, balancing currents delivered by the one or more non-selected electrodes may be automatically configured to deliver energy selected to not exceed a charge density in which stimulation may be perceived by the patient. For example, the balancing currents delivered by the one or more non-selected electrodes may be automatically configured to deliver energy below one or more pre-determined thresholds. In other examples, balancing currents delivered by the one or more non-selected electrodes may be actively monitored to ensure that balancing currents do not exceed a charge density in which stimulation may be perceived by the patient.

A patient's perception threshold is a current and/or voltage amplitude at which the patient begins to experience or feel the effects caused by the electrical stimulation being delivered by one or more electrodes. Example effects caused by the electrical stimulation current include reduction of a symptom, e.g., reduction in chronic pain, and paresthesia. In some examples, the perception threshold for each patient may be established via testing, e.g., in a clinical setting. In other examples, the perception threshold may be based on a model, e.g., a basic body model, defined by a patient's age, sex, weight, and the like. The phrase "sub-threshold current" is used throughout this disclosure to describe electrical stimulation current having an amplitude below a patient's perception threshold. Utilizing non-selected lead electrodes rather than housing (i.e.) electrodes to balance stimulation current may be desirable. For example, stimulation configurations that utilize one or more housing electrodes to deliver stimulation current may cause additional heating or other undesirable effects when an IMD is exposed to external conditions, such as when a patient is in a magnetic resonance imaging (MRI) machine. In addition, stimulation configurations that utilize one or more housing electrodes to deliver stimulation current may deliver current above a patient's perception threshold, e.g., in a subcutaneous pocket in which IMD 4 is implanted.

By utilizing one or more lead electrodes to balance the stimulation current, balancing may be achieved while minimizing undesirable induced currents when a patient walks through a theft detection or airport security device. In addition, an IMD may be less likely to unnecessarily heat when influenced by external interference from a magnetic resonance imaging MRI procedure.

Figure 30:
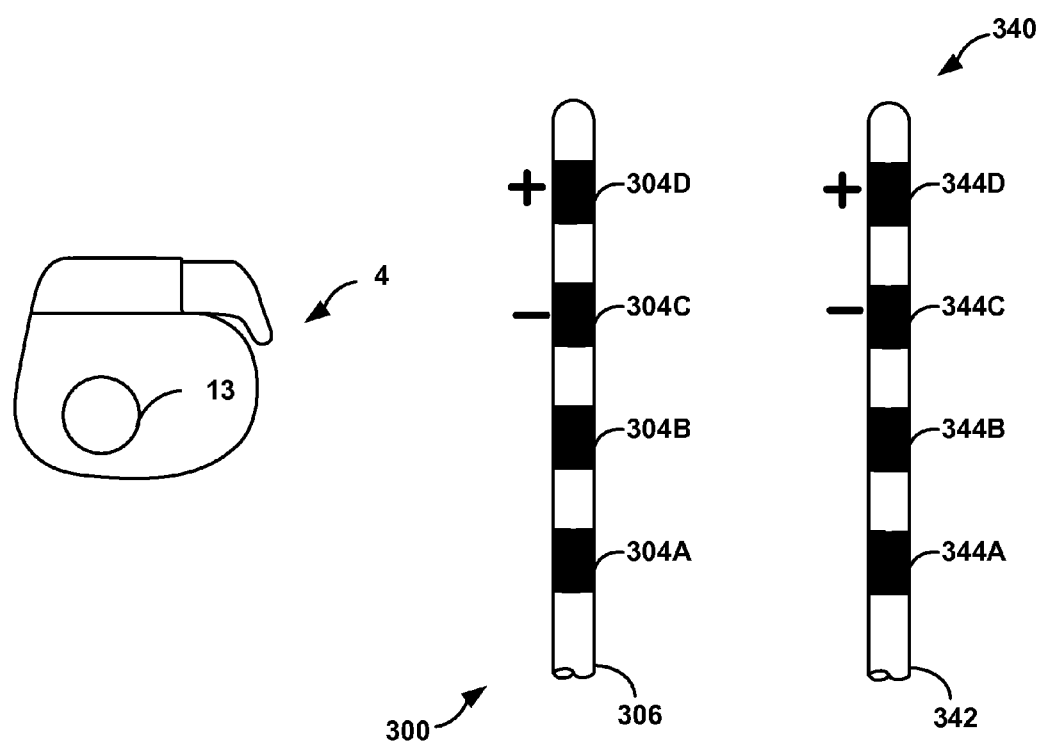
FIGS. 30-32 are conceptual diagrams illustrating example lead and electrode configurations that may be used for delivering electrical stimulation therapy using sub-threshold electrodes according to various techniques of this disclosure.
Figure 31:
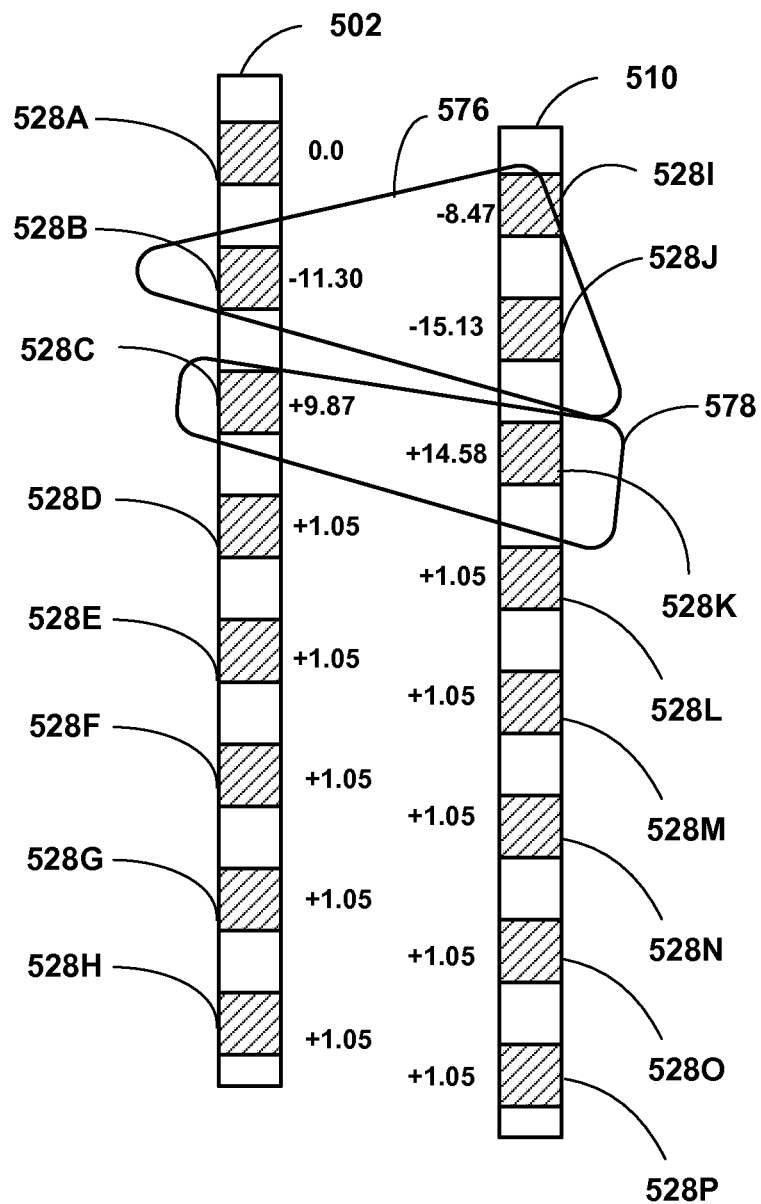
Figure 32:
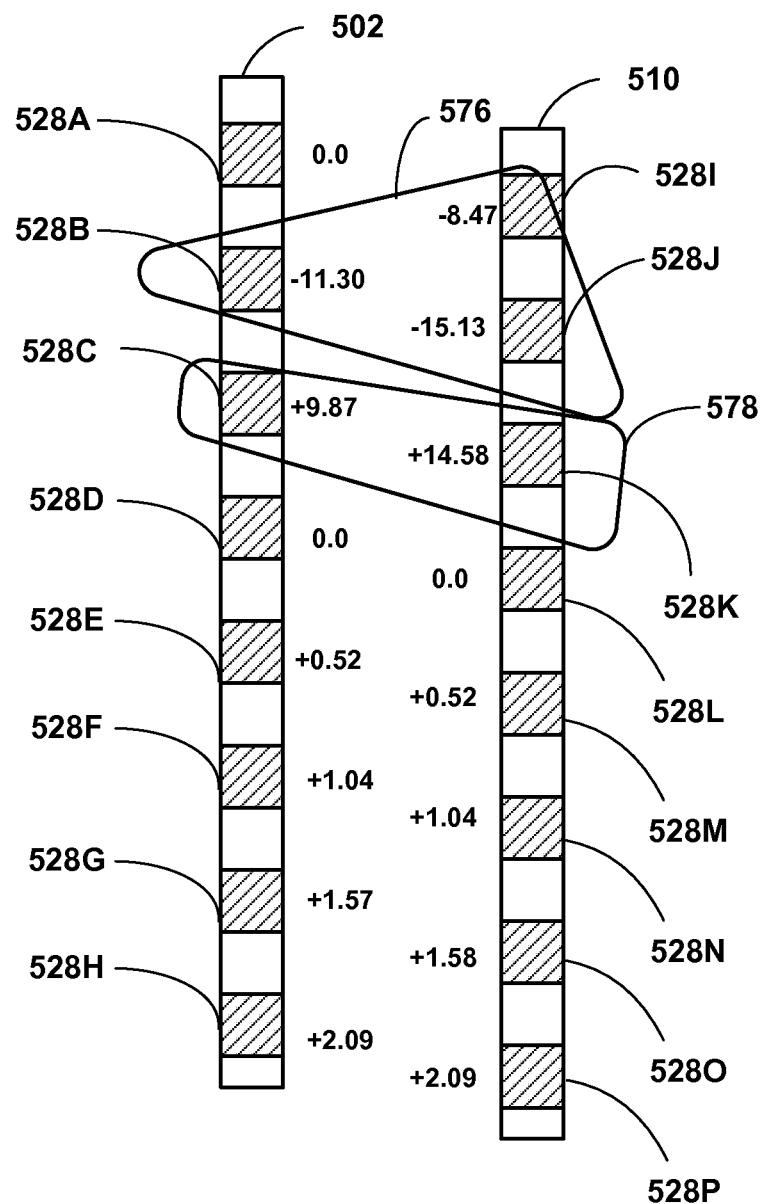

In various examples, a patient's perception threshold may be a predetermined threshold. The predetermined threshold may indicate a current level at which a patient is expected to perceive delivery of the electrical stimulation current. In one example, a predetermined threshold of one or more electrodes may be identified based on user input indicating a patient response to electrical stimulation delivered via the one or more electrodes. In some examples, the predetermined threshold may be tissue specific, e.g., a perception threshold for a particular region of patient tissue, or may be electrode or electrode combination specific, e.g., based on user perception of electrical stimulation delivered by the particular electrode or combination of electrodes. In other examples, a predetermined threshold may be a general value for which a plurality of electrodes disposed in proximity to different regions of patient tissue do not cause a perceived response in patient tissue. Again, the phrase "sub-threshold" as used in this disclosure refers to the delivery of electrical stimulation current below a patient's perception threshold FIGS. 30-32 are conceptual diagrams illustrating example lead and electrode configurations that may be used for delivering electrical stimulation therapy according to various techniques of this disclosure. FIG. 30 is similar to the configuration depicted in FIG. 15. FIG. 30 depicts two leads 300, 340, with lead 300 comprising lead body 306 having four electrodes 304 (electrodes 304A-304D) mounted at various lengths of lead body 306, and lead 340 comprising lead body 342 having four electrodes 344 (electrodes 344A-344D) mounted at various lengths of lead body 342. Unlike the configuration of FIG. 15, which uses housing electrode 13 on IMD 4 to deliver electrical stimulation to balance the stimulation currents delivered by two or more electrodes on leads 300, 340, non-selected lead electrodes of FIG. 30, e.g., lead electrodes that were not specifically targeted by a user as having a specific purpose, e.g., electrodes used for stimulation or shielding, may be automatically turned on (in some examples below a patient's perception threshold), in order to balance the stimulation and/or shielding currents delivered by electrodes selected for a specific purpose (e.g., stimulation or shielding). In other words, in the configuration depicted in FIG. 30, any lead electrode not specifically selected by a user for stimulation or shielding may be automatically configured to deliver balancing currents, rather than the using the housing electrode, e.g., housing electrode 13, to deliver balancing currents as set forth above. In other examples, as described in further detail below, the one or more non-selected electrodes may be automatically selected to deliver a balancing current to compensate for a user initiated change in a stimulation program, e.g., user selection of a different electrode combination for the delivery of shield or stimulation, or user modification of stimulation currents delivered by user selected electrodes. In still other examples, a user may be provided with an ability to switch between delivery of balancing currents via one or more non-selected lead electrodes and a housing electrode of an IMD. A user may further be provided with an ability to select relative contributions of one or more non-selected lead electrodes and a housing electrode of an IMD.

Referring to the example of FIG. 30, a first stimulation field (not shown) may be produced when electrode 304D is configured to act as an anode and source current, and electrode 304C is configured to act as a cathode and sink the current sourced by electrode 304D. A second stimulation field may be produced when electrode 344D is configured to act as an anode and source current and electrode 344C is configured to act as a cathode and sink the current sourced by electrode 344D. As described previously in this disclosure, the currents used to produce the first stimulation field and the second stimulation field (e.g., currents selected by a user) may not be equal and, as such, the system may need to deliver additional electrical stimulation current in order to balance the net charges delivered to the patient. Rather than automatically configuring housing electrode 13 to deliver the electrical stimulation current needed for balancing, one or more of lead electrodes 304A, 304B, 344A, and 344B may be used to deliver the balancing current. That is, because a user has not specifically targeted lead electrodes 304A, 304B, 344A, and 344B as having a specific purpose, e.g., stimulation or shielding, lead electrodes 304A, 304B, 344A, and 344B are available to automatically, i.e., without user intervention, be caused to deliver a third electrical stimulation current to balance the first and second currents delivered by user selected electrodes 304C, 304D, 344C and 344D. In some examples, balancing currents delivered by non-selected electrodes 304A, 304B, 344A, and 344B may be selected to have amplitudes below a patient's perception threshold, i.e., sub-threshold current, substantially simultaneously with the currents delivered to produce the first and second electrical fields in order to balance the total amount of current delivered (sourced and sunk).

By way of specific example, patient 6 may desire electrical stimulation therapy that requires a stimulation current of about 5 mA. Patient 6 may first select one or more cathodes, e.g., electrodes 304C, 344C on lead bodies 306, 342, respectively, to deliver (sink) cathodal current, e.g., 5 mA to produce a stimulation region. Patient 6 may also select one or more anodes, e.g., electrodes 304D, 344D on lead bodies 306, 342, respectively, to deliver (source) anodal current, e.g., 3 mA to produce an anodal shield. One or more non-selected electrodes on leads 300, 340 may then be automatically configured as anodes to deliver (source) current in order to balance the remaining current requirement, e.g., 2 mA. That is, one or more of non-selected electrodes 304A, 304B, 344A, and 344B may be automatically recruited as balancing electrodes to deliver (source) the remaining current required to balance the anodal and cathodal currents delivered by electrodes 304C, 304D, 344C, and 344D, e.g., 2 mA.

For example, each of non-selected electrodes 304A, 344A, and 344B may be automatically recruited by IMD 4 to deliver (source) 2 mA of current to provide the remaining 2 mA required for balancing (e.g., 0.5 mA per non-selected electrode). Or, rather than dividing the remaining current equally between non-selected electrodes 304A, 304B, 344A, and 344B, the current required to balance the system may be divided unequally. For example, it may be desirable for the electrodes that are furthest away from the electrodes producing stimulation or shields to source more sub-threshold current than electrodes that are closer to the electrodes producing stimulation or shields. In some examples, all of the sub-threshold current collectively delivered by non-selected electrodes 304A, 304B, 344A, and 344B may equal a current sufficient to balance currents of selected electrodes 304C, 304D, 344C, and 344D.

In FIG. 30, electrodes 304A and 344A are furthest away from the electrodes used to produce stimulation or shields (electrodes 304C, 304D, 344C, 344D). As such, electrodes 304A and 344A may be automatically configured to each deliver (source) 0.8 mA, while electrodes 304B and 344B are automatically configured to deliver (source) 0.2 mA. The current amplitude of 0.8 mA may be sub-threshold for the purposes of explanation. In this manner, the remaining 2 mA required to balance the currents delivered (sourced and sunk) to the patient via non-selected electrodes, with the electrodes furthest away from the electrodes used for producing stimulation fields delivering the most balancing current.

In one example, it may be desirable to utilize electrodes having greater surface areas for delivering balancing current. As mentioned above, it may be desirable to minimize the charge density beneath the non-selected electrodes. Non-selected electrodes with greater surface areas may deliver more current at the same or lower charge density than other non-selected electrodes with smaller surface areas. For example, a first non-selected electrode having twice the surface area of a second non-selected electrode may deliver electrical stimulation current having twice the current amplitude and the same current density as the second non-selected electrode. As such, the first non-selected electrode may be desirable because it can be used to deliver more current while remaining at an acceptable charge density level. In some examples, each surface area of each electrode within a lead configuration may be stored within memory 52 (or memory 55), for example. Then, based on the surface area of an electrode, processor 50 (or processor 53) may determine the amount of current that the electrode may deliver while remaining substantially sub-threshold.

It should be noted that although FIG. 30 depicts two leads, namely leads 300, 340, a single lead, or more than two leads, may be also used to perform the techniques of this disclosure. That is, a single lead, or more than two leads, may include electrodes that may be automatically configured to deliver balancing current substantially simultaneously with current delivered one or more user-selected electrodes.

Further, it should be noted that additional electrodes implanted within the body of patient 6 might also be used as non-selected electrodes to deliver balancing current. For example, additional electrodes on leads implanted within subcutaneous pockets of patient 6 may be automatically configured to deliver balancing current in the manner described in this disclosure. Patient 6 may have one or more leads having one or more electrodes implanted within one or more subcutaneous pockets in his/her back. In some examples, these leads and electrodes may be dedicated for delivery of balancing current. In other examples, these leads and electrodes may be used primarily for other electrical stimulation therapy purposes, but may be recruited by IMD 4 to deliver balancing current if the electrodes are not being fully utilized for their primary electrical stimulation purpose.

FIG. 31 is a conceptual diagram illustrating another example lead and electrode configurations that may be used for delivering electrical stimulation therapy according to various techniques of this disclosure. FIG. 31 depicts a 2×8 electrode configuration (two leads, e.g., leads 502, 510, with eight electrodes each) used to produce stimulation zone 576 and anodal shield zone 578. Stimulation zones and anodal shield zones may be referred to collectively as stimulation fields. Electrodes 528B, 528I, and 528J are used to produce stimulation zone 576 and electrodes 528C and 528K are used to produce anodal shield zone 578. Electrodes 528B, 528I, and 528J deliver (sink) 11.30 mA, 8.47 mA, and 1.513 mA, respectively. Electrodes 528C and 528K deliver (source) 9.87 mA and 14.58 mA, respectively. In other words, electrodes 528C and 528K deliver first electrical stimulation current with a first polarity, and electrodes 528B, 528I, and 528J deliver second electrical stimulation current with a second polarity opposite the first polarity. Each of the currents used to produce stimulation zone 576 and anodal shield zone 578 may be above a patient's perception threshold, i.e., not sub-threshold currents.

It is readily seen that the total current sunk (34.9 mA) by electrodes 528B, 528I, and 528J does not equal the total current sourced (24.45 mA) by electrodes 528C and 528K. In other words, the total current sunk is not balanced by the total current sourced for the electrodes selected by the user. In order to balance the currents used to produce stimulation zone 576 and anodal shield zone 578, and thus the net charge delivered by the system, one or more electrodes not selected to produce stimulation fields, e.g., stimulation zone 576 and anodal shield zone 578, may be automatically configured to deliver (source), at a sub-threshold level, the remaining (anodal) current (10.45 mA) required for balancing.

There are numerous ways to determine which non-selected electrode(s) to automatically configure to deliver a balancing current. In one example, processor 50 may simply determine candidate electrodes for the delivery of balancing current based on whether or not the electrodes were selected by the user for the delivery of current for purposes of stimulation or shielding (user-selected electrodes). In another example, processor 50 may determine candidate electrodes for the delivery of balancing current by selecting those electrodes which were not user selected, and that are also not adjacent to user-selected electrodes. In still other examples, processor 50 may determine candidate electrodes for the delivery of balancing current by selecting those electrodes which were not user selected, and that are also not adjacent to any user-selected electrodes configured to deliver current of an opposite polarity. In still another example, processor 50 may determine candidate electrodes for the delivery of balancing current by first selecting a first electrode furthest away from any selected electrode to deliver a predetermined percentage of a desired balancing current (e.g., 10%), then select the next non-selected electrode furthest away from any user-selected electrode to deliver the predetermined percentage, and so on, until the remaining amount of desired balancing current is to be delivered.

As mentioned above, it may be desirable to utilize the electrodes that are furthest away from any stimulation or anodal shield zones. Electrode 528A is an electrode adjacent to stimulation zone 576 and, as such, may be less desirable than other electrodes 528 for delivering balancing current. If electrode 528A were used to deliver balancing current, the current it delivered might undesirably affect stimulation zone 576 and thus the electrical stimulation therapy delivered to patient 6.

In the configuration depicted in FIG. 31, electrodes 528D-528H and electrodes 528L-528P have been automatically configured to deliver balancing current. Each of these electrodes have not been user selected to deliver stimulation or shield currents. Although electrodes 528D and 528K are adjacent anodal shield zone 578, these electrodes are not necessarily undesirable for the delivery of balancing current because the polarity of the sub-threshold current delivered by electrodes 528D and 528K is the same as the polarity of anodal shield zone 578. Also, with respect to stimulation zone 576, electrodes 528D and 528K are "behind" anodal shield zone 578. As such, electrodes 528D and 528K are unlikely to affect stimulation zone 576. As seen in FIG. 31, the balancing current delivered by each of electrodes 528D-528H and electrodes 528L-528P is equal (1.05 mA). These ten electrodes deliver a total of 10.50 mA of current, thereby balancing the total charge delivered by the system: 24.45 mA+10*(1.045 mA)=34.9 mA.

FIG. 32 is a conceptual diagram illustrating another example lead and electrode configuration that may be used for delivering electrical stimulation therapy according to various techniques of this disclosure. The configuration depicted in FIG. 32 is similar to the configuration depicted in FIG. 31. However, in contrast to FIG. 31, the balancing currents depicted in FIG. 32 are not distributed equally amongst the non-selected electrodes, and electrodes adjacent anodal shield zone 578 have not been recruited to deliver balancing current. As described above, it may be desirable for electrodes furthest away from stimulation zones and anodal shield zones to deliver more sub-threshold current than electrodes that are closer to these zones. For example, in FIG. 32, electrodes 528H and 528P on leads 502, 510, respectively, are the furthest away from stimulation zone 576 and anodal shield zone 578. As such, it may be desirable to deliver a higher amount of balancing current via electrodes 528H and 528P than via electrodes 528E-528G and 528M-528O. Similarly, electrodes 528G and 528O may deliver a higher amount of balancing current than that delivered by electrodes 528E-528F and 528M-528N, and so on.

In FIG. 32, depending on the proximity of the non-selected electrode to a stimulation or anodal zone, the balancing currents delivered decrease linearly along the length of leads 502, 510 from electrode 528H to electrode 528E and electrode 528P to electrode 528L (stepping at approximately 0.52 mA between electrodes on a lead). It should be noted that in other example configurations, the balancing currents delivered by the non-selected electrodes may change along a lead in a non-linear manner. For example, electrodes 528H, 528P may deliver balancing current that may be a factor of two greater than the balancing current delivered by electrodes 528G, 528O. Similarly, electrodes 528G, 528O may deliver balancing current that may be a factor of two greater than the balancing current delivered by electrodes 528F, 528N, and so on. Of course, a factor of two is used for the purposes of explanation. Other non-linear examples are within the scope of the disclosure.

Table 1 presented below depicts various example non-selected electrode current combinations that may be used to deliver current required to balance the system. Table 1 merely represents some combinations of balancing currents that may be delivered via one or more non-selected electrodes. The examples of balancing currents described in Table 1 are selected to balance a difference in anodic and cathodic currents of 10.45 mA between user-selected electrodes 528B-C, and 528I-J. Other combinations are contemplated and consistent with this disclosure. Further, the specific current levels depicted in Table 1 are with reference to FIGS. 31 and 32 and are merely provided for purposes of explanation. Various other current levels are also contemplated and consistent with this disclosure.

TABLE 1

| Electrode | Equally Distributed | Relatively Equally Distributed | Linear Away From Selected Electrodes | Non-Linear Away From Above-Selected Electrodes |
|---|---|---|---|---|
| 528A | +0.95 | Not used | Not used | +.1 |
| 528B | NA | NA | NA | NA |
| 528C | NA | NA | NA | NA |
| 528D | +0.95 | +1.04 | Not used | +.17 |
| 528E | +0.95 | +1.04 | +.52 | +.34 |
| 528F | +0.95 | +1.04 | +1.04 | +.68 |
| 528G | +0.95 | +1.05 | +1.56 | +1.36 |
| 528H | +0.95 | +1.05 | +2.08 | +2.68 |
| 528I | NA | NA | NA | NA |
| 528J | NA | NA | NA | NA |
| 528K | NA | NA | NA | NA |
| 528L | +0.95 | +1.04 | Not used | +.16 |
| 528M | +0.95 | +1.04 | +.52 | +.35 |
| 528N | +0.95 | +1.05 | +1.04 | +.67 |
| 528O | +0.95 | +1.05 | +1.56 | +1.35 |
| 528P | +0.95 | +1.05 | +2.08 | +2.67 |

Column 1 of Table 1 shows electrodes 528A-528P as depicted in FIGS. 31 and 32. As depicted in the second column from the left in Table 1 (titled "Equally Distributed"), in one example configuration, balancing currents may be delivered (sourced) equally amongst non-selected electrodes 528A, 528D-528H and 528L-528P. In contrast to the configuration depicted in FIG. 31 (which corresponds with the third column of Table 1), all electrodes, including electrode 528A that is adjacent stimulation zone 576, that are not being used to produce stimulation zone 576 and anodal shield zone 578 have been automatically configured to deliver (source) the approximately 10.45 mA of current required to balance the system.

The third column from the left in Table 1 (titled "Relatively Equally Distributed,") depicts the example configuration shown in FIG. 31. FIG. 31 was described in detail above and will not be described again. The difference between the second and third columns in Table 1 is the use of electrode 528A. Although not as desirable to use for delivering balancing current as the remaining electrodes (due to its proximity to stimulation zone 576), in some instances, electrode 528A may nonetheless be recruited to deliver balancing current.

The fourth column from the left in Table 1 (titled "Linear Away From Above-Threshold Electrodes"), depicts the example configuration shown in FIG. 32. FIG. 32 was described in detail above and will not be described again. One difference between the third and fourth columns in Table 1 is that two more electrodes in the fourth column, namely electrodes 528D and 528L (adjacent anodal shield zone 578), have not been used for delivering balancing currents. Another difference between the third and fourth columns in Table 1 is that the currents are not distributed equally between the electrodes being used to deliver balancing currents. Rather, as seen in the fourth column and as described above with respect to FIG. 32, the electrodes that are furthest away from stimulation zone 576 and anodal shield zone 578 deliver the highest amount of balancing current. The balancing current delivered decreases linearly from electrodes 528H, 528P to electrodes 528E, 528M, depending on the distance between the non-selected electrode and the user-selected electrodes used to produce stimulation zone 576 and anodal shield zone 578. In one example, the distance between the non-selected electrode and selected the electrodes used to produce stimulation zone 576 and anodal shield zone 578 may be based on a physical dimension. In another example, the distance may be based on a number of electrodes between the non-selected electrode and the selected electrodes used to produce stimulation zone 576 and anodal shield zone 578. The balancing electrode stimulation arrangement described with respect to the fourth column of Table 1 may be desirable because, by delivering the majority of balancing current via the furthest-away electrodes in relation to stimulation zone 576 and anodal shield zone 578, the sub-threshold current is less likely to interfere with or affect stimulation zone 576 and anodal shield zone 578.

The fifth column from the left (or first column from the right) in Table 1 (titled "Non-Linear Away From Above-Threshold Electrodes"), a current delivered by non-selected electrodes may increase according to a non-linear (e.g., exponential) relationship depending on the distance between the non-selected electrode and stimulation zone 576 and anodal shield zone 578. Like in the configuration depicted in column 1, the configuration in column 5 utilizes all electrodes 528 that are not used to produce stimulation zone 576 and anodal shield zone 578, including electrode 528A. As shown in the fifth column of Table 1, electrode 528A delivers a balancing current of 0.1 mA, a relatively low value in comparison with the other balancing currents due to its proximity to stimulation zone 576. Electrode 528D (the closest non-selected electrode on lead 502 to anodal shield zone 578) is also configured to deliver a relatively small amount of current (0.17 mA). Electrode 528E (the next closest non-selected electrode on lead 502 to anodal shield zone 578), is configured to deliver a current approximately twice the amount of delivered by electrode 528D (0.34 mA). Similarly, electrode 528F is configured to deliver a current approximately twice the amount delivered by electrode 528E (0.68 mA), and electrode 528G is configured to deliver approximately twice the amount of current delivered by electrode 528F (1.36 mA). Finally, electrode 528H, the furthest non-selected electrode on lead 502 from anodal shield zone 578, is configured to deliver approximately twice the amount of current delivered by non-selected electrode 528G (2.68 mA).

Similarly, electrode 528L (the closest non-selected electrode on lead 510 to anodal shield zone 578) is used to deliver a relatively small amount of current (0.16 mA). Electrode 528M (the next closest non-selected electrode on lead 502 to anodal shield zone 578) is configured to deliver a current approximately twice the amount of delivered by electrode 528L (0.35 mA). Electrode 528N is configured to deliver approximately twice the amount of current delivered by electrode 528M (0.67 mA), and electrode 528O is configured to deliver approximately twice the amount of current delivered by electrode 528N (1.35 mA). Finally, electrode 528P, the furthest non-selected electrode on lead 510 from anodal shield zone 578, is configured to deliver approximately twice the amount of current delivered by electrode 528O (2.67 mA). The balancing electrode stimulation arrangement described with respect to the fifth column of Table 1 may be desirable because, by delivering the majority of balancing current via the furthest-away electrodes in relation to stimulation zone 576 and anodal shield zone 578, the balancing current is less likely to interfere with or affect stimulation zone 576 and anodal shield zone 578.

The examples described above with respect to electrode configurations depicted in Table 1 are directed to an IMD that includes a plurality of substantially similar electrodes carried by one or more leads of the IMD. In other examples not depicted in Table 1, the IMD may include electrodes that are not substantially similar. For example, a first electrode may have a first surface area, while a second electrode may have a different surface area than the first surface area. The surface area of the electrode may be used by processor 50, for example, to determine amplitudes of balancing current that may be delivered by the one or more non-selected electrodes. For example, a larger electrode that presents a larger surface area may deliver more current but at the same current density than another electrode having a smaller surface area. Thus, the size, shape and, in particular, the surface area, of one or more non-selected electrodes may be taken into account by processor 50 in determining relative balancing current contributions of one or more non-selected electrodes.

It should also be noted that the balancing current electrode techniques of this disclosure are not limited to non-selected electrodes being automatically, i.e., without user intervention, configured as anodes to deliver (source) current required to balance the system. Rather, one or more non-selected electrode(s) may also be automatically, i.e., without user intervention, configured as one or more cathodes to deliver (sink) current required to balance the system. As described herein, the one or more non-selected electrodes may be automatically configured as one or more anodes or cathodes to deliver balancing current by one or more processors. The one or more processors may be a processor of the IMD, of another IMD, or of an external programmer or larger IMD system.

Figure 33:
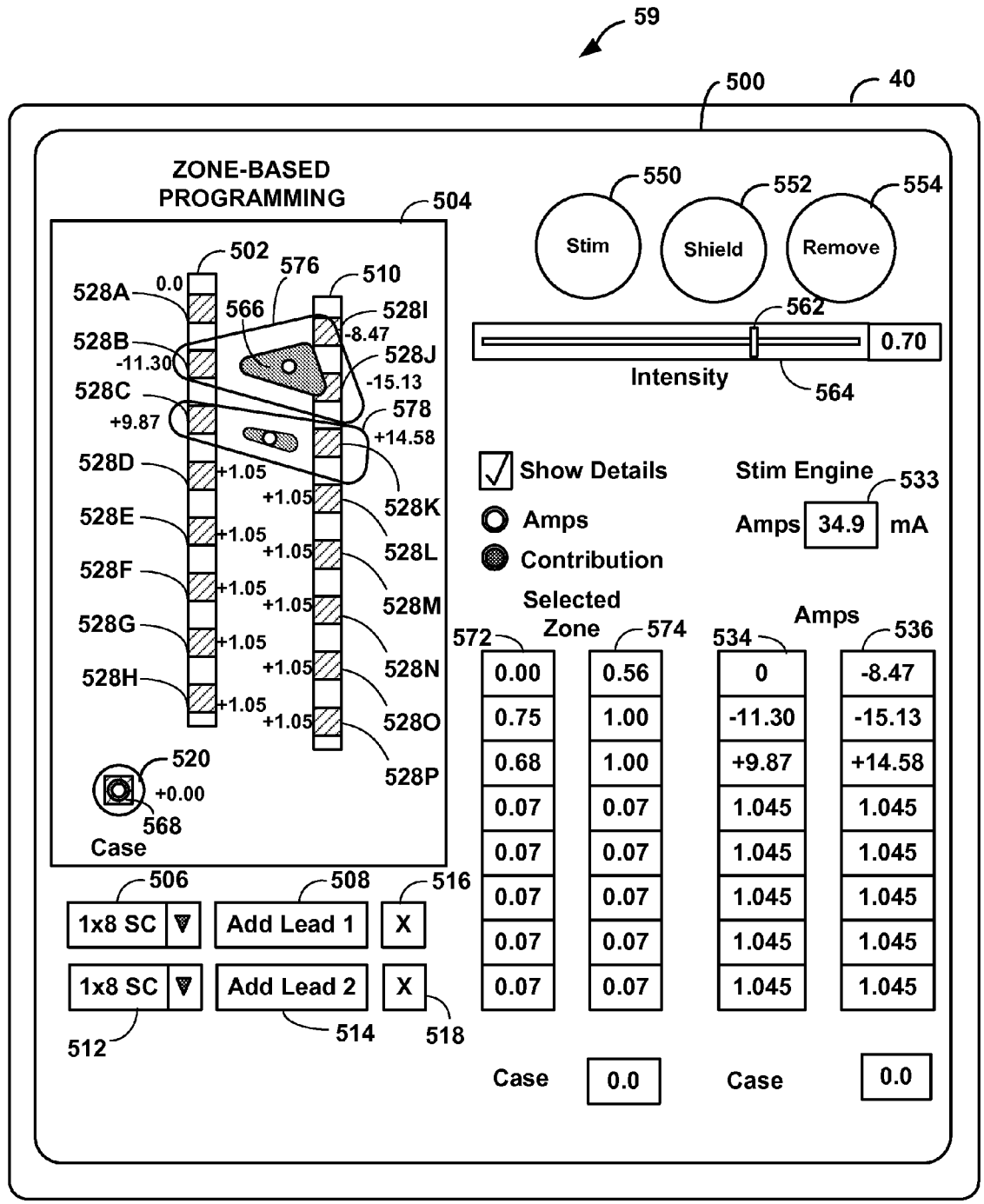
FIGS. 33-36 are schematic diagrams illustrating example user interfaces presented by the programmer of FIG. 4.

FIG. 33 depicts a user interface illustrating an arrangement that makes use of non-selected electrodes to automatically balance the current delivered by the system, in accordance with the techniques described above, created using zone-based programming. User interface 59 of FIG. 33 depicts the electrode configuration shown and described above with respect to FIG. 31. FIG. 33 is similar to the user interface shown in FIG. 25 and, as such, user interface 59 will not be described in detail again. Window 504 of FIG. 33 depicts stimulation zone 576 and anodal shield zone 578. Stimulation zone 576 is produced by electrodes 528B, 528I, and 528J delivering (sinking) currents of 8.47 mA, 11.30 mA, and 15.13 mA, respectively. Anodal shield zone 578 is produced by electrodes 528C and 528K delivering (sourcing) currents of 9.87 mA and 14.58 mA, respectively. As seen in FIG. 33, case electrode 520 is not delivering any current (0.00 mA).

The total current sunk (34.9 mA) by electrodes 528B, 528I, and 528J does not equal the total current sourced (24.45 mA) by electrodes 528C and 528K. In other words, the total current delivered by the system is not balanced. In order to balance the currents used to produce stimulation zone 576 and anodal shield zone 578, and thus the net charge delivered by the system, one or more electrodes not used to produce stimulation zone 576 and anodal shield zone 578 may be automatically configured to deliver (source) the remaining (anodal) current (10.45 mA in the example of 33) required for balancing.

In accordance with the techniques of this disclosure, processor 53 of programmer 40, for example, automatically configures non user-selected electrodes 528D-528H and electrodes 528L-528P to deliver balancing current. In some examples, the balancing current may be sub-threshold current delivered below a patient's perception threshold. Each of the non-selected electrodes may outside any keep out areas, e.g., an ellipse or other geometric shape "drawn" by processor 53 around electrodes used to produce stimulation or anodal shield zones. Each of the non-selected electrodes may instead be electrodes not directly selected by the user to deliver energy for shielding or stimulation. Although electrodes 528D and 528K are adjacent anodal shield zone 578, these electrodes are not necessarily undesirable for delivery of balancing currents because the polarity of the sub-threshold current delivered by electrodes 528D and 528K (positive) is the same as the polarity of anodal shield zone 578 (positive). Also, with respect to stimulation zone 576, electrodes 528D and 528K are "behind" anodal shield zone 578. As such, electrodes 528D and 528K are unlikely to affect stimulation zone 576. Electrode 528A is an electrode adjacent to stimulation zone 576 and as such, may be less desirable than other electrodes 528 for delivering balancing current. If electrode 528A were used to deliver balancing current, it may affect stimulation zone 576 and thus the electrical stimulation therapy delivered to patient 6. Thus, in the configuration shown in FIG. 33, programmer 40 has determined that electrode 528A should not be used to deliver balancing current.

As seen in FIG. 33, the balancing current delivered by each of electrodes 528D-528H and electrodes 528L-528P is equal (1.045 mA). These ten electrodes deliver a total of 10.45 mA of current, thereby balancing the net charge delivered by the system (24.45 mA+10.45 mA=34.9 mA sourced current). In this manner, non-selected electrodes on leads 502, 510 that are not used to produce either stimulation or anodal shield zones may be used to automatically balance the net current delivered by the system.

Arrays 572 and 574 depict the contributions of each of the zones on each of the two leads 502, 510. In order to determine the contributions of the non-selected electrodes 528D-528H and non-selected electrodes 528L-528P, the current delivered by the selected electrodes is compared to the contributions by other anodes. As seen in FIG. 33, the ten non-selected electrodes deliver 10.45 mA/14.58 mA, or 0.716. Thus, each of the ten non-selected electrodes has a contribution of approximately 0.07, as seen in arrays 572, 574.

Figure 34:
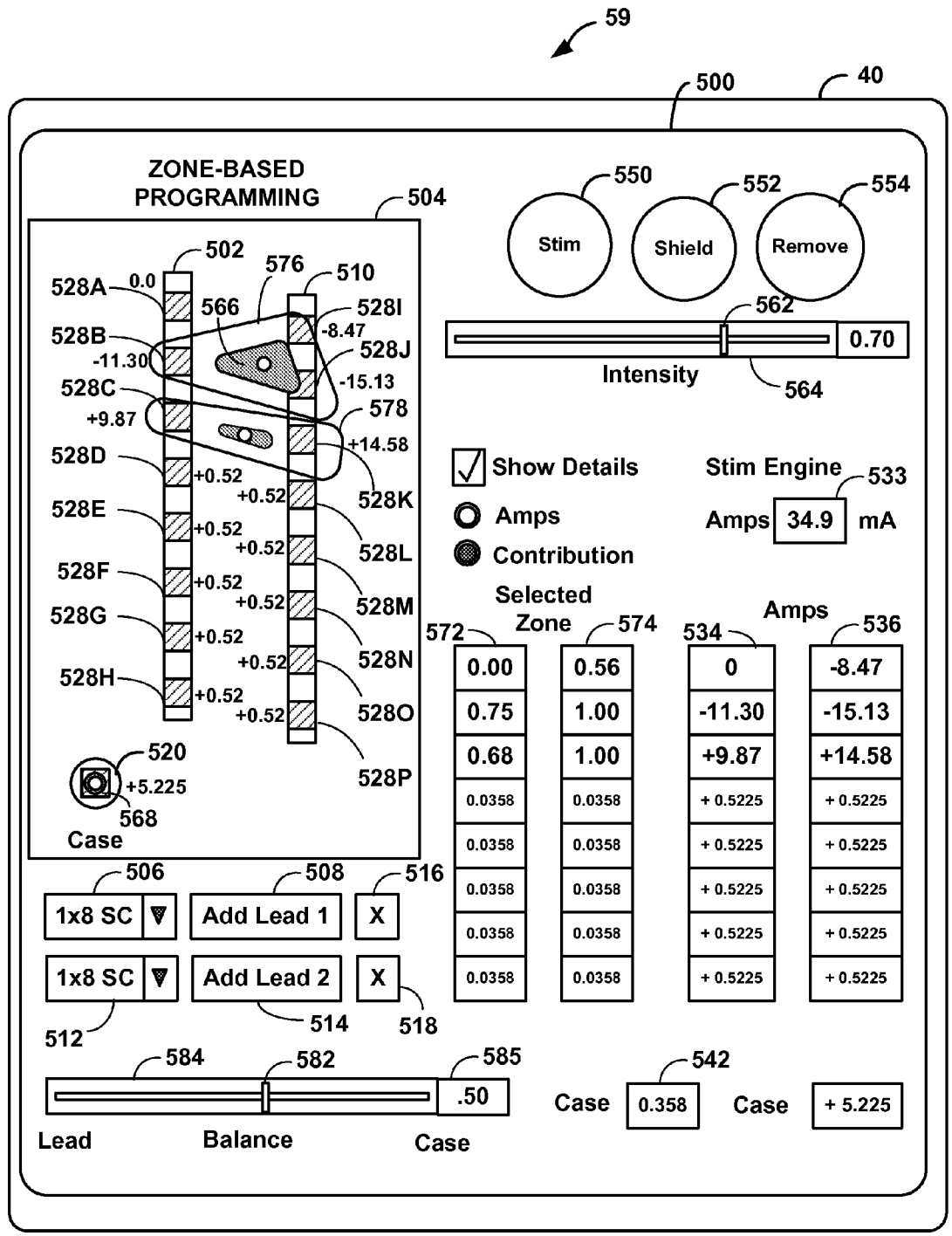

FIG. 34 depicts another user interface illustrating an arrangement that makes use of non-selected electrodes to automatically balance the current delivered by the system, in accordance with the techniques described above, created using zone-based programming. In particular, FIG. 34 depicts an arrangement in which both case electrode 520 and one or more non-selected electrodes on leads 502, 510 are automatically configured to balance the net current delivered by the system. In order to select a balance between case electrode 520 and one or more non-selected electrodes on leads 502, 510, a user may use a stylus or other pointing media to move indicator 582 along horizontal scroll bar 582. For example, in FIG. 34, the balance is set at 0.50, as shown at 585. In other words, the percentage of current to be automatically delivered by case electrode 520 is equal to the percentage of current to be automatically delivered by one or more non-selected lead electrodes.

Stimulation zone 576 and anodal shield zone 578 are identical to those described in FIG. 33 and, as such, will not be described again. The total current sunk (34.9 mA) by electrodes 528B, 528I, and 528J does not equal the total current sourced (24.45 mA) by electrodes 528C and 528K. In order to balance the currents used to produce stimulation zone 576 and anodal shield zone 578, and thus the net charge delivered by the system, case electrode 520 and one or more electrodes not used to produce stimulation zone 576 and anodal shield zone 578 may be automatically configured to deliver (source), at a sub-threshold level, the remaining (anodal) current of 10.45 mA required for balancing.

Based on the balance setting of 0.50 determined via horizontal scroll bar 584, processor 53, for example, divides the required balancing current of 10.45 mA approximately equally between case electrode 520 and one or more non-selected electrodes 528 on leads 502, 510. In other words, processor 53 automatically configures case electrode 520 to deliver (source) approximately 5.225 mA and one or more non-selected electrodes to deliver (source) the remaining 5.225 mA of current. As seen in FIG. 34, each of non-selected lead electrodes 528D-528H and 528L-528P deliver approximately 0.5225 mA of current. These ten electrodes deliver a total of 5.225 mA of current, thereby balancing the net charge delivered by the system along with case electrode 520, which also delivers 5.225 mA of balancing current. In this manner, non-selected electrodes on leads 502, 510 that are not used to produce either stimulation or anodal shield zones may be used in conjunction with case electrode 520 to automatically balance the net current delivered by the system.

To determine the contribution of case electrode 520, the current sourced by case electrode 520 is compared to the contributions by other anodes. Thus, case electrode 520 has a contribution of 5.225 mA/14.58 mA, or about 0.358, as shown at 542. Arrays 572 and 574 depict the contributions of each of the zones on each of the two leads 502, 510. In order to determine the contributions of the non-selected lead electrodes 528D-528H and 528L-528P, the current delivered by the non-selected electrodes is compared to the contributions by other anodes. As seen in FIG. 34, the ten non-selected electrodes deliver 5.225 mA/14.58 mA, or 0.358. Thus, each of the ten non-selected electrodes has a contribution of 0.0358 in arrays 572, 574.

It should be noted that in the example shown in FIG. 34, it may be desirable for only electrodes 528G, 528H, 528O, and 528P to deliver the remaining 5.225 mA of current. These four electrodes are the furthest away from stimulation zone 576 and anodal shield zone 578 and, as such, would have the least effect on zones 576, 578. Or, it may be desirable to configure the non-selected electrodes along leads 502, 510 to deliver the balancing currents in a non-linear manner, as described above. The configuration shown in FIG. 34 is only one of many possible configurations that may be used to automatically balance the net current delivered by the system.

Figure 35:
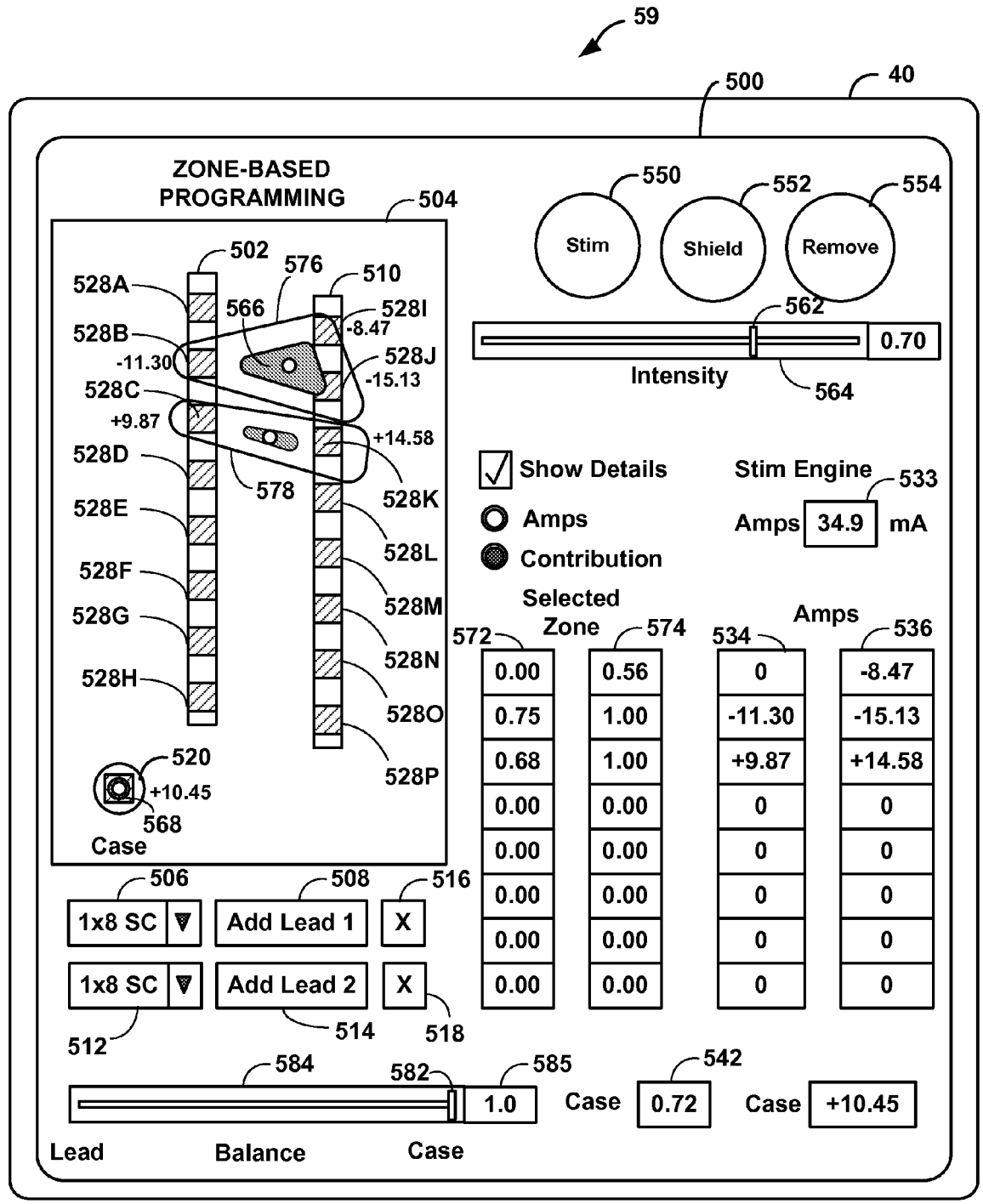

FIG. 35 depicts another user interface presented by the programmer of FIG. 4 that may be used to automatically balance the current delivered by the system, created using zone-based programming. In particular FIG. 35 depicts the configuration shown in FIG. 34, but with the balance between non-selected electrodes and the case electrode at 1.0, as shown at 585. In other words, all current required to balance the currents delivered by the system will be delivered by case electrode 520, and non-selected electrodes on leads 502, 510 will not be used. The user interface of FIG. 35 is similar to the configuration shown and described above with respect to FIG. 25 and, as such, will not be described again. It should be noted that if indicator 582 was moved completely to the left on horizontal scroll bar 584, the system would be configured to deliver all balancing currents via one or more non-selected electrodes, as shown in FIG. 33.

As mentioned above, utilizing lead electrodes rather than housing electrodes to balance stimulation current may be desirable to reduce or eliminate additional heating in the case electrode during an MRI procedure, as well as to reduce or eliminate EMI issues when utilizing the case electrode to deliver some or all of the balancing current. The configurations depicted in FIGS. 34 and 35 allow a user to easily transition between case electrode based delivery of balancing current and non-selected lead electrode based delivery of balancing current, as well as hybrids utilizing both aspects. For example, a patient who is about to be imaged in an MRI modality may transition to the non-selected electrode based configuration shown in FIG. 33. Or, if a patient is experiencing undesirable stimulation via the case electrode, e.g., in a subcutaneous pocket, when the case electrode is delivering all of the balancing current, then the patient may adjust the balance (using horizontal scroll bar 584) to deliver some or all balancing current via non-selected electrodes on leads 502, 510.

Figure 36:
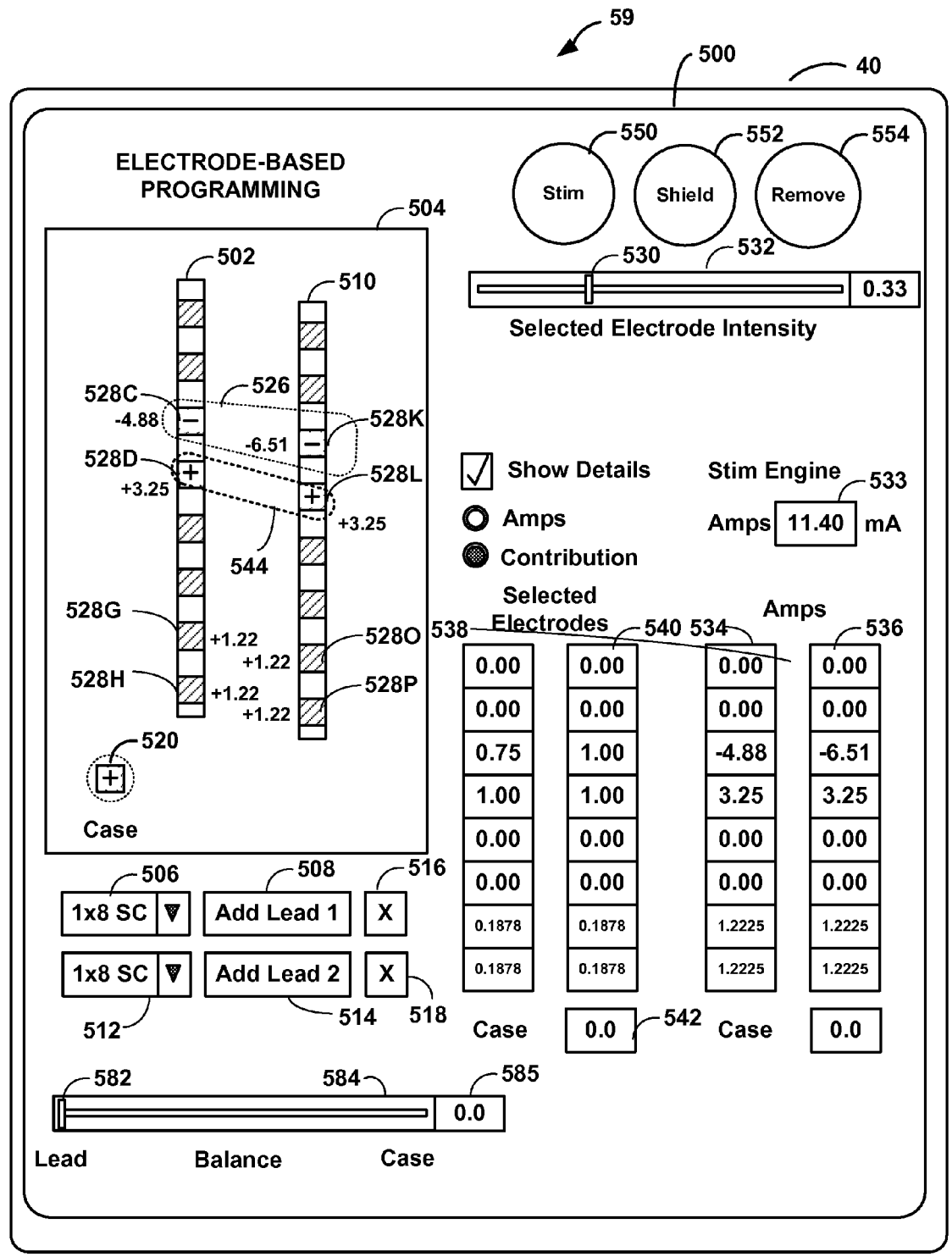

FIG. 36 depicts another user interface illustrating an arrangement that makes use of non-selected electrodes to automatically (e.g., without user intervention, such as by one or more processors) balance the current delivered by the system, in accordance with the techniques described above, created using electrode-based programming. Rather than utilizing zone-based programming for automatically configuring non-selected electrodes, as in the configurations shown in FIGS. 33-35, electrode-based programming may be utilized. Electrode-based programming was described in detail above with respect to FIGS. 18-21 and, as such, will not be described in detail again.

FIG. 36 is similar to FIG. 20, with the notable exception that one or more non-selected electrodes, rather than the case electrode, are configured to automatically deliver balancing current. After a user has selected the particular electrodes 528 to create stimulation zone 526 and anodal shield zone 544 and selected the desired intensity, processor 53 of programmer 40 generates fields 526, 546 and depicts the currents associated with the selected electrodes that are needed to generate fields 526, 546. As shown in FIG. 36, electrodes 528D and 528L, configured as anodes, each source 3.25 mA and 3.25 mA (a total of 6.5 mA). Electrodes 528C and 528K, configured as cathodes, sink 4.88 mA and 6.51 mA (a total of 11.39 mA), respectively. The remaining current needed to balance the system, 4.89 mA, is entirely sourced by one or more non-selected electrodes 528 on leads 502, 510, as selected by the user by sliding indicator 582 to the left along horizontal scroll bar 584. Although there are numerous methods to distribute the current between electrodes on leads 502, 510 that are not being used to produce stimulation zone 526 and anodal shield zone 544, window 504 depicts the currents being equally distributed between the four electrodes furthest away from zones 526, 544. In particular, electrodes 528G, 528H, 528O, and 528P each deliver 1.2225 mA of current, or a total of 4.89 mA. In this manner, electrode-based programming may be used to automatically balance the currents delivered by the system.

Arrays 538, 540 depict the contributions of each of the electrodes on each of the two leads 502, 510. In order to determine the contributions of the non-selected lead electrodes 528G, 528H, 528O, and 528P, the current delivered by the non-selected lead electrodes is compared to the contributions by other anodes. As seen in FIG. 36, the four non-selected electrodes deliver 4.89 mA/6.50 mA, or 0.752. Thus, each of the four non-selected electrodes has a contribution of 0.1878 as shown in arrays 538, 540.

Although user interface 59 of FIG. 36 depicts non-selected electrodes delivering all of the balancing current, as determined by the position of indicator 582, it should be noted that the balancing current may be divided between case electrode 520 and one or more non-selected electrodes on leads 502, 510 in a manner similar to that described above with respect to FIGS. 34 and 35.

Figure 37:
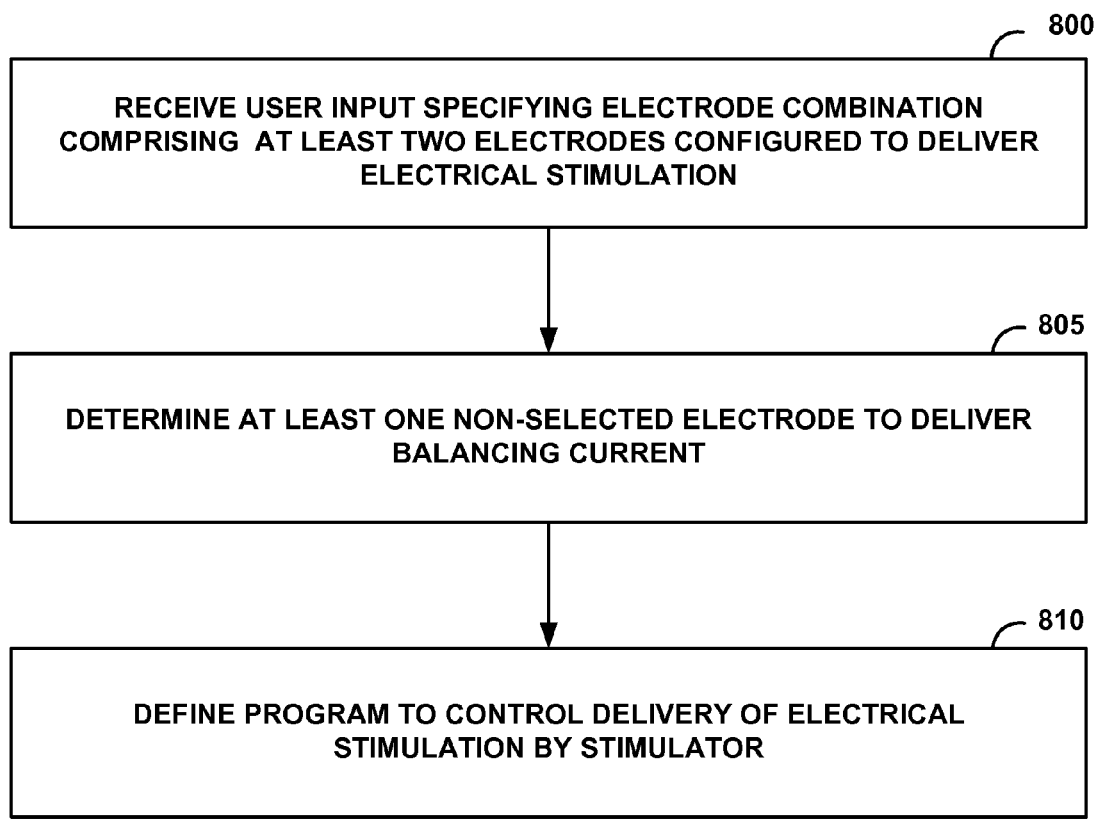
FIG. 37 is a flow diagram illustrating example operation of a programmer for generating a program to control delivery of electrical stimulation.

FIG. 37 is a flow diagram illustrating example operation of a programmer for generating a program to control delivery of electrical stimulation. In FIG. 37, a programmer, e.g., external programmer 40, receives, via user interface 59, user input specifying an electrode combination for delivery of electrical stimulation from an electrical stimulator to a patient (800). The electrode combination may comprise two or more electrodes selected by a user to deliver electrical stimulation for a particular purpose, i.e., two or more electrodes configured to produce one or more stimulation zones and/or anodal shield zones. The two or more electrodes may be selected from a plurality of electrodes carried by at least one lead of the IMD (e.g., leads 502, 510). Programmer 40 determines at least one non-selected electrode to deliver electrical stimulation to automatically balance the net current delivered by the system (805). In one example, programmer 40 automatically determines the non-selected electrode(s) based on the two or more electrodes configured to produce one or more stimulation zones and/or anodal shield zones. For example, programmer 40 may determine one or more keep out areas and select non-selected electrodes based on their proximity to the keep out areas. In some examples, the amount of current delivered via each non-selected electrode may increase linearly along the length of a lead such that electrodes furthest away from stimulation zones and/or anodal shield zones deliver the most balancing current of the non-selected electrodes. In other examples, the current delivered via each non-selected electrode may increase in a non-linear manner. Programmer 40 may then define an electrical stimulation program to deliver electrical stimulation by the stimulator based at least in part on the user input specifying the selected electrode combination (810).

The non-selected electrodes may be carried by the same lead(s) used to produce cathodic stimulation zones and/or anodal shield zones, or by different leads located in other regions of a patient's body, e.g., a subcutaneous pocket in the patient's back. In some examples, the stimulation zones may deliver (sink) more current than the anodal shield zones deliver (source). As such, non-selected electrodes may be configured as cathodes to deliver (sink) additional current required to balance the net current delivered by the system. In another example, the stimulation zones may deliver (sink) less current than the anodal shield zones deliver (source). As such, the non-selected electrodes may be configured as anodes to deliver (source) additional current required to balance the net current delivered by the system.

In some examples, specifying an electrode combination comprises using a pointing media, e.g., a stylus, to select electrodes of the electrode combination. In other examples, specifying an electrode combination comprises dragging a stimulation field, e.g., stimulation zone or anodal shield zone, relative to the one or more leads. The user may additionally add and drag another stimulation field relative to the at least one lead.

Figure 38:
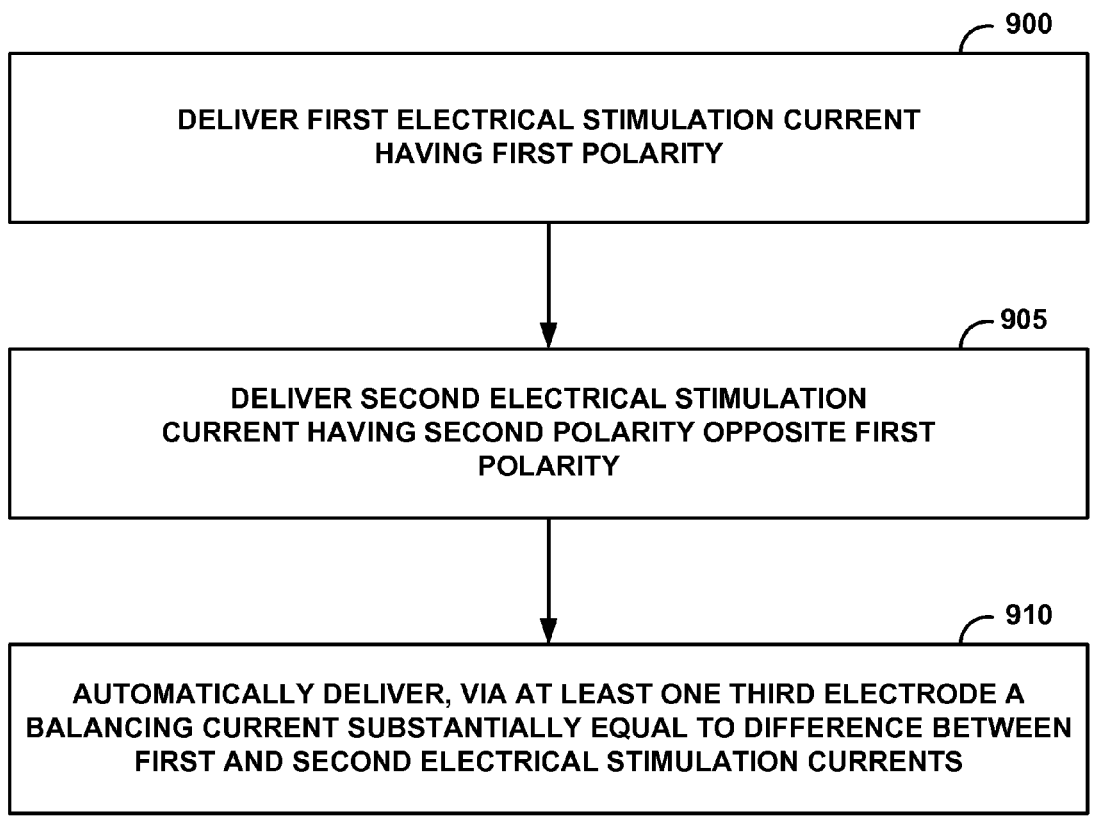
FIG. 38 is a flow diagram illustrating an example method of delivering electrical stimulation using the techniques of this disclosure.

FIG. 38 is a flow diagram illustrating an example method of delivering electrical stimulation using the techniques of this disclosure. In the method shown in FIG. 38, IMD 4, and in particular, stimulation generator 60, delivers first electrical stimulation current with a first polarity (e.g., negative) via a first electrode of IMD 4, e.g., electrode 304C of FIG. 30, (900). The electrical stimulation current delivered by the first electrode may have an amplitude above a patient's perception threshold. Stimulation generator 60 delivers second electrical stimulation current with a second polarity opposite the first polarity (e.g., positive) via a second electrode, e.g., electrode 304D of FIG. 30, (905). The electrical stimulation current delivered by the second electrode may have an amplitude above the patient's perception threshold. The electrical stimulation current delivered by the first and second electrodes is used to produce cathodic stimulation zones and/or anodal shield zones. Without user intervention, stimulation generator 60 delivers third electrical stimulation via at least one third electrode of IMD 4, e.g., electrode 304A, that is not configured to produce a stimulation field, i.e., an electrode that is not user selected to produce a stimulations zone and/or an anodal shield zone (910). Stimulation generator 60 delivers the third electrical stimulation current substantially simultaneously with the electrical stimulation current delivered via the first electrode and the second electrode. In some examples, the third electrical stimulation current has an amplitude below a perception threshold. In other words, the third electrode may be configured to deliver sub-threshold current. In this manner, stimulation generator 60 automatically configures the third electrode to deliver a difference in current between the first electrical stimulation current and the second electrical stimulation current, thereby automatically balancing the net charge delivered by the system.

In some examples, stimulation generator 60A may couple the first electrode, e.g., electrode 304C, to a first regulated current path to deliver a first amount of the electrical stimulation current. Stimulation generator 60A may also couple the second electrode, e.g., electrode 304D, via switch array 66, to a second regulated current path to deliver a second amount of the electrical stimulation current. Stimulation generator 60A may couple the third electrode, e.g., electrode 304A, to a regulated current path to receive a third amount of the electrical stimulation current. The third amount of electrical stimulation current may be approximately equal to a sum of the first and second amounts of the electrical stimulation current. In one example, the first amount of the electrical stimulation current is a first regulated source current, the second amount of the electrical stimulation current is a second regulated source current, and the third amount of the electrical stimulation current is a regulated sink current that is approximately equal to a sum of the first and second regulated source currents.

Numerous other configurations are considered to be within the scope of this disclosure. Such configurations may include, but are not limited to the following examples. One example configuration delivers (sources) regulated current via the third electrode, delivers (sources) regulated current via the first electrode, and delivers (sinks) regulated current via the second electrode.

Another example configuration delivers (sources) regulated current via the third electrode, delivers (sources) regulated current via the first electrode, and delivers (sinks), via the second electrode, unregulated current to a reference voltage. That is, the second electrode is electrically coupled to a reference voltage to deliver (sink) unregulated current.

Another example configuration delivers (sources) regulated current via the third electrode, delivers (sources) regulated current via the first electrode, and delivers, via the second electrode, unregulated current (sources) from a reference voltage. That is, the second electrode is electrically coupled to a reference voltage to deliver (source) unregulated current.

Another example configuration delivers (sinks), via the third electrode, unregulated current, to a reference voltage (i.e., the third electrode is electrically coupled to a reference voltage to deliver (sink) unregulated current), delivers regulated current (sources) via the first electrode on a lead, and delivers (sources) regulated current via the second electrode.

Another example configuration delivers (sources), via the first electrode, unregulated current, from a reference voltage (i.e., the first electrode is electrically coupled to a reference voltage to deliver (sources) unregulated current), delivers regulated current (sources) via the first electrode, and delivers (sinks) regulated current via the second electrode.

Another example configuration delivers (sinks), via the third electrode, unregulated current, to a reference voltage (i.e., the third electrode is electrically coupled to a reference voltage to deliver (sink) unregulated current), delivers (sources), from a regulated voltage source, unregulated current via the first electrode, and delivers (sinks), to a regulated voltage source, unregulated current via the second electrode.

Another example configuration delivers (sources), via the third electrode, unregulated current, from a reference voltage (i.e., the third electrode is electrically coupled to a reference voltage to deliver (sources) unregulated current), delivers (sources), from a regulated voltage source, unregulated current via the first electrode on a lead, and delivers (sinks), to a regulated voltage source, unregulated current via the second electrode.

Figure 39:
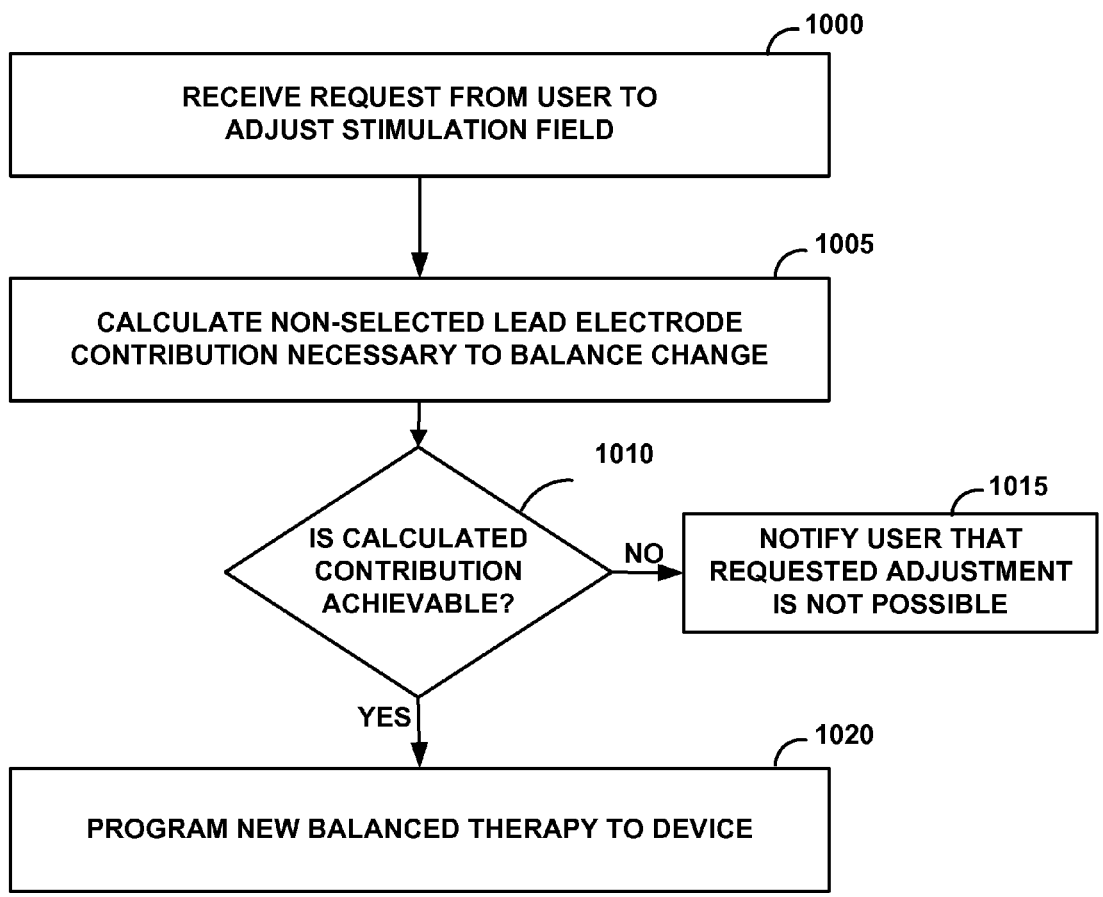
FIG. 39 is a flow diagram illustrating another example operation of the programmer for generating a program to control delivery of electrical stimulation.

FIG. 39 is a flow diagram illustrating another example operation of the programmer for generating a program to control delivery of electrical stimulation. FIG. 39 depicts an example in which stimulation is automatically balanced after a user adjusts one or more aspects of stimulation, e.g., a change in one or more electrode contributions, a change in the intensity of one or more aspects of a field, or other changes that would result in unbalanced stimulation. A user initiated change in one or more electrode contributions may include the selection of an electrode previously not selected as a selected electrode. A programmer, e.g., external programmer 40, may receive a request from a user via user interface 59 to adjust a stimulation field, e.g., stimulation zone and/or anodal shield zone (1000). In response, the programmer, and in particular processor 53, calculates a non-selected lead electrode contribution (and, in some examples, also a case electrode contribution) necessary to balance the change caused by the requested adjustment (1005).

Processor 53 may, for example, compare the calculated non-selected electrode contribution with one or more predetermined threshold values in order to determine if the non-selected lead electrode contribution calculated is achievable (1010). If the non-selected electrode contribution is not achievable, e.g., the calculated non-selected electrode contribution exceeds the threshold value ("NO" at block 1010), then the user is notified, e.g., via user interface 59, that the requested adjustment is not possible (1015). If the calculated non-selected electrode contribution is achievable, e.g., the calculated non-selected electrode contribution does not exceed the threshold value ("YES" at block 1010), then the programmer programs the new balanced therapy to the device (1020). The adjustment requested by the user may result, for example, in one or more non-selected lead electrodes (and, in some examples, the case electrode) sourcing more or less current, changing from an anode (source) to a cathode (sink), or turning off, e.g., if the current sourced or sunk by the one or more non-selected electrodes after the user adjustment is approximately zero or otherwise insignificant. In some examples in which a user initiated change to one or more electrode contributions may include the selection of an electrode previously not selected as a selected electrode, the programmer may select other non-selected electrodes to balance a current delivered by user selected electrodes.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Various examples of the disclosure have been described. These and other examples are within the scope of the following claims.

The invention claimed is:

1. A method comprising:
receiving, via a user interface of a programmer device for an implantable electrical stimulator, user input specifying at least one first user-selected electrode to deliver electrical stimulation of a first polarity and at least one second user-selected electrode to deliver electrical stimulation of a second polarity different than the first polarity for delivery of electrical stimulation from an implantable electrical stimulator to a patient;
receiving, via the user interface, user input specifying amounts of electrical stimulation current to be supplied via the at least one first user-selected electrode and the at least one second user-selected electrode;
automatically selecting, by one or more processors, at least one third electrode not specified as a user-selected electrode to deliver electrical stimulation to substantially balance the electrical stimulation current to be delivered via the at least one first user selected electrode and the at least one second user-selected electrode; and
defining a program to control delivery of the electrical stimulation by the stimulator based on the user input.

2. The method of claim 1, wherein automatically selecting the at least one third electrode includes automatically determining an amount of electrical stimulation to be delivered via the at least one third electrode.

3. The method of claim 2, wherein automatically determining an amount of electrical stimulation to be delivered via the at least one third electrode includes automatically determining the amount based on a difference between an amount of electrical stimulation delivered via the at least one first user selected electrode and the at least one second user-selected electrode.

4. The method of claim 3, wherein automatically determining an amount of electrical stimulation to be delivered via the at least one third electrode includes automatically determining the amount equal to the difference between the amount of electrical stimulation delivered via the at least one first user selected electrode and the at least one second user-selected electrode.

5. The method of claim 3, wherein automatically determining an amount of electrical stimulation to be delivered via the at least one third electrode includes automatically determining the amount equal to a portion of the difference between the amount of electrical stimulation delivered via the at least one first user selected electrode and the at least one second user-selected electrode.

6. The method of claim 2, wherein automatically determining an amount of electrical stimulation to be delivered via the at least one third electrode includes automatically determining a sub-threshold current to be delivered via the at least one third electrode, and wherein the sub-threshold current comprises a current amplitude below a perception threshold of the patient.

7. The method of claim 1, wherein receiving, via the user interface of an electrical stimulator programmer device, user input specifying the at least one first user selected electrode and the at least one second user-selected electrode comprises:
receiving user input via a pointing media to select the at least one first user selected electrode and the at least one second user-selected electrode.

8. The method of claim 1, wherein receiving, via the user interface of an electrical stimulator programmer device, user input specifying the at least one first user selected electrode and the at least one second user-selected electrode comprises:
receiving user input that drags a stimulation field relative to at least one lead.

9. The method of claim 1, wherein automatically selecting the at least one third electrode includes automatically selecting at least one housing electrode.

10. The method of claim 1, wherein automatically selecting the at least one third electrode includes automatically selecting at least one lead electrode.

11. The method of claim 1, wherein automatically selecting the at least one third electrode comprises automatically selecting at least one lead electrode and at least one housing electrode.

12. The method of claim 11, further comprising:
receiving, from a user, input specifying relative contributions of the at least one lead electrode and the at least one housing electrode to deliver electrical stimulation below the perception threshold of the patient.

13. The method of claim 12, wherein receiving, from a user, input specifying relative contributions includes receiving user input adjusting a slideable medium within a range.

14. The method of claim 1, wherein automatically selecting at least one third electrode not specified as a user-selected electrode to deliver electrical stimulation to substantially balance the electrical stimulation current to be delivered via the at least one first user selected electrode and the at least one second user-selected electrode includes automatically selecting a plurality of third electrodes.

15. The method of claim 14, wherein automatically selecting a plurality of third electrodes includes automatically determining an amount of electrical stimulation to be delivered via each of the plurality of third electrodes.

16. The method of claim 14, further comprising automatically determining amounts of electrical stimulation to be delivered via each of the plurality of third electrodes, the amounts of electrical stimulation being sub-threshold amounts of current to be delivered via each of the plurality of third electrodes, wherein the sub-threshold amounts of current comprise sub-threshold current amplitudes below a perception threshold of the patient.

17. The method of claim 14, further comprising automatically determining a respective amount of electrical stimulation to be delivered via each of the plurality of third electrodes, the respective amount of electrical stimulation being a respective sub-threshold amount of current to be delivered via each of the plurality of third electrodes, wherein the respective sub-threshold amounts of current comprise current amplitudes below a perception threshold of the patient, and wherein at least some of the respective sub-threshold amounts of current for the plurality of third electrodes not equal.

18. The method of claim 14, wherein the plurality of third electrodes comprises all electrodes not specified as a user-selected electrode.

19. The method of claim 1, wherein the program is a first program, and wherein a first sum of the amounts of electrical stimulation current to be supplied via the at least one first user-selected electrode and the at least one second user-selected electrode and the at least one third electrode substantially equals zero, the method further comprising:

receiving, via the user interface, user input specifying an adjustment to at least one of the at least one first user-selected electrode and the at least one second user-selected electrode;

automatically determining, for the at least one third electrode, an amount of electrical stimulation current such that a second sum of the electrical stimulation currents to be supplied by each of the first, second, and third electrodes equals zero; and defining a second program to control delivery of the electrical stimulation by the stimulator based on the automatically determined amounts of electrical stimulation currents.

20. The method of claim 1, wherein the at least one third electrode is separated from the at least first user selected electrode and the at least one second user-selected electrode by one or more electrodes not specified to deliver electrode stimulation.

21. The method of claim 1, wherein the at least one third electrode comprises one or more electrodes furthest away from the at least first user selected electrode and the at least one second user-selected electrode.

22. The method of claim 21, wherein the one or more electrodes furthest away from the at least first user selected electrode and the at least one second user-selected electrode are lead-based electrodes.

23. A non-transitory computer-readable storage medium comprising instructions that cause a processor to:

receive, via a user interface of a programmer device for an implantable electrical stimulator, user input that specifies at least one first user-selected electrode to deliver electrical stimulation of a first polarity and at least one second user-selected electrode to deliver electrical stimulation of a second polarity different than the first polarity for delivery of electrical stimulation from an implantable electrical stimulator to a patient;

receive, via the user interface, user input specifying amounts of electrical stimulation current to be supplied via the at least one first user-selected electrode and the at least one second user-selected electrode;

automatically select at least one non user-selected third electrode to deliver electrical stimulation to substantially balance the electrical stimulation delivered by the at least one first user-selected electrode and the at least one second user-selected electrode; and define a program to control delivery of the electrical stimulation by the stimulator based on the user input.

24. The computer-readable storage medium of claim 23, wherein the instructions further cause the processor to automatically determine an amount of electrical stimulation to be delivered via the at least one non user-selected third electrode.

25. The computer-readable storage medium of claim 24, wherein the instructions cause the processor to automatically determine the amount of electrical stimulation to be delivered via the at least one third electrode based on a difference between an amount of electrical stimulation delivered via the at least one first user-selected electrode and the at least one second user-selected electrode.

26. The computer-readable storage medium of claim 24, wherein the instructions cause the processor to automatically determine the amount of electrical stimulation to be delivered via the at least one third electrode equal to a difference between an amount of electrical stimulation delivered via the at least one first user-selected electrode and the at least one second user-selected electrode.

27. The computer-readable storage medium of claim 24, wherein the instructions cause the processor to automatically determine the amount of electrical stimulation to be delivered via the at least one third electrode equal to a portion of a difference between an amount of electrical stimulation delivered via the at least one first user-selected electrode and the at least one second user-selected electrode.

28. The computer-readable storage medium of claim 24, wherein the instructions cause the processor to automatically determine the amount of electrical stimulation to be delivered via the at least one third electrode to be a sub-threshold current amplitude below a perception threshold of the patient.

29. The computer-readable storage medium of claim 23, wherein the instructions further cause the processor to:
receive user input specifying the at least one first user-selected electrode and the at least one second user-selected electrode based on a user using a pointing media to select the at least one first user-selected electrode and the at least one second user-selected electrode.

30. The computer-readable storage medium of claim 23, wherein the instructions further cause the processor to:
receive user input specifying the at least one first user-selected electrode and the at least one second user-selected electrode based on user input that drags a stimulation field relative to at least one lead.

31. The computer-readable storage medium of claim 23, wherein the instructions cause the processor to automatically select the at least one third electrode that is one or more lead electrodes.

32. The computer-readable storage medium of claim 23, wherein the instructions cause the processor to automatically select the at least one third electrode that is a housing electrode.

33. The computer-readable storage medium of claim 23, wherein the instructions cause the processor to automatically select the at least one third electrode that is a combination of a housing electrode and at least one lead electrode.

34. The computer-readable storage medium of claim 33, wherein the instructions cause the processor to receive, from a user, input specifying relative contributions of the at least one lead electrode and at least one housing electrode.

35. The computer-readable storage medium of claim 34, wherein the instructions cause the processor to receive, from a user, input specifying relative contributions of the at least one lead electrode and the at least one housing electrode includes receiving user input based on the user adjusting a slideable medium within a range.

36. The computer-readable storage medium of claim 23, wherein the program is a first program, and wherein a first sum of the amounts of electrical stimulation current to be supplied via the at least one first user-selected electrode and the at least one second user-selected electrode and the at least one third electrode substantially equals zero, and wherein the instructions cause the processor to:
receive, via the user interface, user input specifying an adjustment to at least one of the at least one first user-selected electrode and the at least one second user-selected electrode;

automatically determine, for the at least one third electrode, an amount of electrical stimulation current such that a second sum of the electrical stimulation currents to be supplied by each of the first, second, and third electrodes equals zero; and define a second program to control delivery of the electrical stimulation by the stimulator based on the automatically determined amounts of electrical stimulation currents.

37. The computer-readable storage medium of claim 23, wherein the instructions cause the processor to automatically select a plurality of third electrodes not specified as a user-selected electrode to deliver electrical stimulation to substantially balance the electrical stimulation current to be delivered via the at least one first user selected electrode and the at least one second user-selected electrode includes automatically selecting a plurality of third electrodes.

38. The method of claim 37, wherein the instructions cause the processor to automatically determine an amount of electrical stimulation to be delivered via each of the plurality of third electrodes.

39. A device, comprising:
a programmer for an implantable electrical stimulator, the programmer comprising:
a user interface that receives user input that specifies at least one first user-selected electrode to deliver electrical stimulation of a first polarity and at least one second user-selected electrode to deliver electrical stimulation of a second polarity different than the first polarity for delivery of electrical stimulation from an implantable electrical stimulator to a patient, wherein the user interface further receives user input specifying amounts of electrical stimulation current to be supplied via the at least one first user-selected electrode and the at least one second user-selected electrode; and
a processor that automatically selects at least one non user-selected third electrode to deliver electrical stimulation to substantially balance the electrical stimulation delivered by the at least one first user-selected electrode and the at least one second user-selected electrode, wherein the processor defines a program to control delivery of the electrical stimulation by the implantable electrical stimulator based on the user input.

40. The device of claim 39, wherein the processor further automatically determines an amount of electrical stimulation to be delivered via the at least one non-user selected third electrode.

41. The device of claim 40, wherein the processor automatically determines the amount of electrical stimulation to be delivered via the at least one non-user selected third electrode based on a difference between an amount of electrical stimulation delivered via the at least one first user-selected electrode and an amount of electrical stimulation delivered via the at least one second user-selected electrode.

42. The device of claim 40, wherein the processor automatically determines the amount of electrical stimulation to be delivered via the at least one non-user selected third electrode equal to a difference between an amount of electrical stimulation delivered via the at least one first user-selected electrode and an amount of electrical stimulation delivered via the at least one second user-selected electrode.

43. The device of claim 40, wherein the processor automatically determines the amount of electrical stimulation to be delivered via the at least one non-user selected third electrode equal to a portion of a difference between an amount of electrical stimulation delivered via the at least one first user-selected electrode and an amount of electrical stimulation delivered via the at least one second user-selected electrode.

44. The device of claim 40, wherein the processor automatically determines the amount of electrical stimulation to be delivered via the at least one third electrode to be a sub-threshold current amplitude below a perception threshold of the patient.

45. The device of claim 39, wherein the user interface receives user input specifying the at least one first user-selected electrode and the at least one second user-selected electrode based on a user using a pointing media to select the at least one first user-selected electrode and the at least one second user-selected electrode.

46. The device of claim 39, wherein the user interface receives user input specifying the at least one first user-selected electrode and the at least one second user-selected electrode based on user input that drags a stimulation field relative to at least one lead.

47. The device of claim 39, wherein the processor automatically selects the at least one third electrode that is one or more lead electrodes.

48. The device of claim 39, wherein the processor automatically selects the at least one third electrode that is a housing electrode.

49. The device of claim 39, wherein the processor automatically selects the at least one third electrode that is a combination of at least one lead electrode and at least one housing electrode.

50. The device of claim 39, wherein the user interface receives, from a user, input specifying relative contributions of the at least one lead electrode and at least one housing electrode.

51. The device of claim 50, wherein the user interface receives, from a user, input specifying relative contributions of the at least one lead electrode and at least one housing electrode includes the user interface receiving input based on the user adjusting a slideable medium within a range.

52. The device of claim 39, wherein the program is a first program, and wherein a first sum of the amounts of electrical stimulation current to be supplied via the at least one first user-selected electrode and the at least one second user-selected electrode and the at least one third electrode substantially equals zero, and wherein the processor receives, via the user interface, user input specifying an adjustment to at least one of the at least one first user-selected electrode and the at least one second user-selected electrode;
wherein the processor automatically determines, for the at least one third electrode, an amount of electrical stimulation current such that a second sum of the electrical stimulation currents to be supplied by each of the first, second, and third electrodes equals zero; and
wherein the processor defines a second program to control delivery of the electrical stimulation by the stimulator based on the automatically determined amounts of electrical stimulation currents.

53. The device of claim 52, wherein the processor automatically determines an amount of electrical stimulation to be delivered via each of the plurality of electrodes.

54. The device of claim 39, wherein the processor that automatically selects a plurality of non user-selected third electrodes to deliver electrical stimulation to substantially balance the electrical stimulation delivered by the at least one first user-selected electrode and the at least one second user-selected electrode.

55. A device comprising:
means for receiving, via a user interface of a programmer device for an implantable electrical stimulator, user input that specifies at least one first user-selected electrode to deliver electrical stimulation of a first polarity and at least one second user-selected electrode to deliver electrical stimulation of a second polarity different than the first polarity for delivery of electrical stimulation from an implantable electrical stimulator to a patient;
means for receiving, via the user interface, user input specifying amounts of electrical stimulation current to be supplied via the at least one first user-selected electrode and the at least one second user-selected electrode;

means for automatically selecting at least one third electrode to deliver electrical stimulation to substantially balance electrical stimulation delivered by the at least one first user-selected electrode and the at least one second user-selected electrode; and means for defining a program to control delivery of the electrical stimulation by the stimulator based on the user input.

56. A system comprising:

an implantable electrical stimulator; and a programmer comprising:

a user interface that:

receives, via a user interface of a programmer device for an implantable electrical stimulator, user input that specifies at least one first user-selected electrode to deliver electrical stimulation of a first polarity and at least one second user-selected electrode to deliver electrical stimulation of a second polarity different than the first polarity for delivery of electrical stimulation from an implantable electrical stimulator to a patient;

receives, via the user interface, user input specifying amounts of electrical stimulation current to be supplied via the at least one first user-selected electrode and the at least one second user-selected electrode;

wherein the programmer automatically selects at least one third electrode to deliver electrical stimulation to substantially balance electrical stimulation delivered by the at least one first user-selected electrode and the at least one second user-selected electrode; and a processor that defines a program to control delivery of the electrical stimulation by the stimulator based on the user input.

* * * * *